United States Patent
Nagata et al.

(10) Patent No.: US 11,976,062 B2
(45) Date of Patent: *May 7, 2024

(54) BENZISOXAZOLE COMPOUND

(71) Applicants: OSAKA UNIVERSITY, Osaka (JP); KYOTO UNIVERSITY, Kyoto (JP); INTER-UNIVERSITY RESEARCH INSTITUTE CORP NATIONAL INSTITUTES OF NATURAL SCIENCES, Tokyo (JP)

(72) Inventors: Ryu Nagata, Osaka (JP); Yasuo Mori, Kyoto (JP); Masayuki Mori, Kyoto (JP); Motohiro Nishida, Aichi (JP); Takuro Tomita, Aichi (JP)

(73) Assignees: OSAKA UNIVERSITY, Suita (JP); KYOTO UNIVERSITY, Kyoto (JP); INTER-UNIVERSITY RESEARCH INSTITUTE CORPORATION NATIONAL INSTITUTES OF NATURAL SCIENCES, Mitaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/073,180

(22) Filed: Dec. 1, 2022

(65) Prior Publication Data
US 2023/0114195 A1    Apr. 13, 2023

Related U.S. Application Data

(62) Division of application No. 17/050,070, filed as application No. PCT/JP2019/018082 on Apr. 26, 2019, now Pat. No. 11,548,882.

(30) Foreign Application Priority Data

Apr. 27, 2018   (JP) .................... 2018-086929

(51) Int. Cl.
| | |
|---|---|
| *C07D 413/12* | (2006.01) |
| *A61P 43/00* | (2006.01) |
| *C07D 261/20* | (2006.01) |
| *C07D 413/04* | (2006.01) |
| *C07D 413/14* | (2006.01) |
| *C07D 417/12* | (2006.01) |
| *C07D 487/08* | (2006.01) |

(52) U.S. Cl.
CPC ............ *C07D 413/12* (2013.01); *A61P 43/00* (2018.01); *C07D 261/20* (2013.01); *C07D 413/04* (2013.01); *C07D 413/14* (2013.01); *C07D 417/12* (2013.01); *C07D 487/08* (2013.01)

(58) Field of Classification Search
CPC .. C07D 413/12; C07D 261/20; C07D 413/04; C07D 413/14; C07D 417/12; C07D 487/08; A61P 43/00
USPC ........................................................ 514/121
See application file for complete search history.

(56) References Cited

U.S. PATENT DOCUMENTS

| | | | |
|---|---|---|---|
| 11,548,882 B2* | 1/2023 | Nagata ................. A61P 1/16 |
| 2008/0207590 A1 | 8/2008 | Deziel et al. | |
| 2016/0102095 A1 | 4/2016 | Wang et al. | |

FOREIGN PATENT DOCUMENTS

| | | |
|---|---|---|
| JP | H08-506094 A | 7/1996 |
| JP | 2000505084 A | 4/2000 |
| JP | 2002530397 A | 9/2002 |

(Continued)

OTHER PUBLICATIONS

RN 2214763-53-6, RN 2213415-17-7 et al., American Chemical Society (ACS) chemical structure search results from Scientific and Technical Information Network (STN); structures entered STN: Aug. 31, 1994 through Apr. 18, 2018 (71 pages total).

Chinese Office Action dated Feb. 3, 2023 for corresponding Chinese Application No. 201980035770.0, 14 pages (with English Translation).

International Search Report (with English translation) dated Jul. 16, 2019 for corresponding International Application No. PCT/JP2019/018082, 11 pages.

Kiyonaka et al., "Selective and direct inhibition of TRPC3 channels underlies biological activities of a pyrazole compound", 2009, Proc. Nat. Acad. Sci., 2009; vol. 106, No. 13, pp. 5400-5405.

(Continued)

*Primary Examiner* — Kahsay Habte
(74) *Attorney, Agent, or Firm* — MH2 TECHNOLOGY LAW GROUP, LLP

(57) ABSTRACT

The present invention provides a compound, a salt thereof, or a prodrug thereof as a compound effective for preventing and/or treating fibrosis, the compound being represented by formula (1)

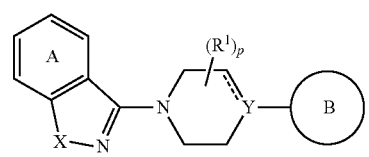

(1)

(wherein A is an optionally substituted benzene ring; B is optionally substituted aryl or optionally substituted heteroaryl; X is an oxygen atom or a sulfur atom; Y is a nitrogen atom or a carbon atom, ------ of ------ Y is a single or double bond when Y is a carbon atom, or ------ of ------ Y is a single bond when Y is a nitrogen atom; each $R^1$ independently represents lower alkyl, or two $R^1$s may be bound to each other to form a spiro ring or a crosslinked structure, or two $R^1$s may be bound to each other to form a saturated fused heterocycle together with nitrogen and carbon atoms constituting a ring containing Y; p is 0, 1, or 2; or $(R^1)_p$ is oxo).

14 Claims, 4 Drawing Sheets

(56) References Cited

FOREIGN PATENT DOCUMENTS

| | | | |
|---|---|---|---|
| JP | 2008513504 A | 5/2008 | |
| JP | 2010508274 A | 3/2010 | |
| JP | 2010508296 A | 3/2010 | |
| JP | 2013533249 A | 8/2013 | |
| WO | 9412495 A1 | 6/1994 | |
| WO | WO-9412495 A1 * | 6/1994 | ............ A61P 25/24 |
| WO | 9730981 A1 | 8/1997 | |
| WO | 0031063 A1 | 6/2000 | |
| WO | 2006101521 A2 | 9/2006 | |
| WO | 2008054702 A1 | 5/2008 | |
| WO | 2009137503 A1 | 11/2009 | |
| WO | 2010054279 A1 | 5/2010 | |
| WO | 2012001107 A1 | 1/2012 | |
| WO | 2012037351 A1 | 3/2012 | |
| WO | 2018118781 A1 | 6/2018 | |

OTHER PUBLICATIONS

Kurahara et al., "Significant contribution of TRPC6 channel-mediated Ca2+ influx to the pathogenesis of Crohn's Disease fibrotic stenosis", 2016, Journal of Smooth Muscle Research, vol. 52, pp. 78-92.

Kurahara et al., "Intestinal FibroblasUMyofibroblast TRP Channels in Inflammatory Bowel Disease", 2016, InTechOpen, 17 pages.

Letavernier et al., "Williams-Beuren syndrome hypercalcemia: is TRPC3 a novel mediator in calcium homeostasis?", 2012, Pediatrics, 2012, vol. 129, e1626-30, 8 pages.

Maier et al., "Discovery and pharmacological characterization of a novel potent inhibitor of diacylglycerol-sensitive TRPC cation channels", 2015, British Journal of Pharmacology, vol. 172, pp. 3650-3660.

Millay et al., "Calcium influx is sufficient to induce muscular dystrophy through a TRPC-dependent mechanism", 2009, Proc. Nat. Acad. Sci., vol. 106, No. 45, pp. 19023-19028.

Naidu et al., "Design, synthesis and antimycobacterial activity of various 3-(4-(substitutedsulfonyl)piperazin-1-yl) benzodJisoxazole derivatives", 2014, European Journal of Medicinal Chemistry, vol. 87, pp. 71-78.

Numaga-Tomita et al., "TRPC3-GEF-H1 axis mediates pressure overload-induced cardiac fibrosis", 2016, Scientific Reports, vol. 6, e39383, 12 pages.

Qu et al., "Pyrazolopyrimidines as Potent Stimulators for Transient Receptor Potential Canonical 3/6{7 Channels", 2017, Journal of Medicinal Chemistry, vol. 60, pp. 4680-4692.

Saliba et al., "Evidence of a Role for Fibroblast Transient Receptor Potential Canonical 3 Ca+ Channel in Renal Fibrosis", 2015, Journal of the American Society of Nephrology, vol. 26, pp. 1855-1876.

Sawamura et al., "Screening of Transient Receptor Potential Canonical Channel Activators Identifies Novel Neurotrophic Piperazine Compounds", 2016, Molecular Pharmacology, vol. 89, No. 3, pp. 348-363.

Seo et al., "Combined TRPC3 and TRPC6 blockade by selective small-molecule or genetic deletion inhibits Pathological cardiac hypertrophy", 2014, Proc. Nat. Acad. Sci., vol. 111, No. 16, pp. 1551-1556.

Shastri, R. A., "Review on Synthesis of 3-Substituted 1,2-Benzisoxazole Derivatives", 2016, Chemical Science Transactions, vol. 5, No. 1, pp. 8-20.

Sheth et al., "Mechanisms of Cisplatin-Induced Ototoxicity and Otoprotection", 2017, Frontiers in Cellular Neuroscience, vol. 11, Article 338, 12 pages.

Shimauchi et al., "TRPC3-Nox2 complex mediates doxorubicin-induced myocardial atrophy", 2017, JCI Insight, vol. 2, No. 15, e93358, 18 pages.

Smedlund et al., "Early steatohepatitis in hyperlipidemic mice with endothelial-specific gain of TRPC3 function precedes changes in aortic atherosclerosis", 2016, Physiol Genomics, vol. 48, p. 644-649.

Washburn et al., "The discovery of potent blockers of the canonical transient receptor channels, TRPC3 and TRPC6, based on an anilino-thiazole pharmacophore", 2013, Bioorganic & Medicinal Chemistry Letters, vol. 23, pp. 4979-4984.

Wu et al., "Inhibition of TRPC6 channels ameliorates renal fibrosis and contributes to renal protection by soluble Klotho", 2017, Kidney International, vol. 91, No. 4, pp. 830-841.

Office Action dated Jun. 21, 2022 for corresponding Japanese Patent Application No. 2020-515628, 9 pages including English translation.

"Database Registry" [online], [retrieved on Jul. 3, 2019], American Chemical Society, Retrieved from: STN, <URL:https://next.stn.org/>, Entered STN: Nov. 11, 2007 RN: 952906-59-1, CN: Benzenamine, 4-[4-(1, 2-benzisothiazol-3-yl )-1-piperazinyl]-3-fluoro-{CA Index Name), RN: 952905-69-0, CN: Benzonitrile, 5-amino-2-[4-(1, 2-benzisothiazol-3-yl)-1-piperazinyl]-(CA Index Name).

"Database Registry" [online], [retrieved on Jul. 3, 2019], American Chemical Society, Retrieved from: STN, <URL:https://next.stn.org/>, Entered STN: Apr. 18, 2018, RN: 2214763-53-6, CN: Benzoic acid, 2-[4-(1, 2-benzisothiazol-3-yl)-1-piperazinyl]-5-nitro-(CA Index Name), RN: 2213415-17-7, CN: Benzoic acid, 5-amino-2-[4-(1, 2-benzisothiazol-3-yl)-1-piperazinyl]-(CA Index Name).

"Database Registry" [online], [retrieved on Jul. 3, 2019], American Chemical Society, Retrieved from: STN, ic: URL:https://next.stn.org/>, Entered STN : Sep. 12, 2007, RN: 946731-44-8, CN : 3-Pyridinecarbonitrile, 2-[4-(1, 2-benzisothiazol-3-yl)-1-piperazinyl]-(CA Index Name), RN: 945367-69-1, CN: Benzonitrile, 2-[4-(1, 2-benzisothiazol-3-yl)-1-piperazinyl]-5-nitro-(CA Index Name).

"Database Registry" [online], [retrieved on Jul. 3, 2019], American Chemical Society, Retrieved from: STN, <https://nextstn.org/>, Entered STN: Jul. 7, 2016, RN: 1947055-80-2, CN: 1,2-Benzisoxazole, 5-bromo-3-[4-(3-methyl-1, 2, 4-thiadiazol-5-yl)-1-piperazinyl]-(CA Index Name), RN: 1947025-34-4, CN: 1, 2-Benzisoxazole, 5-bromo-3-[4-(4, 6-dimethy 1-2-pyrimidinyl)-1-piperazinyl]-(CA Index Name).

Chu-Moyer et al., "Orally-Effective, Long-Acting Sorbitol Dehydrogenase Inhibitors: Synthesis, Structure-Activity Relationships, and in Vivo Evaluations of Novel Heterocycle-Substituted Piperazino-Pyrimidines", 2002, Journal of Medicinal Chemistry, vol. 45, No. 2, pp. 511-528.

Guedes De La Cruz et al., "Intensified Microwave-Assisted N-Acylation Procedure-Synthesis and Activity Evaluation of TRPC3 Channel Agonists with a 1,3-Dihydro-2H-benzo[d]imidazol-2-one Core", 2017, Synlett, vol. 28, No. 6, pp. 695-700.

Hofmann et al., "Classical transient receptor potential 6 (TRPC6) channels support myofibroblast differentiation and development of experimental pulmonary fibrosis", 2017, Biochimica et Biophysica Acta, vol. 1863, pp. 560-568.

Kitajima et al., "TRPC3 positively regulates reactive oxygen species driving maladaptive cardiac remodeling", 2016, Scientific Reports, vol. 6, e37001, 14 pages.

* cited by examiner

BENZISOXAZOLE COMPOUND

CROSS-REFERENCE TO RELATED APPLICATIONS

This application is a divisional of U.S. patent application Ser. No. 17/050,070 (Allowed) filed 23 Oct. 2020, which is a U.S. National Stage application of PCT/JP2019/018082 filed 26 Apr. 2019, which claims priority to Japanese Application No. 2018-086929 filed 27 Apr. 2018, the entire disclosures of which are hereby incorporated by reference in their entireties.

TECHNICAL FIELD

The present invention relates to a benzisoxazole compound.

BACKGROUND ART

Organ or tissue fibrosis is caused by the excessive accumulation of extracellular matrix in an organ, which is a repair or defense mechanism driven by invasion or injury in the organ that occurs for some reason. The extracellular matrix refers to substances surrounding the cells of tissue, and main substances include, for example, fibrous proteins such as collagen and elastin, glycoconjugates such as proteoglycans, and glycoproteins such as fibronectin and laminins. For example, if the damage to an organ caused by invasion or injury is minor, no repair scar remains, and the organ returns to normal. However, if the damage to the organ caused by invasion or injury is severe or persistent, the fibrosis of repair scaring impairs the fundamental function of the organ. This further causes new fibrosis to form, forming a vicious circle. Ultimately, failure of the organ occurs, leading to death in the worst case.

The transient receptor potential (TRP) gene was identified in 1989 as a gene responsible for the photoreceptor response mutant strain of *Drosophila*. Subsequent studies have found in mammals many proteins that share homology with the protein encoded by the TRP gene, and that such proteins basically function as cation channels in cell membranes. TRP channels form a superfamily with enormous functional diversity and are classified into groups such as TRPA, TRPV, TRPM, and TRPC. The TRPC (TRP classic or TRP canonical) group is further classified into TRP C1 to C7 subgroups.

It is known that TRPC3-deficient mice show resistance to cardiac fibrosis induced by pressure overload, and that administration of Pyr3, which is a TRPC3 channel inhibitor, potently suppresses cardiac fibrosis induced by pressure overload in mice (NPL 1 and 2). TRPC6-deficient mice also show resistance to bleomycin-induced pulmonary fibrosis and renal interstitial fibrosis caused by unilateral ureteral obstruction (NPL 3 and 4), and administration of Pyr2 (BTP2), which is an inhibitor of TRPC3 and TRPC6 channels, suppresses renal interstitial fibrosis caused by unilateral ureteral obstruction in mice.

Thus, regulating the activity of the TRPC3 channel or TRPC6 channel ("TRPC3 regulation or TRPC6 regulation") or inhibiting the activity of the TRPC3 channel or TRPC6 channel ("TRPC3 inhibition or TRPC6 inhibition") is useful as a fibrosis inhibitor for organs (e.g., lungs, heart, kidneys, and liver) and tissues (NPL 1 to 5), and is also considered to be effective in neurodegenerative diseases, muscular degenerative diseases, and inflammatory diseases, such as amyotrophic lateral sclerosis (ALS), muscular dystrophy, ulcerative colitis, Crohn's disease, non-alcoholic steatohepatitis (NASH), and Williams syndrome (NPL 6 to 12).

Studies report, for example, Pyr2 (BTP2), Pyr3, Pyr4, GSK2332255B, GSK2833503A, and SAR7334 as compounds that exhibit TRPC3 and/or TRPC6 inhibitory activity (NPL 13 to 18).

CITATION LIST

Non-Patent Literature

NPL: 1: Numaga-Tomita, T. et al., TRPC3-GEF-H1 axis mediates pressure overload-induced cardiac fibrosis. Sci. Rep. 6, 39383; doi: 10.1038/srep 39383 (2016).

NPL: 2: Kitajima, N. et al., TRPC3 positively regulates reactive oxygen species driving maladaptive cardiac remodeling. Sci. Rep. 6, 37001 (2016).

NPL: 3: Y.-L. Wu et al., Inhibition of TRPC6 channels ameliorates renal fibrosis and contributes to renal protection by soluble klotho. Kidney Int., 2017 April; 91(4): 830-841.

NPL: 4: K. Hofmann et al., Classical transient receptor potential 6 (TRPC6) channels support myofibroblast differentiation and development of experimental pulmonary fibrosis. Biochimica et Biophysica Acta, 2017; 1863: 560-568.

NPL: 5: Y. Saliba et al., Evidence of a Role for Fibroblast Transient Receptor Potential Canonical 3 Ca Channel in Renal Fibrosis. J Am Soc Nephrol., 2015; 26: 1855-1876.

NPL: 6: K. Seoa et al., Combined TRPC3 and TRPC6 blockade by selective small-molecule or genetic deletion inhibits pathological cardiac hypertrophy, Proc. Nat. Acad. Sci., 2014; 111: 1551-1556.

NPL: 7: T. Shimauchi et al., TRPC3-Nox2 complex mediates doxorubicin-induced myocardial atrophy. JCI Insight, 2017; 2(15). pii: 93358.

NPL: 8: K. Smedlund et al., Early steatohepatitis in hyperlipidemic mice with endothelial-specific gain of TRPC3 function precedes changes in aortic atherosclerosis. Physiol Genomics, 2016; 48: 644-649.

NPL: 9: L. H. Kurahara et al., Intestinal Fibroblast/Myofibroblast TRP Channels in Inflammatory Bowel Disease, "New Insights into Inflammatory Bowel Disease," book edited by Samuel Huber, 2016, InTech.

NPL: 10: L. H. Kurahara et al., Significant contribution of TRPC6 channel-mediated Ca2+ influx to the pathogenesis of Crohn's disease fibrotic stenosis. J. Smooth Muscle Res., 2016; 52: 78-92.

NPL: 11: E. Letavernier et al., Williams-Beuren syndrome hypercalcemia: is TRPC3a novel mediator in calcium homeostasis?, Pediatrics, 2012; 129: e1626-30.

NPL: 12: P. Douglas et al., Calcium influx is sufficient to induce muscular dystrophy through a TRPC-dependent mechanism, Proc. Nat. Acad. Sci., 2009; 106: 19023-19028.

NPL: 13: S. Kiyonaka et al., Selective and direct inhibition of TRPC3 channels underlies biological activities of a pyrazole compound, Proc. Nat. Acad. Sci., 2009; 106: 5400-5405.

NPL: 14: T. Maier et al., Discovery and pharmacological characterization of a novel potent inhibitor of diacylglycerol-sensitive TRPC cation channels, Br. J. Pharmacol., 2015; 172: 3650-3660.

NPL: 15: D. G. Washburn et al., The discovery of potent blockers of the canonical transient receptor channels, TRPC3 and TRPC6, based on an anilino-thiazole pharmacophore, Bioorg. Med. Chem. Lett., 2013; 23: 4979-4984.

NPL: 16: C. Qu et al., Pyrazolopyrimidines as Potent Stimulators for Transient Receptor Potential Canonical 3/6/7 Channels, J. Med. Chem., 2017; 60: 4680-4692.

NPL: 17: G. Guedes et al., Intensified Microwave-Assisted N-Acylation Procedure-Synthesis and Activity Evaluation of TRPC3 Channel Agonists with a 1,3-Dihydro-2H-benzo[d]imidazol-2-one Core, Synlett, 2017; 28: 695-700.

NPL: 18: S. Sawamura et al., Screening of Transient Receptor Potential Canonical Channel Activators Identifies Novel Neurotrophic Piperazine Compounds, Mol Pharmacol., 2016; 89: 348-363.

SUMMARY OF INVENTION

Technical Problem

An object of the present invention is to provide a compound and the like that regulate or inhibit the activity of TRPC channels, in particular the TRPC3 channel or TRPC6 channel, or both the TRPC3 channel and TRPC6 channel (which may be collectively referred to as the "TRPC3 and/or TRPC6 channel" in the present specification), and to provide uses of the compound or the like.

Solution to Problem

To achieve the above object, the present inventors conducted extensive research. As a result, they found that the above object can be achieved by a compound represented by formula (1) or formula (2) described below, a salt thereof, or a prodrug thereof (which may be collectively referred to below as the "compound of the present invention and the like"), and have accomplished the present invention. Representative inventions of the present invention are as follows.

Item 1.

A compound represented by formula (1):

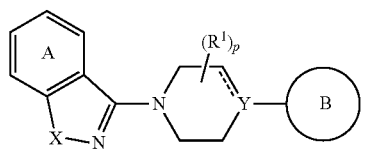

(1)

wherein A is an optionally substituted benzene ring;
B is optionally substituted aryl or optionally substituted heteroaryl;
X is an oxygen atom or a sulfur atom;
Y is a nitrogen atom or a carbon atom;
------ of ------ Y is a single or double bond when Y is a carbon atom, or
------ of ------ Y is a single bond when Y is a nitrogen atom;
each $R^1$ independently represents lower alkyl, or
two $R^1$s may be bound to each other to form a spiro ring or a crosslinked structure, or
two $R^1$s may be bound to each other to form a saturated fused heterocycle together with nitrogen and carbon atoms constituting
a ring containing Y;
p is 0, 1, or 2; or
$(R^1)_p$ is oxo;
a salt thereof; or
a prodrug thereof.

Item 2.

The compound according to Item 1, a salt thereof, or a prodrug thereof, wherein in formula (1), B is an optionally substituted monocyclic aryl or an optionally substituted monocyclic or bicyclic nitrogen-containing heteroaryl.

Item 3.

The compound according to Item 1 or 2, a salt thereof, or a prodrug thereof, wherein in formula (1), A is a benzene ring optionally substituted with at least one substituent selected from the group consisting of the following A-1 to A-16:

A-1) halogen,
A-2) hydroxyl,
A-3) nitro,
A-4) cyano,
A-5) carboxyl,
A-6) optionally substituted amino,
A-7) optionally substituted cyclic amino,
A-8) optionally substituted lower alkyl,
A-9) optionally substituted lower alkoxy,
A-10) lower alkoxycarbonyl,
A-11) lower alkylsulfonyl,
A-12) carbamoyl optionally substituted with lower alkyl or lower alkylsulfonyl,
A-13) optionally substituted cyclic aminocarbonyl,
A-14) sulfamoyl optionally substituted with lower alkyl,
A-15) optionally substituted cyclic aminosulfonyl, and
A-16) tetrazolyl.

Item 4.

The compound according to any one of Items 1 to 3, a salt thereof, or a prodrug thereof, wherein in formula (1), B is monocyclic aryl or monocyclic or bicyclic heteroaryl, the monocyclic aryl is optionally substituted with at least one substituent selected from the group consisting of the following B-1 to B-16, and
the monocyclic or bicyclic heteroaryl is optionally substituted with at least one substituent selected from the group consisting of the following B-1 to B-17:

B-1) halogen,
B-2) hydroxyl,
B-3) nitro,
B-4) cyano,
B-5) carboxyl
B-6) optionally substituted amino,
B-7) optionally substituted cyclic amino,
B-8) optionally substituted lower alkyl,
B-9) optionally substituted lower alkoxy,
B-10) lower alkoxycarbonyl,
B-11) lower alkyl sulfonyl,
B-12) carbamoyl optionally substituted with lower alkyl or lower alkylsulfonyl,
B-13) optionally substituted cyclic aminocarbonyl,
B-14) sulfamoyl optionally substituted with lower alkyl,
B-15) optionally substituted cyclic aminosulfonyl,
B-16) tetrazolyl, and
B-17) oxo.

Item 5.

The compound according to any one of Items 1 to 4, a salt thereof, or a prodrug thereof, wherein in formula (1), the benzisoxazole or benzisothiazole skeleton is substituted at the 4-position.

Item 6.

The compound according to any one of Items 1 to 3, a salt thereof, or a prodrug thereof, wherein in formula (1), B is substituted pyridyl or substituted phenyl, wherein at least one of the carbon atoms in ortho-positions relative to the Y-bound carbon atom on the pyridine or benzene ring is substituted.

Item 7.

The compound according to any one of Items 1 to 4, a salt thereof, or a prodrug thereof, wherein in formula (1), A is a benzene ring optionally substituted with at least one substituent selected from the group consisting of halogen, lower alkoxy, and optionally halogen-substituted lower alkyl; B is pyridyl or phenyl each optionally substituted with at least one substituent selected from the group consisting of B-1, B-5, B-8, B-10, B-12, and B-13:
- B-1) halogen,
- B-5) carboxyl,
- B-8) optionally substituted lower alkyl,
- B-10) lower alkoxycarbonyl,
- B-12) carbamoyl optionally substituted with lower alkyl or lower alkylsulfonyl, and
- B-13) optionally substituted cyclic aminocarbonyl; and each $R^1$ independently represents $C_1$-$C_3$ alkyl, or two $R^1$s are bound to each other to form a methylene group, a dimethylene group, or a trimethylene group, or $(R^1)_p$ is oxo.

Item 8.

The compound according to any one of Items 1 to 4 and 7, a salt thereof, or a prodrug thereof, the compound being represented by formula (1A):

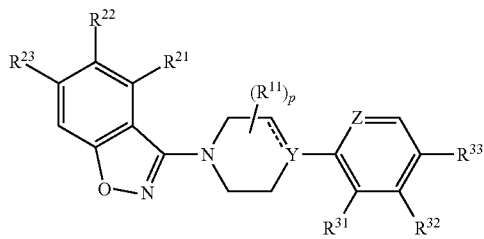

(wherein Z is a nitrogen atom or CH;
Y is a nitrogen atom or a carbon atom;
------ of ------ Y is a single or double bond when Y is a carbon atom, or ------ of ------ Y is a single bond when Y is a nitrogen atom;
each $R^{11}$ independently represents methyl or ethyl, or two $R^{11}$s may be bound to each other to form a crosslinked structure by methylene, dimethylene, or trimethylene;
p is 0, 1, or 2; or
$(R^{11})_p$ is oxo;
$R^{21}$, $R^{22}$, and $R^{23}$ independently represent a hydrogen atom, halogen, or trifluoromethyl; and
$R^{31}$, $R^{32}$, and $R^{33}$ independently represent a hydrogen atom, halogen, halogen-substituted lower alkyl, methyl, carboxyl, lower alkoxycarbonyl, monomethyl aminocarbonyl, or dimethylaminocarbonyl).

Item 9.

The compound according to Item 8, a salt thereof, or a prodrug thereof, wherein in formula (1A),
$R^{21}$ is a chlorine atom or trifluoromethyl,
$R^{22}$ and $R^{23}$ are each a hydrogen atom,
$R^{31}$ is a chlorine atom,
$R^{32}$ is a hydrogen atom, and
$R^{33}$ is a hydrogen atom, carboxyl, or lower alkoxycarbonyl.

Item 10.

The compound according to any one of Items 1 to 4, a salt thereof, or a prodrug thereof, wherein the compound is Compound 011, Compound 021, Compound 031, Compound 041, Compound 061, Compound 071, Compound 081, Compound 091, Compound 101, Compound 111, Compound 121, Compound 131, Compound 141, Compound 151, Compound 161, Compound 171, Compound 191, Compound 221, Compound 281, Compound 311, Compound 321, Compound 331, Compound 341, Compound 351, Compound 361, Compound 371, Compound 381, Compound 391, or Compound 401.

Item 11.

A compound represented by formula (2):

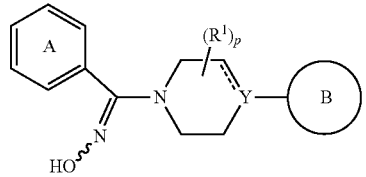

wherein A is an optionally substituted benzene ring;
B is optionally substituted aryl or optionally substituted heteroaryl;
Y is a nitrogen atom or a carbon atom;
------ of ------ Y is a single or double bond when Y is a carbon atom, or
------ of ------ Y is a single bond when Y is a nitrogen atom;
each $R^1$ independently represents lower alkyl, or
two $R^1$s may be bound to each other to form a spiro ring or a crosslinked structure, or
two $R^1$s may be bound to each other to form a saturated fused heterocycle together with nitrogen and carbon atoms constituting
a ring containing Y;
p is 0, 1, or 2; or
$(R^1)_p$ is oxo.

Item 12.

A pharmaceutical composition comprising the compound of any one of Items 1 to 11, a salt thereof, or a prodrug thereof.

Item 13.

The pharmaceutical composition according to Item 12, which is a prophylactic and/or therapeutic agent for a TRPC3 and/or TRPC6-related disease.

Item 14.

The pharmaceutical composition according to Item 13, wherein the TRPC3 and/or TRPC6-related disease is fibrosis, cardiac hypertrophy, amyotrophic lateral sclerosis (ALS), muscular dystrophy, ulcerative colitis, Crohn's disease, non-alcoholic steatohepatitis (NASH), Williams syndrome, chronic nephropathy, or Alzheimer's disease.

Item 15.

A TRPC3 and/or TRPC6 regulator or inhibitor comprising the compound of any one of Items 1 to 11, a salt thereof, or a prodrug thereof.

Advantageous Effects of Invention

The compound and the like according to the present invention have an activity of regulating or inhibiting the activity of TRPC channels, such as the TRPC3 channel and/or TRPC6 channel, preferably the TRPC6 channel.

Therefore, the compound and the like are effective for TRPC-related diseases, such as diseases caused by TRPC3-channel activity, diseases caused by TRPC6-channel activity, or diseases caused by both TRPC3-channel activity and TRPC6-channel activity (which may be collectively referred to as "TRPC3 and/or TRPC6-related diseases" in the present specification), and particularly useful for preventing and/or treating fibrosis.

BRIEF DESCRIPTION OF THE DRAWINGS

In FIG. 5, the vertical axis of the graph on the left indicates current (nA), and the horizontal axis indicates time (seconds). In the graph on the right, "a" and "b" respectively indicate a current-voltage characteristic curve at the time point of a and b in the graph on the left.

Figure 1:
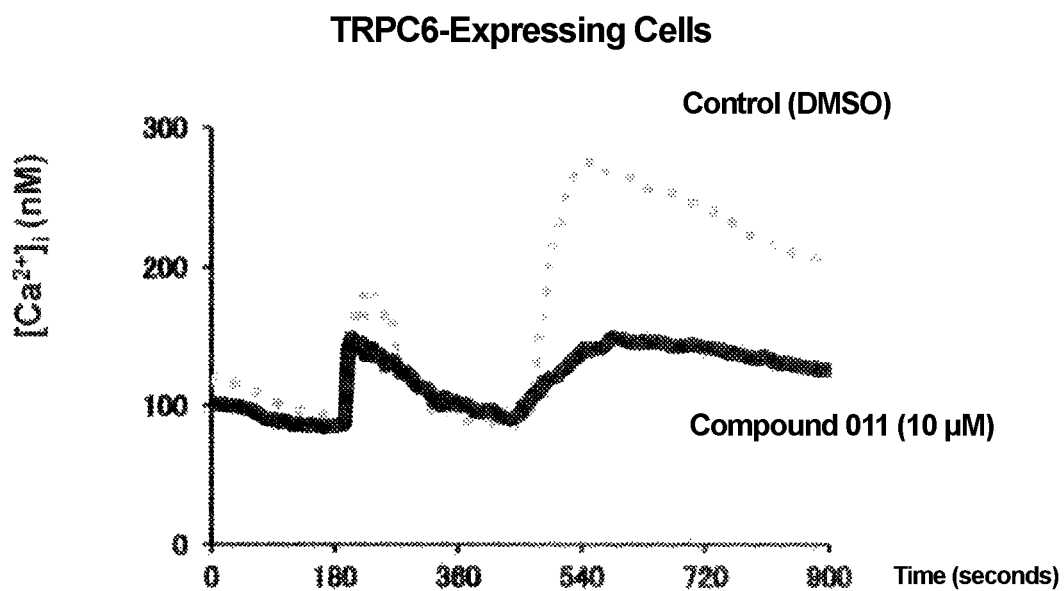
FIG. 1 is a graph illustrating the measurement results of changes in calcium ion concentration in the TRPC6-expressing cells obtained in Test Example 1. The horizontal axis indicates time (seconds), and the vertical axis indicates the calcium ion concentration in cells ($[Ca^{2+}]i$ (nM)).

One embodiment of the present invention is a compound represented by the following formula (1), a salt thereof, or a prodrug thereof.

Formula (1):

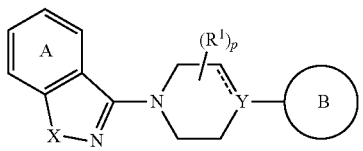

(1)

(wherein A is an optionally substituted benzene ring;
B is an optionally substituted aryl or an optionally substituted heteroaryl;
X is an oxygen atom or a sulfur atom;
Y is a nitrogen atom or a carbon atom;
------ of ------ Y is a single or double bond when Y is a carbon atom, or
------ of ------ Y is a single bond when Y is a nitrogen atom;
each $R^1$ independently represents lower alkyl, or
two $R^1$s may be bound to each other to form a spiro ring or a crosslinked structure, or
two $R^1$s may be bound to each other to form a saturated fused heterocycle together with nitrogen and carbon atoms constituting a ring containing Y;
p is 0, 1, or 2; or
$(R^1)_p$ is oxo).

In the present invention, examples of substituents for the "optionally substituted benzene ring" include halogen; hydroxyl; nitro; cyano; carboxyl; optionally substituted amino; optionally substituted cyclic amino; optionally substituted lower alkyl; optionally substituted lower alkoxy; lower alkoxycarbonyl; lower alkylsulfonyl; carbamoyl optionally substituted with lower alkyl or lower alkylsulfonyl; optionally substituted cyclic aminocarbonyl; sulfamoyl optionally substituted with lower alkyl; optionally substituted cyclic aminosulfonyl; tetrazolyl; and the like. Such substituents may be used singly or in a combination of two or more.

In the present invention, the "aryl" may be, for example, monocyclic or bicyclic aryl. Specific examples include phenyl, naphthyl, and the like.

In the present invention, the aryl of the "optionally substituted aryl" is as defined above. Examples of substituents of the optionally substituted aryl include halogen; hydroxyl; nitro; cyano; carboxyl; optionally substituted amino; optionally substituted cyclic amino; optionally substituted lower alkyl; optionally substituted lower alkoxy; lower alkoxycarbonyl; lower alkylsulfonyl; carbamoyl optionally substituted with lower alkyl or lower alkylsulfonyl; optionally substituted cyclic aminocarbonyl; sulfamoyl optionally substituted with lower alkyl; optionally substituted cyclic aminosulfonyl; tetrazolyl; oxo; and the like. Such substituents may be used singly or in a combination of two or more.

In the present invention, the "oxo" is a group represented by "=O".

In the present invention, the "heteroaryl" is, for example, monocyclic or bicyclic nitrogen-containing heteroaryl. Specific examples include monocyclic or bicyclic nitrogen-containing heteroaryl that contains one or more (for example, one to three, one or two, or one) nitrogen atoms on the ring and optionally further contains one or more (for example, one to three, one or two, or one) sulfur atoms or oxygen atoms as other hetero atoms. Specific examples of the heteroaryl include pyrrolyl, imidazolyl, triazolyl, tetrazolyl, pyrazolyl, pyridyl, pyrazinyl, pyrimidinyl, pyridadinyl, furyl, thienyl, oxazolyl, isooxazolyl, thiazolyl, isothiazolyl, frazayl, oxadiazolyl, thiadiazolyl, indolyl, isoindolyl, benzofuranyl, isobenzofuranyl, benzothienyl, isobenzothienyl, indazolyl, quinolyl, isoquinolyl, purinyl, phthalazinyl, pteridyl, naphthyridinyl, quinoxalinyl, quinazolinyl, cinnolinyl, benzoxazolyl, benzothiazolyl, benzoimidazolyl, benzofurazanyl, benzothiadiazolyl, benzotriazolyl, isoxazolo[4,5-d]pyridazyl, benzisoxazolyl, benzisothiazolyl, and the like.

In the present invention, the heteroaryl of the "optionally substituted heteroaryl" is as defined above. Examples of substituents for the optionally substituted heteroaryl include halogen; hydroxyl; nitro; cyano; carboxyl; optionally substituted amino; optionally substituted cyclic amino; optionally substituted lower alkyl; optionally substituted lower alkoxy; lower alkoxycarbonyl; lower alkylsulfonyl; carbamoyl optionally substituted with lower alkyl or lower alkylsulfonyl; optionally substituted cyclic aminocarbonyl; sulfamoyl optionally substituted with lower alkyl; optionally substituted cyclic aminosulfonyl; tetrazolyl; oxo; and the like. Such substituents may be used singly or in a combination of two or more.

In the present invention, the "lower alkyl" includes, for example, $C_1$-$C_8$ alkyl, preferably $C_1$-$C_6$ alkyl, more preferably $C_1$-$C_4$ alkyl, and particularly preferably $C_1$-$C_3$ alkyl, each containing a linear, branched, or cyclic structure. Specific examples of the linear or branched lower alkyl include methyl, ethyl, 1-propyl, 2-propyl, 1-butyl, 2-butyl, isobutyl, t-butyl, n-pentyl, neopentyl, n-hexyl, isohexyl, 3-methylpentyl, and the like. Examples of the lower alkyl containing a cyclic structure include cyclopropyl, cyclopropylmethyl, cyclobutyl, cyclobutylmethyl, cyclopentyl, cyclopentylmethyl, cyclohexyl, cyclohexylmethyl, cyclohexylethyl, and the like. Preferable examples include methyl, ethyl, 2-propyl, t-butyl, cyclopropyl, and the like.

In the present invention, examples of the "halogen" in the present invention include a fluorine atom, a chlorine atom, a bromine atom, an iodine atom, and the like. Preferable examples include a fluorine atom and a chlorine atom.

In the present invention, the "optionally substituted amino" refers to an optionally substituted acyclic amino group. Examples of substituents for the amino group include lower alkyl (e.g., methyl, ethyl, and propyl), $C_1$-$C_8$ acyl (e.g., acetyl and propionyl), aryl (e.g., phenyl), and heteroaryl. Such substituents may be used singly or in a combination of two or more. Preferable examples of the optionally substituted amino include amino, methylamino, dimethylamino, ethylamino, diethylamino, cyclohexylamino, acetylamino, benzoylamino, phenylamino, and the like.

In the present invention, the "cyclic amino" may be, for example, a 5- to 7-membered cyclic amino group containing a nitrogen atom as a ring-constituting atom and optionally further containing one or more (for example, one to three, one or two, or one) oxygen atoms. Specific examples include pyrrolidino, piperidino, piperazino, morpholino, and the like. Preferable examples include pyrrolidino, morpholino, and the like.

In the present invention, the cyclic amino of the "optionally substituted cyclic amino" is as defined above. Examples of substituents for the cyclic amino include lower alkyl, lower alkoxy, amino, hydroxyl, nitro, cyano, carboxyl, oxo, and the like. The cyclic amino may be substituted with at least one substituent selected from the group consisting of the substituents mentioned above. The number of substituents is, for example, 0, 1, 2, and 3, and preferably 0, 1, and 2. Specific examples of the optionally substituted cyclic amino include pyrrolidino, piperidino, piperazino, 4-methylpiperidino, morpholino, 2-pyrrolidonyl, and the like. Preferable examples include pyrrolidino, morpholino, and the like.

In the present invention, the lower alkyl of the "optionally substituted lower alkyl" is as defined above. Examples of substituents for the lower alkyl include hydroxyl; amino; $C_1$-$C_8$ alkylamino (e.g., methylamino, ethylamino, propylamino, and t-butylamino); $C_1$-$C_8$ alkoxy (e.g., methoxy, ethoxy, 1-propyloxy, 2-propyloxy, and t-butyloxy); halogen (e.g., a fluorine atom, a chlorine atom, and a bromine atom); halo-$C_1$-$C_8$ alkoxy (e.g., trifluoromethoxy); aliphatic heterocyclic groups (e.g., morpholino, piperidinyl, pyrrolidinyl, and 4-methyl-1-piperazino); aryl (e.g., phenyl and 1-naphthyl); heteroaryl (e.g., pyridyl, thienyl, and furanyl); carboxyl; $C_1$-$C_8$ alkoxycarbonyl (e.g., methoxycarbonyl, ethoxycarbonyl, 1-propoxycarbonyl, 2-propoxycarbonyl, and t-butoxycarbonyl); carbamoyl optionally substituted with lower alkyl (e.g., carbamoyl, methylaminocarbonyl, dimethylaminocarbonyl, and diethylaminocarbonyl); cyclic aminocarbonyl (e.g., pyrrolidinocarbonyl, piperidinocarbonyl, and morpholinocarbonyl); and the like. Examples of preferable substituents include methylamino, ethylamino, dimethylamino, diethylamino, methoxy, ethoxy, 2-propyloxy, t-butoxycarbonyl, hydroxyl, a fluorine atom, a chlorine atom, trichloromethyl, trifluoromethyl, trifluoromethoxy, morpholino, piperidino, pyrrolidino, carboxyl, methoxycarbonyl, ethoxycarbonyl, morpholinocarbonyl, phenyl, pyridyl, and the like. The optionally substituted lower alkyl may be substituted with at least one substituent selected from the group consisting of the substituents mentioned above. The number of substituents may be, for example, 0, 1, 2, or 3, and preferably 0, 1, or 2.

In the present invention, "halogen-substituted lower alkyl" means that all the hydrogen atoms of the alkyl are replaced by halogen atoms. The halogen and lower alkyl of the halogen-substituted lower alkyl are as defined above. The halogen atoms with which the alkyl is substituted are preferably of the same kind. The halogen-substituted lower alkyl is preferably trichloromethyl or trifluoromethyl, and more preferably trifluoromethyl.

In the present invention, examples of the "lower alkoxy" include $C_1$-$C_8$ alkoxy, preferably $C_1$-$C_6$ alkoxy, more preferably $C_1$-$C_4$ alkoxy, and particularly preferably $C_1$-$C_3$ alkoxy, each containing a linear, branched, or cyclic structure. Specific examples of the linear or branched alkoxy include methoxy, ethoxy, 1-propoxy, 2-propoxy, 1-butoxy, 2-butoxy, isobutoxy, t-butoxy, n-pentyloxy, neopentyloxy, n-hexyloxy, isohexyloxy, 3-methylpentyloxy, and the like. Examples of the alkoxy containing a cyclic structure include cyclopropoxy, cyclopropylmethoxy, cyclobutyloxy, cyclobutylmethoxy, cyclopentyloxy, cyclopentylmethoxy, cyclohexyloxy, cyclohexylmethoxy, cyclohexylethoxy, and the like. Preferable examples are methoxy, ethoxy, 2-propoxy, t-butoxy, cyclopropoxy, and the like.

In the present invention, the lower alkoxy of the "optionally substituted lower alkoxy" is as defined above. Examples of substituents for the lower alkoxy include hydroxyl; amino; $C_1$-$C_8$ alkylamino (e.g., methylamino, ethylamino, propylamino, and t-butylamino); $C_1$-$C_8$ alkoxy (e.g., methoxy, ethoxy, 1-propyloxy, 2-propyloxy, and t-butoxy); halogen (e.g., a fluorine atom, a chlorine atom, and a bromine atom); halo-$C_1$-$C_8$ alkoxy (e.g., trifluoromethoxy); aliphatic heterocyclic groups (e.g., morpholino, piperidinyl, pyrrolidinyl, and 4-methyl-1-piperazino); aryl (e.g., phenyl and 1-naphthyl); heteroaryl (e.g., pyridyl, thienyl, and furanyl); carboxyl; $C_1$-$C_8$ alkoxycarbonyl (e.g., methoxycarbonyl, ethoxycarbonyl, 1-propyloxycarbonyl, 2-propyloxycarbonyl, and t-butoxycarbonyl); carbamoyl optionally substituted with lower alkyl (e.g., carbamoyl, methylaminocarbonyl, dimethylaminocarbonyl, and diethylaminocarbonyl); cyclic aminocarbonyl (e.g., pyrrolidinocarbonyl, piperidinocarbonyl, and morpholinocarbonyl); and the like. Examples of preferable substituents include methylamino, ethylamino, dimethylamino, diethylamino, methoxy, ethoxy, 2-propyloxy, t-butoxycarbonyl, hydroxyl, a fluorine atom, a chlorine atom, trifluoro, morpholino, piperidino, pyrrolidino, carboxyl, methoxycarbonyl, morpholinocarbonyl, phenyl, pyridyl, and the like. The optionally substituted lower alkoxy may be substituted with at least one substituent selected from the group consisting of the substituents mentioned above. The number of substituents may be, for example, 0, 1, 2, or 3, and preferably 0, 1, or 2.

In the present invention, the lower alkoxy of the "lower alkoxycarbonyl" is as defined above. The lower alkoxycarbonyl is a carbonyl group to which a lower alkoxy group, such as those mentioned above, is bound. Examples of the lower alkoxycarbonyl include $C_1$-$C_8$ alkoxycarbonyl containing a linear, branched, or cyclic structure. Specific examples of the linear or branched alkoxycarbonyl include methoxycarbonyl, ethoxycarbonyl, 1-propoxycarbonyl, 2-propoxycarbonyl, 1-butoxycarbonyl, 2-butoxycarbonyl, isobutoxycarbonyl, t-butoxycarbonyl, and the like. Examples of the $C_1$-$C_8$ alkoxycarbonyl containing a cyclic structure include cyclopropoxycarbonyl, cyclopropylmethoxycarbonyl, cyclobutyloxycarbonyl, cyclobutylmethoxycarbonyl, cyclopentyloxycarbonyl, cyclopentylmethoxycarbonyl, cyclohexyloxycarbonyl, cyclohexylmethoxycarbonyl, cyclohexylethoxycarbonyl, and the like. Preferable examples of the lower alkoxycarbonyl include methoxycarbonyl, ethoxycarbonyl, 2-propoxycarbonyl, cyclopropoxycarbonyl, and the like.

In the present invention, the lower alkyl of the "lower alkylsulfonyl" is as defined above. The lower alkysulfonyl is a sulfonyl group to which a lower alkyl group, such as those mentioned above, is bound. Examples of the lower alkylsulfonyl include $C_1$-$C_8$ alkylsulfonyl containing a linear, branched, or cyclic structure. Specific examples of the linear or branched alkylsulfonyl include methanesulfonyl, ethanesulfonyl, 1-propylsulfonyl, 2-propylsulfonyl, 1-butylsulfonyl, 2-butylsulfonyl, isobutylsulfonyl, t-butylsulfonyl, and the like. Examples of the $C_1$-$C_8$ alkylsulfonyl containing a cyclic structure include cyclopropylsulfonyl, cyclopropylmethylsulfonyl, cyclobutylsulfonyl, cyclobutylmethylsulfonyl, cyclopentylsulfonyl, cyclopentylmethylsulfonyl, cyclohexylsulfonyl, cyclohexylmethylsulfonyl, cyclohexylethylsulfonyl, and the like. Preferable examples include methanesulfonyl, ethanesulfonyl, 2-propanesulfonyl, cyclopropanesulfonyl, and the like.

In the present invention, the lower alkyl and lower alkylsulfonyl of the "carbamoyl optionally substituted with lower alkyl or lower alkylsulfonyl" are as defined above. The carbamoyl optionally substituted with lower alkyl or lower alkylsulfonyl includes "carbamoyl optionally substituted with lower alkyl" and "carbamoyl optionally substituted with lower alkylsulfonyl."

The "carbamoyl optionally substituted with lower alkyl" is a carbamoyl group to which one or two lower alkyl groups, such as those mentioned above, may be bound. When two lower alkyl groups are bound, the lower alkyl groups may be the same or different. Examples of the carbamoyl optionally substituted with lower alkyl include carbamoyl; aminocarbonyl substituted with $C_1$-$C_8$ alkyl containing a linear, branched, or cyclic structure; and the like. Specific examples of the carbamoyl optionally substituted with lower alkyl include carbamoyl, methylaminocarbonyl, ethylaminocarbonyl, propylaminocarbonyl, 2-propylaminocarbonyl, dimethylaminocarbonyl, diethylaminocarbonyl, ethylmethylaminocarbonyl, methylpropylaminocarbonyl, dicyclohexylaminocarbonyl, and the like.

The "carbamoyl optionally substituted with lower alkylsulfonyl" is a carbamoyl group to which one or two lower alkylsulfonyl groups, such as those mentioned above, may be bound. When two lower alkylsulfonyl groups are bound, the lower alkylsulfonyl groups may be the same or different. Examples of the carbamoyl optionally substituted with lower alkylsulfonyl include carbamoyl; aminocarbonyl substituted with $C_1$-$C_8$ alkylsulfonyl containing a linear, branched, or cyclic structure; and the like. Examples of the linear or branched $C_1$-$C_8$ alkylsulfonylaminocarbonyl include methanesulfonylaminocarbonyl, ethanesulfonylaminocarbonyl, 1-propylsulfonylaminocarbonyl, 2-propylsulfonylaminocarbonyl, 1-butylsulfonylaminocarbonyl, 2-butylsulfonylaminocarbonyl, isobutylsulfonylaminocarbonyl, t-butylsulfonylaminocarbonyl, and the like. Examples of the $C_1$-$C_8$ alkylsulfonylaminocarbonyl containing a cyclic structure include cyclopropylsulfonylaminocarbonyl, cyclopropylmethylsulfonylaminocarbonyl, cyclobutylsulfonylaminocarbonyl, cyclobutylmethylsulfonylaminocarbonyl, cyclopentylsulfonylaminocarbonyl, cyclopentylmethylsulfonylaminocarbonyl, cyclohexylsulfonylaminocarbonyl, cyclohexylmethylsulfonylaminocarbonyl, cyclohexylethylsulfonylaminocarbonyl, and the like. Preferable examples of the carbamoyl optionally substituted with lower alkylsulfonyl include carbamoyl, methanesulfonylaminocarbonyl, ethanesulfonylaminocarbonyl, 2-propylsulfonylaminocarbonyl, cyclopropylsulfonylaminocarbonyl, and the like.

In the present invention, the optionally substituted cyclic amino of the "optionally substituted cyclic aminocarbonyl" is as defined above. The optionally substituted cyclic aminocarbonyl is a carbonyl group to which an optionally substituted cyclic amino group, such as those mentioned above, is bound. Specific examples of the optionally substituted cyclic aminocarbonyl include pyrrolidinocarbonyl, piperidinocarbonyl, piperazinocarbonyl, 4-methylpiperidino, morpholinocarbonyl, 2-pyrrolidonylcarbonyl, and the like. Preferable examples are pyrrolidinocarbonyl, morpholinocarbonyl, and the like.

In the present invention, the lower alkyl of the "sulfamoyl optionally substituted with lower alkyl" is as defined above. The sulfamoyl optionally substituted with lower alkyl is a sulfamoyl group to which one or two lower alkyl groups, such as those mentioned above, may be bound. When two lower alkyl groups are bound, the lower alkyl groups may be the same or different. Examples of the sulfamoyl optionally substituted with lower alkyl include sulfamoyl; aminosulfonyl substituted with $C_1$-$C_8$ alkyl containing a linear, branched, or cyclic structure; and the like. Specific examples include sulfamoyl, methylaminosulfonyl, ethylaminosulfonyl, propylaminosulfonyl, 2-propylaminosulfonyl, dimethylaminophonyl, diethylaminosulfonyl, ethylmethylaminosulfonyl, methylpropylaminosulfonyl, dicyclohexylaminosulfonyl, and the like.

In the present invention, the optionally substituted cyclic amino of the "optionally substituted cyclic aminosulfonyl" is as defined above. The optionally substituted cyclic aminosulfonyl is a sulfonyl group to which an optionally substituted cyclic amino group, such as those mentioned above, is bound. Specific examples of the optionally substituted cyclic aminosulfonyl include pyrrolidinosulfonyl, piperidinosulfonyl, piperazinosulfonyl, 4-methylpiperidinosulfonyl, morpholinosulfonyl, 4-piperidonylsulfonyl, and the like. Preferable examples are pyrrolidinosulfonyl, morpholinosulfonyl, and the like.

In the present invention, when Y is a carbon atom, ------ is a single or double bond. When Y is a nitrogen atom, ------ is a single bond.

In the compound represented by formula (1), A is an optionally substituted benzene ring. Examples of the substituent for A include at least one member selected from the group consisting of the following A-1 to A-16. When two or more substituents are present, the substituents may be the same or different from each other.

A-1) halogen,
A-2) hydroxyl,
A-3) nitro,
A-4) cyano,

A-5) carboxyl,
A-6) optionally substituted amino,
A-7) optionally substituted cyclic amino,
A-8) optionally substituted lower alkyl,
A-9) optionally substituted lower alkoxy,
A-10) lower alkoxycarbonyl,
A-11) lower alkylsulfonyl,
A-12) carbamoyl optionally substituted with lower alkyl or lower alkylsulfonyl,
A-13) optionally substituted cyclic aminocarbonyl,
A-14) sulfamoyl optionally substituted with lower alkyl,
A-15) optionally substituted cyclic aminosulfonyl, and
A-16) tetrazolyl.

The number of substituents in A is, for example, 0 to 5, 0 to 4, 0 to 3, preferably 0, 1, or 2, and more preferably 0 or 1. When two or more substituents are present, the substituents may be the same or different from each other.

Other examples of substituents for A include at least one member selected from the group consisting of A-1 and A-3 to A-16 described above; at least one member selected from the group consisting of the above A-1 and A-3 to A-16 excluding methoxy; and the like.

The substituent for A is preferably at least one member selected from the group consisting of halogen; lower alkoxy; and optionally halogen-substituted lower alkyl, more preferably at least one member selected from the group consisting of halogen, methoxy, ethoxy, fluoromethyl, difluoromethyl, trifluoromethyl, fluoroethyl, difluoroethyl, and trifluoroethyl, and particularly preferably at least one member selected from the group consisting of a chlorine atom, a fluorine atom, and trifluoromethyl.

In the compound represented by formula (1), the substituent for A may be bound to any of the carbon atoms at 4-position, 5-position, 6-position, and 7-position of the benzisoxazole or benzisothiazole skeleton. Preferably, the substituent is bound to at least one of the carbon atoms at the 4-position, 5-position, and 6-position, more preferably to carbon atoms at the 4-position and/or 5-position, and particularly preferably to the carbon atom at the 4-position. In the present invention, the position numbers of the atoms constituting the benzisoxazole or benzisothiazole skeleton are as follows.

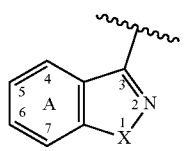

(wherein A and X are as defined above).

In the compound represented by formula (1), particularly preferable A is a benzene ring wherein halogen, lower alkoxy, or optionally halogen-substituted lower alkyl is bound to the carbon atom at the 4-position of the benzisoxazole or benzisothiazole skeleton, and carbon atoms at the 5-, 6-, and 7-positions are not substituted.

In the compound represented by formula (1), B is an optionally substituted aryl or an optionally substituted heteroaryl. The optionally substituted aryl or optionally substituted heteroaryl is as defined above. The aryl is, for example, phenyl or naphthyl, and is preferably phenyl. The heteroaryl is preferably a monocyclic nitrogen-containing heteroaryl that does not contain any other heteroatom as a ring-constituting atom, or benzoimidazolyl. The monocyclic nitrogen-containing heteroaryl that does not contain any other heteroatom as a ring-constituting atom is preferably a 5- or 6-membered heteroaryl containing one nitrogen atom as a ring-constituting heteroatom. Examples include pyrrolyl and pyridyl, preferably pyridyl, and more preferably 2-pyridyl. The benzimidazolyl is preferably benzimidazol-3-yl.

When B is monocyclic aryl, B may be substituted with at least one substituent selected from the group consisting of the following B-1 to B-16. When B is monocyclic or bicyclic heteroaryl, B may be substituted with at least one substituent selected from the group consisting of the following B-1 to B-17:

B-1) halogen,
B-2) hydroxyl,
B-3) nitro,
B-4) cyano,
B-5) carboxyl,
B-6) optionally substituted amino,
B-7) optionally substituted cyclic amino,
B-8) optionally substituted lower alkyl,
B-9) optionally substituted lower alkoxy,
B-10) lower alkoxycarbonyl,
B-11) lower alkylsulfonyl,
B-12) carbamoyl optionally substituted with lower alkyl or lower alkylsulfonyl,
B-13) optionally substituted cyclic aminocarbonyl,
B-14) sulfamoyl optionally substituted with lower alkyl,
B-15) optionally substituted cyclic aminosulfonyl,
B-16) tetrazolyl, and
B-17) oxo.

The number of substituents in B is, for example, 0 or at least 1, 0 to 5, 0 to 4, preferably 0 to 3, and more preferably 0, 1, or 2. When two or more substituents are present, the substituents may be the same or different from each other.

The substituent for B is, for example, at least one member selected from the group consisting of halogen; carboxyl; optionally substituted lower alkyl; lower alkoxycarbonyl; carbamoyl optionally substituted with lower alkyl or lower alkylsulfonyl; and optionally substituted cyclic aminocarbonyl. Specific examples include at least one member selected from the group consisting of halogen, carboxyl, methyl, ethyl, 1-propyl, 2-propyl, hydroxymethyl, carboxymethyl, trichloromethyl, trifluoromethyl, methoxycarbonyl, ethoxycarbonyl, t-butoxycarbonyl, methylaminocarbonyl, dimethylaminocarbonyl, ethylmethylaminocarbonyl, methanesulfonylaminocarbonyl, pyrrolidinocarbonyl, and morpholinocarbonyl. When B is aryl, examples of substituents include at least one member selected from the above group excluding oxo.

The substituent for B is at least one member selected from the group consisting of halogen; carboxyl; lower alkyl; halogen-substituted lower alkyl; lower alkoxycarbonyl; and carbamoyl optionally substituted with lower alkyl. Specific examples include at least one member selected from the group consisting of halogen, carboxyl, methyl, ethyl, trichloromethyl, trifluoromethyl, methoxycarbonyl, ethoxycarbonyl, n-propoxycarbonyl, isopropoxycarbonyl, monomethylaminocarbonyl, and dimethylaminocarbonyl.

Particularly preferable examples of substituents for B include at least one member selected from the group consisting of a chlorine atom, a fluorine atom, methyl, carboxyl, methoxycarbonyl, ethoxycarbonyl, methylaminocarbonyl, and dimethylaminocarbonyl.

In the compound represented by formula (1), when Y is a nitrogen atom, B is preferably an optionally substituted phenyl or an optionally substituted pyridyl. When Y is a carbon atom, B is preferably an optionally substituted phenyl, an optionally substituted pyridyl, or 2-oxobenzoimidazole-3-yl.

In the compound represented by formula (1), when B is substituted pyridyl or substituted phenyl, one or two carbon atoms, preferably one carbon atom, in the ortho-positions relative to the Y-bound carbon atom on the pyridine or benzene ring are preferably substituted. The substituent(s) bound to the carbon atom(s) in the ortho-position(s) may be any substituent for B. The substituent is preferably a halogen, more preferably a chlorine atom or a fluorine atom, and even more preferably a chlorine atom.

In the compound represented by formula (1), when B is substituted pyridyl or substituted phenyl, the carbon atom at para-position with respect to the Y-bound carbon atom on the pyridine or benzene ring is preferably unsubstituted or substituted with carboxyl.

Further, in the compound represented by formula (1), when B is substituted pyridyl or substituted phenyl, all the carbon atoms in the meta-positions with respect to the Y-bound carbon atom on the pyridine or benzene ring are preferably unsubstituted.

In the compound represented by formula (1), when B is substituted pyridyl or substituted phenyl, it is more preferable that one or two carbon atoms, more preferably one carbon atom, in the ortho-positions with respect to the Y-bound carbon atom on the pyridine or benzene ring are substituted with a chlorine atom or a fluorine atom, that carbon atoms in the meta-positions are unsubstituted, and that the carbon atom in the para-position is unsubstituted or substituted with carboxyl, methoxycarbonyl, or ethoxycarbonyl.

When Y is a nitrogen atom and B is substituted 2-pyridyl, it is particularly preferable that one of the carbon atoms in the ortho-positions with respect to the Y-bound carbon atom on the pyridine ring is substituted with a chlorine atom or a fluorine atom, that all the carbon atoms in the meta-positions are unsubstituted, and that the carbon atom in the para-position is unsubstituted or substituted with carboxyl.

When Y is a nitrogen atom and B is substituted phenyl, it is particularly preferable that one of the carbon atoms in the ortho-positions with respect to the Y-bound carbon atom on the benzene ring is substituted with a chlorine atom or a fluorine atom; and that all the other carbon atoms that constitute the phenyl are unsubstituted.

When Y is a carbon atom and B is substituted 2-pyridyl, it is particularly preferable that one of the carbon atoms in the ortho-positions with respect to the Y-bound carbon atom on the pyridine ring is substituted with a chlorine atom or a fluorine atom, that all the carbon atoms at meta-positions are unsubstituted, and that the carbon atom in the para-position is unsubstituted or substituted with carboxyl, methoxycarbonyl, or ethoxycarbonyl.

When Y is a carbon atom and B is phenyl, it is particularly preferable that one of the carbon atoms in the ortho-positions with respect to the Y-bound carbon atom on the pyridine ring is substituted with a chlorine atom or a fluorine atom, that all the carbon atoms at meta-positions are unsubstituted, and that the carbon atom in the para-position is unsubstituted or substituted with carboxyl, methoxycarbonyl, or ethoxycarbonyl.

In the compound represented by formula (1), X is an oxygen atom or a sulfur atom, and is preferably an oxygen atom.

In the compound represented by formula (1), Y is a nitrogen atom or a carbon atom, and is preferably a nitrogen atom.

In the compound represented by formula (1), Y is a nitrogen atom or a carbon atom, and is preferably a nitrogen atom.

When Y is a carbon atom, ------ is a single or double bond. When Y is a nitrogen atom, ------ is a single bond.

In the compound represented by formula (1), each $R^1$ independently represents lower alkyl, or two $R^1$s may be bound to each other to form a spiro ring or a crosslinked structure, or two $R^1$s may be bound to each other to form a saturated fused heterocycle together with nitrogen and carbon atoms constituting a ring containing Y.

When $R^1$ is lower alkyl, preferable examples of $R^1$ include linear or branched $C_1$-$C_3$ alkyl. $R^1$ is more preferably methyl or ethyl, and even more preferably methyl.

When two $R^1$s are bound to each other to form a spiro ring or a crosslinked structure, forming a spiro ring means that two $R^1$s are both bound to one of the carbon atoms constituting the ring containing Y in formula (1) and the two $R^1$s are bound to each other to form a ring together with the carbon atom.

When two $R^1$s are bound to each other to form a spiro ring or a crosslinked structure, forming a crosslinked structure means that one $R^1$ group each is bound to two of the carbon atoms constituting the ring containing Y in formula (1) and the $R^1$s are bound to each other.

Specific examples of the case in which two $R^1$s are bound to each other to form a spiro ring or a crosslinked structure include a case in which two $R^1$s are bound to each other to form methylene, dimethylene, trimethylene, or tetramethylene, thus forming a crosslinked structure, and a case in which two $R^1$s are bound to each other to form dimethylene or trimethylene, thus forming a spiro ring. A preferable example is a case in which two $R^1$s are bound to each other to form methylene, dimethylene, or trimethylene, thus forming a crosslinked structure. A crosslinked structure formed by dimethylene, which is represented by the following structural formula, is particularly preferable.

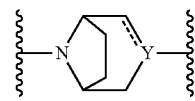

wherein Y and ------ are as defined above.

The phrase "two $R^1$s are bound to each other to form a saturated fused heterocycle together with nitrogen and carbon atoms constituting a ring containing Y" means that one $R^1$ each is bound to two adjacent carbon atoms among the carbon atoms that constitute a ring containing Y in formula (1) and the $R^1$s are bound to each other to form a saturated fused heterocycle together with nitrogen and carbon atoms constituting a ring containing Y. The saturated fused heterocycle referred to herein means a fused bicyclic ring of a heterocycle containing Y (a pyrazine ring or a piperidine ring) and a saturated carbon ring containing $R^1$.

Examples of the saturated fused heterocycle include a fused ring of a pyrazine ring or a piperidine ring and a cyclopentane ring or a cyclohexane ring. Specific examples of the saturated fused heterocycle include octahydrocyclopentapyridine, octahydrocyclopentapyrazine, decahydroquinoline, decahydroquinoxaline, and the like.

$R^1$ is preferably a crosslinked structure formed by $C_1$-$C_3$ alkyl or dimethylene, more preferably a crosslinked structure formed by methyl, ethyl, or dimethylene represented by the above structural formula.

In the compound represented by formula (1), p is 0, 1, or 2.

In the compound represented by formula (1), $(R^1)_p$ may be oxo.

Among the compounds represented by formula (1), salts thereof, or prodrugs thereof, the compound represented by the following formula (1A), a salt thereof, or a prodrug thereof is preferable. The compound represented by the following formula (1A), a salt thereof, and a prodrug thereof are also included within the scope of the present invention.

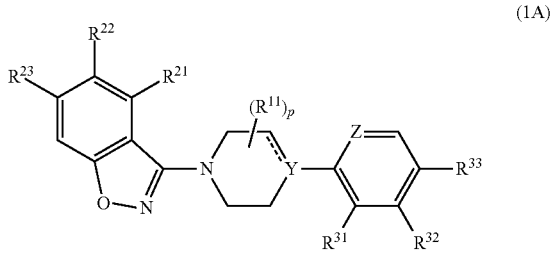

(1A)

(wherein Z is a nitrogen atom or CH;

Y is a nitrogen atom or a carbon atom;

------ of ------ Y is a single or double bond when Y is a carbon atom, or

------ of ------ Y is a single bond when Y is a nitrogen atom;

each $R^{11}$ independently represents methyl or ethyl, or two $R^{11}$s may be bound to each other to form a cross-linked structure by methylene, dimethylene, or trimethylene;

p is 0, 1, or 2; or $(R^{11})_p$ is oxo;

$R^{21}$, $R^{22}$, and $R^{23}$ independent represent a hydrogen atom, halogen, or trifluoromethyl;

$R^{31}$, $R^{32}$, and $R^{33}$ independently represent a hydrogen atom, halogen, halogen-substituted lower alkyl, methyl, carboxyl, lower alkoxycarbonyl, monomethylaminocarbonyl, or dimethylaminocarbonyl).

In the compound represented by formula (1A), Z is a nitrogen atom or CH. When Y is a nitrogen atom, Z is preferably a nitrogen atom.

In the compound represented by formula (1A), Y is a nitrogen atom or a carbon atom.

In the compound represented by formula (1A), each $R^{11}$ independently represents methyl or ethyl, or two $R^{11}$s are bound to each other to form a crosslinked structure by methylene, dimethylene, or trimethylene.

$R^{11}$ is preferably methyl or ethyl, or a crosslinked structure formed by dimethylene or trimethylene, and more preferably methyl or a crosslinked structure formed by diethylene.

The case in which two $R^{11}$s are bound to each other to form a crosslinked structure by methylene, dimethylene, or trimethylene refers to a case in which one $R^{11}$ each is bound to two of the carbon atoms that constitute the ring containing Y in formula (1A) and the $R^{11}$s are bound to each other to form methylene, dimethylene, or trimethylene, thus forming a crosslinked structure on the piperazine ring.

When the ring containing Y in formula (1A) is substituted with $R^{11}$, $(R^{11})_p$ is preferably oxo, or the ring is preferably represented by the following structural formula:

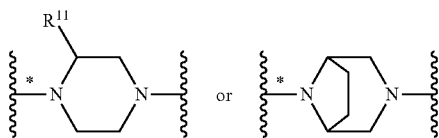

(wherein * represents the side bound to the carbon atom at the 3-position of isobenzoxazole, and $R^{111}$ represents $C_1$-$C_3$ alkyl). $R^{111}$ is preferably methyl or ethyl, and more preferably methyl.

In formula (1A), $(R^{11})_p$ may be oxo.

In the compound represented by formula (1A), $R^{21}$, $R^{22}$, and $R^{23}$ independently represent a hydrogen atom, halogen, or trifluoromethyl. $R^{21}$ is preferably halogen or trifluoromethyl, more preferably a chlorine atom or trifluoromethyl. $R^{22}$ is preferably a hydrogen atom, a chlorine atom, or trifluoromethyl, and more preferably a hydrogen atom. $R^{23}$ is preferably a hydrogen atom, a chlorine atom, or trifluoromethyl, and more preferably a hydrogen atom. It is particularly preferable that $R^{21}$ is halogen (preferably a chlorine atom or a fluorine atom) or trifluoromethyl, and that $R^{22}$ and $R^{23}$ are both a hydrogen atom.

In the compound represented by formula (1A), $R^{31}$, $R^{32}$, and $R^{33}$ independently represent a hydrogen atom, halogen, halogen-substituted lower alkyl, methyl, carboxyl, lower alkoxycarbonyl, monomethylaminocarbonyl, or dimethylaminocarbonyl. $R^{31}$ is preferably a hydrogen atom, halogen, trichloromethyl, trifluoromethyl, or methyl, and more preferably a chlorine atom. $R^{32}$ is preferably a hydrogen atom, halogen, or methyl, and more preferably a hydrogen atom. $R^{33}$ is preferably a hydrogen atom, halogen, carboxyl, methoxycarbonyl, ethoxycarbonyl, monomethylaminocarbonyl, or dimethylaminocarbonyl, more preferably a hydrogen atom, carboxyl, methoxycarbonyl, or ethoxycarbonyl, and particularly preferably a hydrogen atom or carboxyl.

Preferable examples of $R^{31}$, $R^{32}$, and $R^{33}$ are that $R^{31}$ is halogen (preferably a chlorine atom or a fluorine atom), $R^{32}$ is a hydrogen atom, and $R^{33}$ is a hydrogen atom or carboxyl. When $R^{21}$ is halogen (preferably a chlorine atom), it is preferable that $R^{31}$ is halogen (preferably a chlorine atom or a fluorine atom), $R^{32}$ is a hydrogen atom, and $R^{33}$ is a hydrogen atom. When $R^{21}$ is trihalomethyl (preferably trifluoromethyl), it is preferable that $R^{31}$ is halogen (preferably a chlorine atom or a fluorine atom), $R^{32}$ is a hydrogen atom, and $R^{33}$ is a hydrogen atom, carboxyl, methoxycarbonyl, or ethoxycarbonyl. It is also preferable that $R^{21}$ is a chlorine atom or trifluoromethyl, $R^{22}$ and $R^{23}$ are both a hydrogen atom, $R^{31}$ is a chlorine atom, $R^{32}$ is a hydrogen atom, and $R^{33}$ is a hydrogen atom or carboxyl.

Specific examples of the compound represented by formula (1), a salt thereof, or a prodrug thereof according to the present invention include Compound 011, Compound 021, Compound 031, Compound 041, Compound 051, Compound 061, Compound 071, Compound 081, Compound 091, Compound 101, Compound 111, Compound 121, Compound 131, Compound 141, Compound 151, Compound 161, Compound 171, Compound 181, Compound 191, Compound 201, Compound 211, Compound 221, Compound 231, Compound 241, Compound 251, Compound 261, Compound 271, Compound 281, Compound 291, Compound 301, Compound 311, Compound 321, Compound 331, Compound 341, Compound 351, Compound 361, Compound 371, Compound 381, Compound 391, and Compound 401. Preferable examples include the following compounds, salts thereof, and prodrugs thereof.

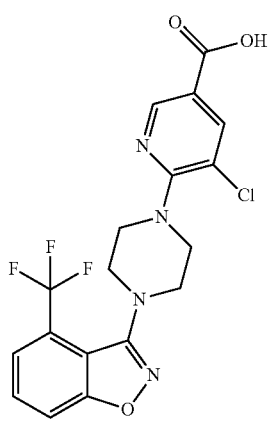
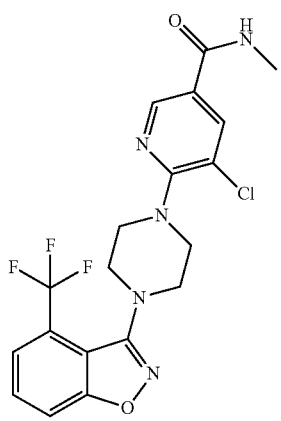
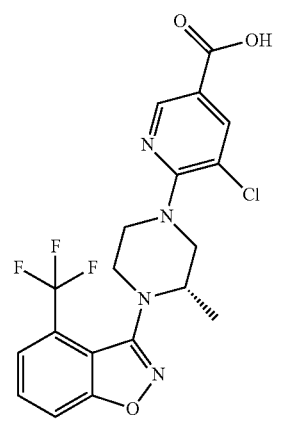
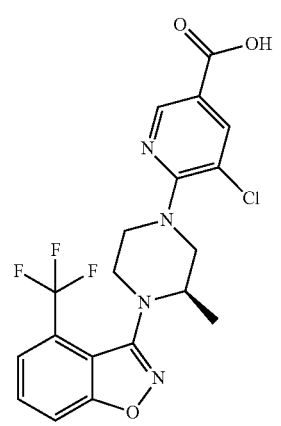
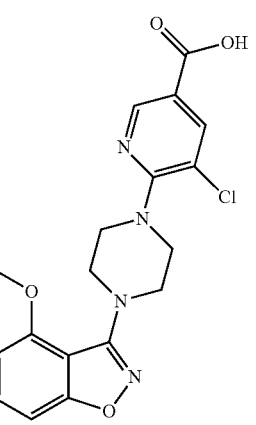
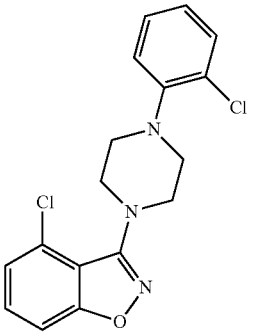
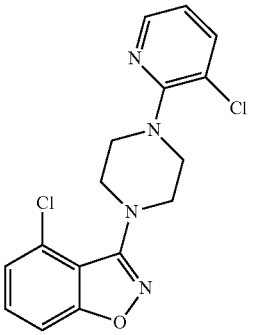
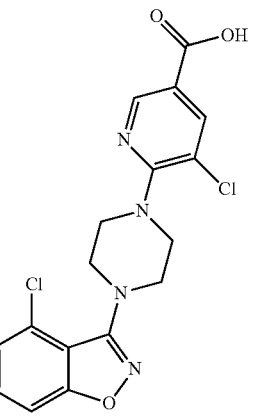

091
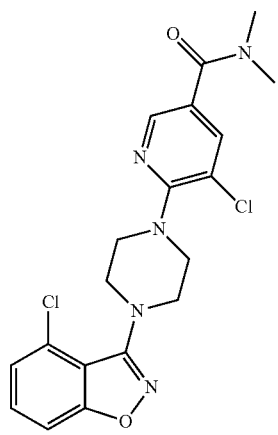
101
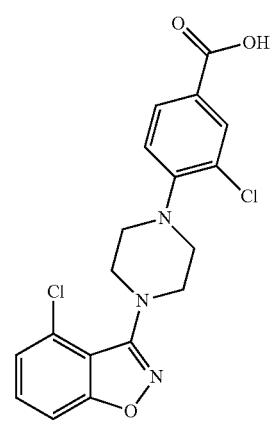
111
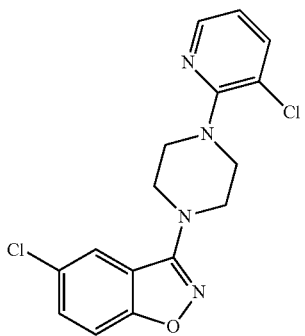
121
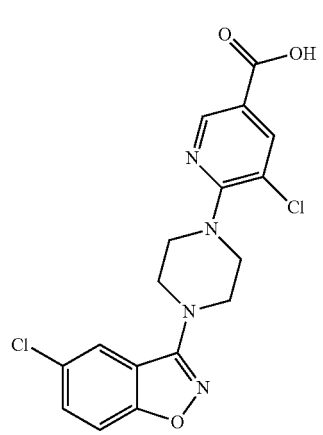
131
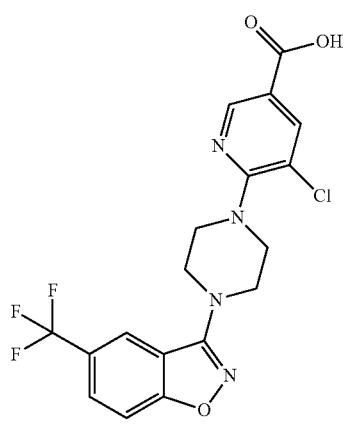
141
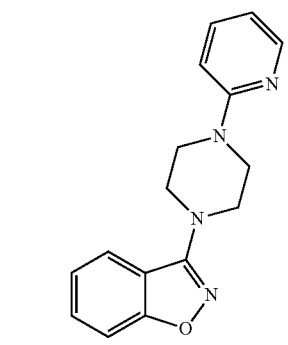
151
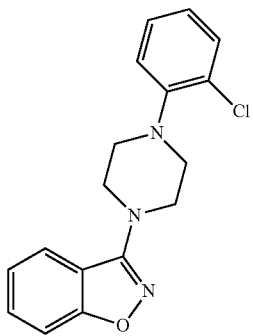
161
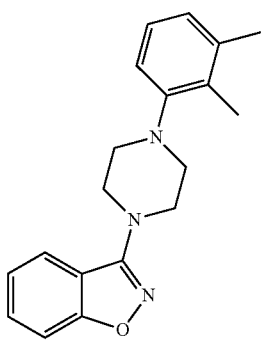

171 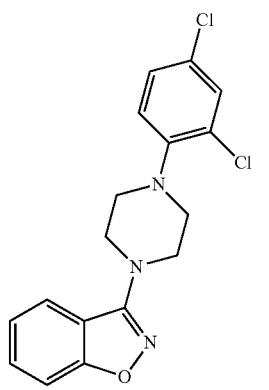
181 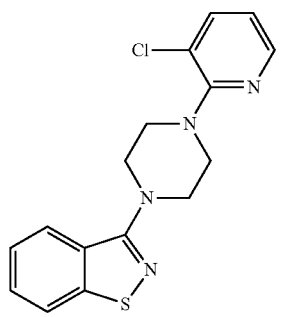
191 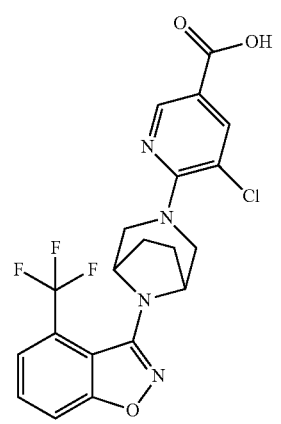
221 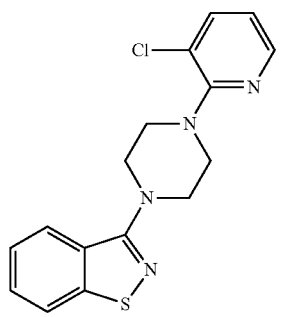
231 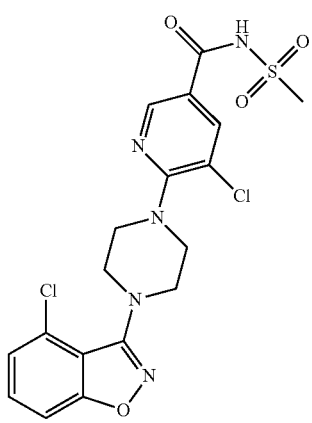
261 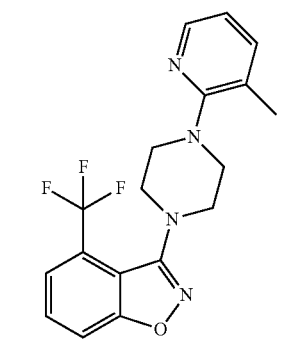
271 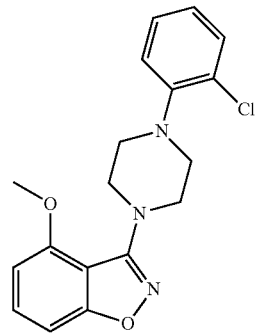
281 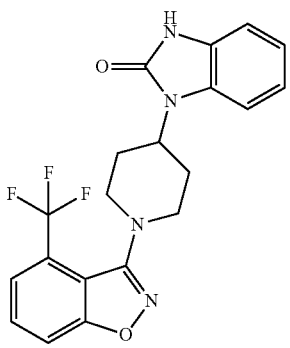

-continued
301
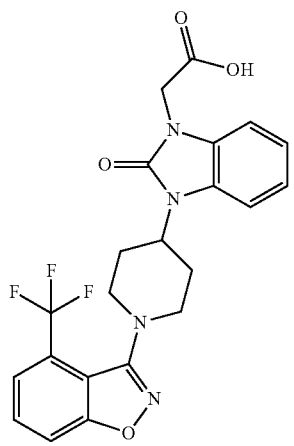
311
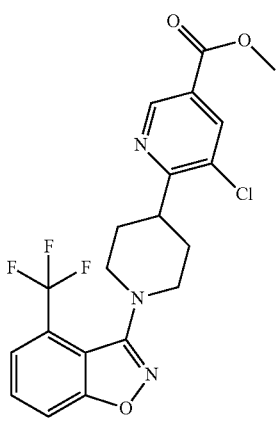
321
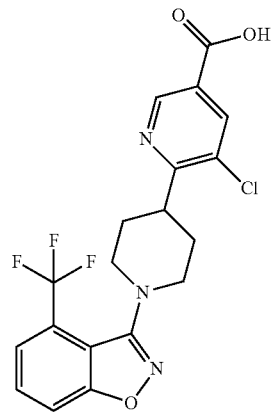
331
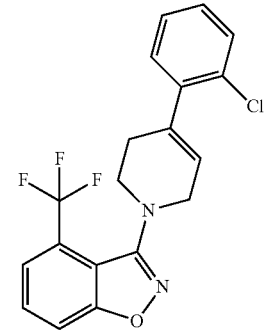
-continued
341
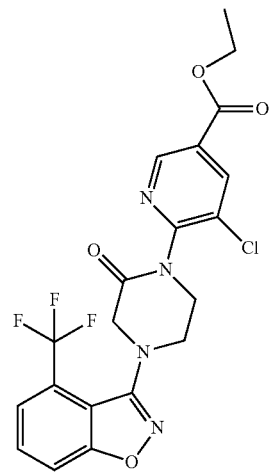
351
361
371

-continued

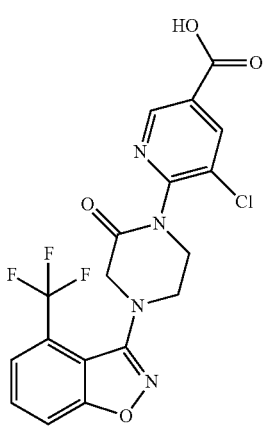

381

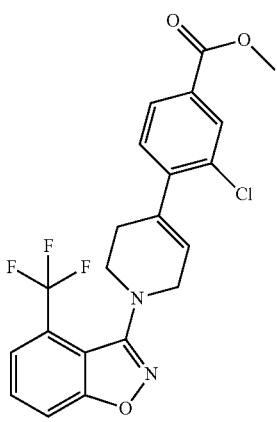

391

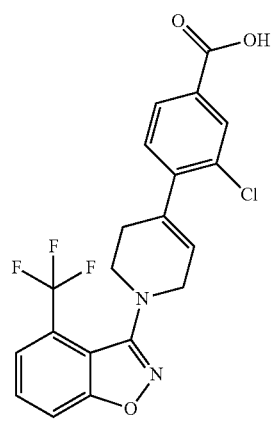

401

The compound represented by formula (1), a salt thereof, or a prodrug thereof according to the present invention is more preferably Compound 011, Compound 021, Compound 031, Compound 041, Compound 061, Compound 071, Compound 081, Compound 091, Compound 101, Compound 111, Compound 121, Compound 131, Compound 141, Compound 151, Compound 161, Compound 171, Compound 191, Compound 221, Compound 281, Compound 311, Compound 321, Compound 331, Compound 341, Compound 351, Compound 361, Compound 371, Compound 381, Compound 391, or Compound 401; a salt thereof; or a prodrug thereof. The compound represented by formula (1), a salt thereof, or a prodrug thereof is even more preferably Compound 011, Compound 021, Compound 031, Compound 041, Compound 061, Compound 071, Compound 081, Compound 091, Compound 101, Compound 111, Compound 121, Compound 131, Compound 141, Compound 151, Compound 161, Compound 171, Compound 191, Compound 321, Compound 351, Compound 361, Compound 371, Compound 381, or Compound 401; a salt thereof; or a prodrug thereof; and is particularly preferably Compound 011, Compound 031, Compound 041, Compound 061, Compound 071, Compound 191, Compound 361, Compound 371, Compound 381, or Compound 401; a salt thereof; or a prodrug thereof.

The present invention further includes a compound represented by the following formula (2), a salt thereof, or a prodrug thereof. The compound of formula (2), a salt thereof, or a prodrug thereof may have an activity of regulating or inhibiting the activity of TRPC channels, such as the TRPC3 channel and/or TRPC6 channel, preferably the TRPC6 channel. Further, the compound or a salt thereof can also be used as an intermediate for the compound represented by formula (1).

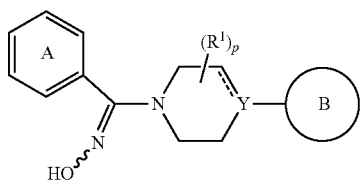
(2)

(wherein A, B, Y, $R^1$, P, and ----- are as defined above).

In the compound represented by formula (2), A, B, Y, $R^1$, P, and ----- are as defined above.

In formula (2), the bond between the nitrogen atom and the hydroxyl group is represented by a wavy line, which is a line indicated below. This line indicates that the compound represented by formula (2) may be any of E-isomer, Z-isomer, and a blend thereof, wherein the E-isomer and Z-isomer are geometric isomers that are present due to the partial structure >C=N—OH of the compound. The same applies to compounds other than the compound of formula (2) that include the wavy line.

Among the compounds represented by formula (2), salts thereof, or prodrugs thereof, the compound represented by the following formula (2A), a salt thereof, or a prodrug thereof is preferable. These are also included within the scope of the present invention.

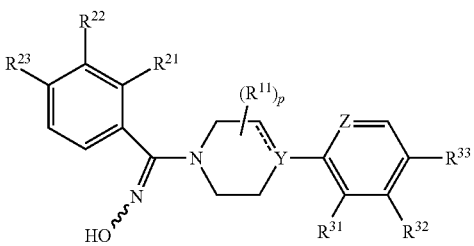
(2A)

wherein Z, Y, $R^{11}$, p, $R^{21}$, $R^{22}$, $R^{23}$, $R^{31}$, $R^{32}$, $R^{33}$, and ----- are as defined above.

In the compound represented by formula (2A), Y, $R^{11}$, p, $R^{21}$, $R^{22}$, $R^{23}$, $R^{31}$, $R^{32}$, $R^{33}$, and ----- are as defined above.

Among the compounds represented by formula (2), salts thereof, or prodrugs thereof, the compound represented by the following formula (2B), a salt thereof, or a prodrug thereof is preferable. These are also included within the scope of the present invention. The compound represented by formula (2B) or a salt thereof is also preferable as an intermediate for producing the compound represented by formula (1):

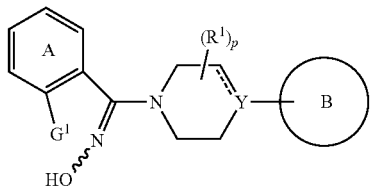

(2B)

(wherein, A, B, Y, R¹, p, and ------ are as defined above, and G¹ is halogen, optionally halogen-substituted lower alkylsulfonyl, or benzenesulfonyl optionally substituted with lower alkyl or nitro).

In formula (2B), A, B, Y, R¹, p, and ------ are as defined above. The compound represented by formula (2B) or a salt thereof includes E-isomer and Z-isomer, which are geometric isomers that are present due to the partial substructure >C=N—OH of the compound. When the compound represented by formula (2B) or a salt thereof is used as an intermediate compound for producing the compound represented by formula (1), the E-isomer is preferable.

Examples of the halogen represented by G¹ include a chlorine atom, a fluorine atom, a bromine atom, and an iodine atom.

The lower alkylsulfonyl of the optionally halogen-substituted lower alkylsulfonyl represented by G¹ is as defined above. The lower alkylsulfonyl is a sulfonyl group to which a lower alkyl group is bound. The lower alkyl may be substituted with halogen. Examples of the optionally halogen-substituted lower alkylsulfonyl include linear or branched $C_1$-$C_6$ alkyl (preferably $C_1$-$C_4$ alkyl, and more preferably $C_1$-$C_3$ alkyl) sulfonyl. Specific examples include methanesulfonyl, ethanesulfonyl, trifluoromethanesulfonyl, and the like.

Examples of the optionally lower-alkyl-substituted benzenesulfonyl represented by G¹ include benzenesulfonyl that may be substituted with one to three (preferably one or two, and more preferably one) linear or branched $C_1$-$C_6$ alkyl groups (preferably $C_1$-$C_4$ alkyl, and more preferably $C_1$-$C_3$ alkyl) groups. Specific examples include p-toluenesulfonyl and the like.

Examples of the optionally nitro-substituted benzenesulfonyl represented by G¹ include benzenesulfonyl that may be substituted with one to three (preferably one) nitro groups. Specific examples include o-nitrobenzenesulfonyl, p-nitrobenzenesulfonyl, and the like.

G¹ is preferably a chlorine atom, a fluorine atom, a bromine atom, methanesulfonyl, ethanesulfonyl, trifluoromethanesulfonyl, p-toluenesulfonyl, or p-nitrobenzenesulfonyl. G¹ is more preferably a chlorine atom or a bromine atom.

The compound represented by formula (2), a salt thereof, or a prodrug thereof according to the present invention includes, for example, the following compounds, salts thereof, or prodrugs thereof.

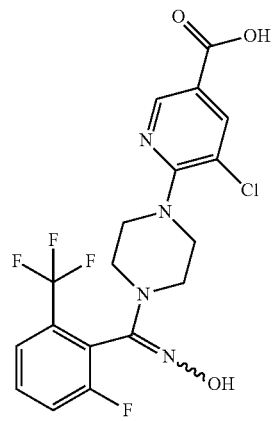

012

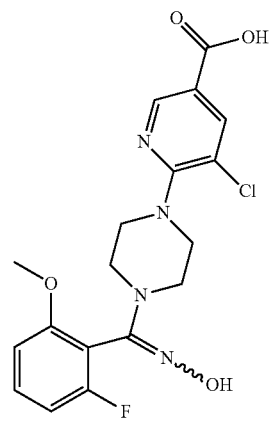

052

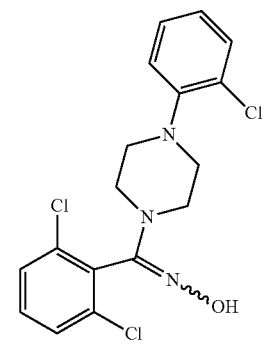

062

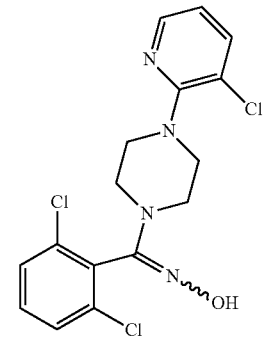

072

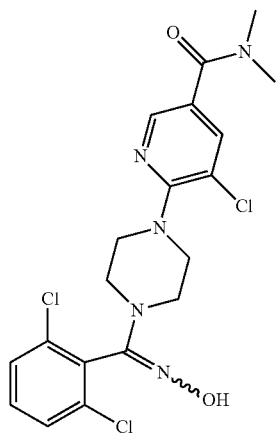
092
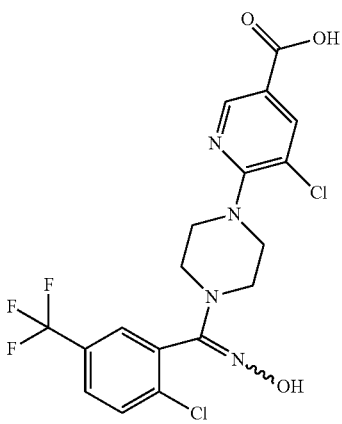
132
102
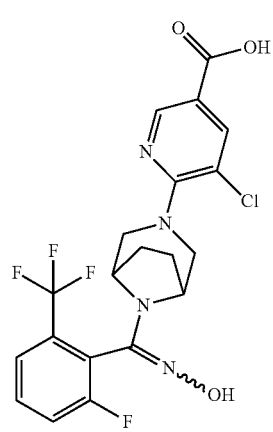
192
112
202
122
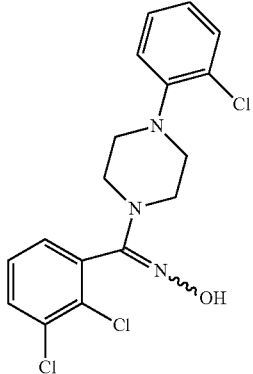
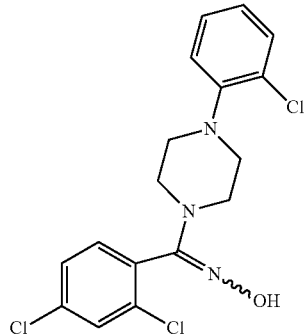
212

282

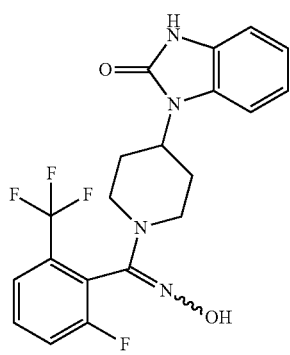

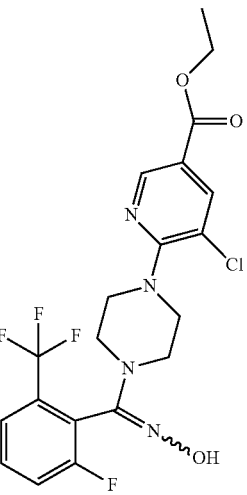
372

342

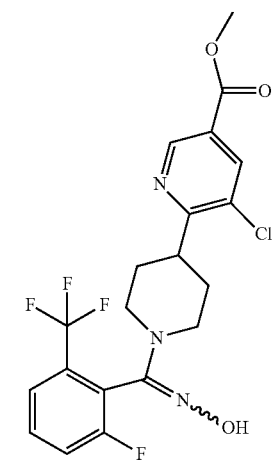

362

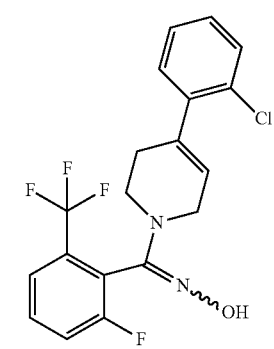

The compound represented by formula (2), a salt thereof, or a prodrug thereof according to the present invention is preferably Compound 062, Compound 202, Compound 362, or Compound 372; a salt thereof; or a prodrug thereof; and is more preferably (E)-isomer of Compound 202, (E)-isomer of Compound 362, (Z)-isomer of Compound 362, or (Z)-isomer of Compound 372; a salt thereof; or a prodrug thereof.

The compound of the present invention and the like can be produced, for example, by appropriate modification or a combination of any of the following: Production Methods 1 to 3 described below in detail; methods similar thereto; known methods; and the like. The compounds to be used as starting compounds may be used in the form of salts. The methods shown below are merely illustrative and other methods can also be used as appropriate based on the knowledge of people skilled in organic synthesis. When 1,2-benzisothiazole or a derivative thereof or 1,2-benzisoxazole or a derivative thereof that is not a commercial product is used as a starting compound, the compound can be produced and prepared with reference to the method disclosed in the following publication:

Advances in Heterocyclic Chemistry, *Heterocyclic Chemistry in the 21st Century: A Tribute to Alan Katritzky*, Elsevier, Cambridge (2017). R. A. Shastri, Review on Synthesis of 3-Substituted 1,2-Benzisoxazole Derivatives, Chem. Sci. Trans., 2016: 5; 8-20.

In each reaction for the production, functional groups can be protected as desired. With respect to the protecting groups and the technique of protection with protecting groups and deprotection, known methods, such as the method described in the following can be appropriately used: T. W. Greene and P. G. M. Wuts, *Protective Groups in Organic Synthesis*, 3rd Ed., John Wiley and Sons, Inc., New York (1999).

Production Method 1

In an embodiment, the compound represented by formula (1) can be produced by the synthesis scheme illustrated in the following Reaction Formula-1. Specifically, the compound represented by formula (1) can be produced from the compound represented by formula (3) and the compound represented by formula (4).

Reaction Formula-1

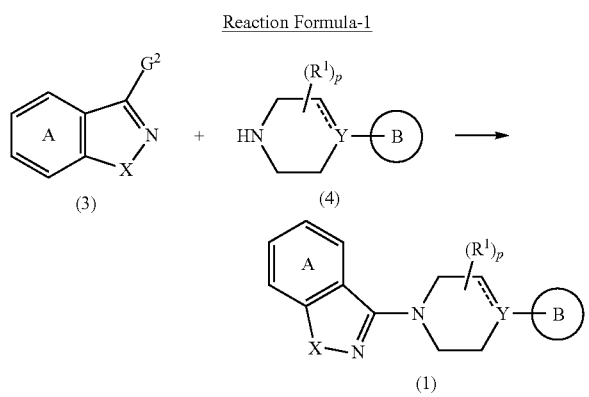

wherein A, B, Y, R$^1$, p, and ------ are as defined above; and G$^2$ represents a halogen, lower alkylsulfonyl optionally substituted with one or more halogens, or benzenesulfonyl optionally substituted with lower alkyl or nitro.

In Reaction Formula-1, A, B, Y, R$^1$, p, and ------ are as defined above.

Examples of halogens represented by G$^2$ include a chlorine atom, a fluorine atom, a bromine atom, and an iodine atom.

"Lower alkyl" in the lower alkylsulfonyl optionally substituted with one or more halogens represented by G$^2$ is as defined above. The lower alkylsulfonyl is a group in which lower alkyl is bound to sulfonyl, and the lower alkyl may optionally be substituted with one or more halogens. Examples of lower alkylsulfonyl optionally substituted with one or more halogens include linear or branched C1-C6 alkyl (preferably C1-C4 alkyl, more preferably C1-C3 alkyl) sulfonyl optionally substituted with 1 to 3 halogens, specifically, methanesulfonyl, ethanesulfonyl, and trifluoromethanesulfonyl.

Examples of benzenesulfonyl optionally substituted with lower alkyl represented by G$^2$ include benzenesulfonyl optionally substituted with 1 to 3 linear or branched C1-C6 alkyl groups (preferably C1-C4 alkyl, more preferably C1-C3 alkyl), and specifically, p-toluenesulfonyl.

Examples of benzenesulfonyl optionally substituted with nitro represented by G$^2$ include benzenesulfonyl optionally substituted with 1 to 3 (preferably 1) nitro groups, specifically, o-nitrobenzenesulfonyl and p-nitrobenzenesulfonyl.

G$^2$ is preferably a chlorine atom, a fluorine atom, a bromine atom, methanesulfonyl, ethanesulfonyl, trifluoromethanesulfonyl, p-toluenesulfonyl, or p-nitrobenzenesulfonyl.

The reaction of the compound represented by formula (3) with the compound represented by formula (4) can be performed, for example, in an inert solvent in the presence or absence of a base. An activating reagent may optionally be further added to the reaction system. The compound represented by formula (3) and the compound represented by formula (4) are known compounds and can be produced by a known method.

Examples of inert solvents include ether solvents, such as diethyl ether, tetrahydrofuran (THF), dioxane, and dimethoxymethane; aromatic hydrocarbon solvents, such as toluene, benzene, and xylene; halogenated hydrocarbon solvents, such as dichloromethane, chloroform, dichloroethane, and carbon tetrachloride; ketone solvents, such as acetone; aprotic solvents, such as dimethylsulfoxide, N,N-dimethylformamide (DMF), and acetonitrile; and pyridine. These solvents may also be used in a combination of two or more of suitable proportions.

Examples of bases include metal hydrides, such as sodium hydride and potassium hydride; metal hydroxides, such as potassium hydroxide and sodium hydroxide; metal carbonates, such as potassium carbonate, potassium hydrogen carbonate, sodium carbonate, sodium hydrogen carbonate, and cesium carbonate; alkyl amines, such as triethylamine and ethyldiisopropylamine; and metal alkoxides, such as sodium methoxide and potassium t-butoxide.

The amount of the base for use is typically 1 mol or more, preferably 1 to 5 mol, and more preferably 1 to 2 mol, per mol of the compound represented by formula (4).

The amount of the compound represented by formula (3) for use is typically 0.2 mol or more, preferably 0.2 to 2 mol, and more preferably 0.2 to 1.5 mol, per mol of the compound represented by formula (4).

The reaction temperature is typically −50° C. to 180° C., preferably −30° C. to 180° C., and more preferably −10° C. to 180° C. Microwaves may be used for facilitating the reaction, and the reaction temperature in this case is, for example, 80° C. to 180° C., and preferably 100° C. to 180° C. The reaction time is typically 10 minutes to 48 hours, and preferably 10 minutes to 24 hours.

Production Method 2

In an embodiment, the compound represented by formula (1B) can be produced by the synthesis scheme illustrated in the following Reaction Formula-2. Specifically, the compound represented by formula (1B) can be produced from the compound represented by formula (5) and the compound represented by formula (6).

Reaction Formula-2

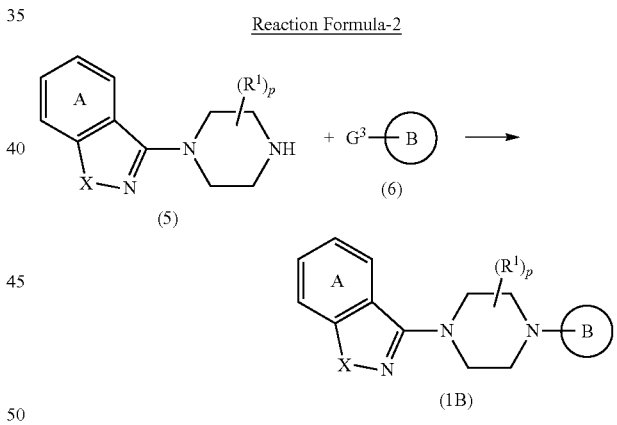

wherein A, B, X, R$^1$, and p are as defined above, and G$^3$ represents a halogen, lower alkylsulfonyl optionally substituted with one or more halogens, or benzenesulfonyl optionally substituted with lower alkyl or nitro.

In Reaction Formula-2, A, B, X, R$^1$, and p are as defined above.

Examples of halogens represented by G$^3$ include a chlorine atom, a fluorine atom, a bromine atom, and an iodine atom.

"Lower alkyl" in the lower alkylsulfonyl optionally substituted with one or more halogens represented by G$^3$ is as defined above. The lower alkylsulfonyl is a group in which lower alkyl is bound to sulfonyl, and the lower alkyl may be optionally substituted with one or more halogens. Examples of lower alkylsulfonyl optionally substituted with one or more halogens include linear or branched C1-C6 alkyl (preferably C1-C4 alkyl, more preferably C1-C3 alkyl) sulfonyl optionally substituted with 1 to 3 halogens, specifically, methanesulfonyl, ethanesulfonyl, and trifluoromethanesulfonyl.

Examples of benzenesulfonyl optionally substituted with lower alkyl represented by $G^3$ include benzenesulfonyl optionally substituted with 1 to 3 linear or branched C1-C6 alkyl groups (preferably C1-C4 alkyl, more preferably C1-C3 alkyl), and specifically, p-toluenesulfonyl.

Examples of benzenesulfonyl optionally substituted with nitro represented by $G^3$ include benzenesulfonyl optionally substituted with 1 to 3 (preferably 1) nitro groups, specifically, o-nitrobenzenesulfonyl and p-nitrobenzenesulfonyl.

$G^3$ is preferably a chlorine atom, a fluorine atom, a bromine atom, methanesulfonyl, ethanesulfonyl, trifluoromethanesulfonyl, p-toluenesulfonyl, or p-nitrobenzenesulfonyl.

The compound represented by formula (1B) can be obtained by coupling the compound represented by formula (5) with the compound represented by formula (6). The compound represented by formula (5) and the compound represented by formula (6) are known compounds and can be produced by a known method.

This reaction can be performed, for example, in an inert solvent in the presence of a base.

Examples of inert solvents include ether solvents, such as diethyl ether, tetrahydrofuran (THF), dioxane, and dimethoxymethane; aromatic hydrocarbon solvents, such as toluene, benzene, and xylene; halogenated hydrocarbon solvents, such as dichloromethane, chloroform, dichloroethane, and carbon tetrachloride; ketone solvents, such as acetone; aprotic solvents, such as dimethylsulfoxide, N,N-dimethylformamide (DMF), and acetonitrile; and pyridine. These solvents may be used in a combination of two or more of suitable proportions.

Examples of bases include metal hydrides, such as sodium hydride and potassium hydride; metal hydroxides, such as potassium hydroxide and sodium hydroxide; metal carbonates, such as potassium carbonate, potassium hydrogen carbonate, sodium carbonate, sodium hydrogen carbonate, and cesium carbonate; alkyl amines, such as triethylamine and ethyldiisopropylamine; and metal alkoxides, such as sodium methoxide and potassium t-butoxide.

The amount of the compound represented by formula (6) is typically 0.5 mol or more, further 1 mol or more, preferably 0.9 to 2 mol, and more preferably 0.9 to 1.5 mol, per mol of the compound represented by formula (5).

The amount of the base for use is typically 1 mol or more, preferably 1 to 5 mol, and more preferably 1 to 2 mol, per mol of the compound represented by formula (5).

The reaction temperature is typically 30° C. to a temperature higher than the boiling point of the solvent by 10° C., and preferably 80° C. to a temperature higher than the boiling point of the solvent by 10° C. To facilitate the reaction, microwaves may be used. In this case, the reaction temperature is, for example, 80° C. to 180° C., and preferably 100° C. to 180° C. The reaction time is typically 10 minutes to 48 hours, and preferably 10 minutes to 24 hours.

Additionally, the reaction of the compound represented by formula (5) with the compound represented by formula (6) can be performed by using the Buchwald reaction. For example, in the presence of a palladium catalyst, a phosphine ligand, and a base, the compound represented by formula (5) is reacted with the compound represented by formula (6) in a solvent.

Examples of palladium catalysts include divalent palladium catalysts, such as Pd(OAc)$_2$, PdCl$_2$, allyl palladium(II) chloride (dimer), bis(acetonitrile)palladium(II) dichloride, and bis(benzonitrile)palladium(II) dichloride; and zerovalent palladium catalysts, such as Pd$_2$(dba)$_3$(tris(dibenzylideneacetone) dipalladium(0)), bis(dibenzylideneacetone) palladium(0), and palladium carbon (Pd/C).

Examples of phosphine ligands include bidentate phosphine ligands, such as BINAP((2,2'-bis(diphenylphosphanyl)-1,1'-bisnaphthalene) and Xphos(2-dicyclohexylphosphino-2',4',6'-triisopropylbiphenyl).

Examples of bases include strong bases, such as t-BuONa (tert-butoxysodium).

The amount of the compound represented by formula (6) for use in this reaction is typically 0.5 mol or more, further 1 mol or more, preferably 0.9 to 2 mol, more preferably 1 to 1.5 mol, per mol of the compound represented by formula (5).

The amount of the palladium catalyst for use is typically 0.005 to 1 mol, and preferably 0.01 to 0.2 mol, per mol of the compound represented by formula (5).

The amount of the phosphine ligand for use is typically 0.5 to 5 mol, and preferably 1 to 2 mol, per mol of the palladium catalyst.

The amount of the base for use is typically 0.5 mol or more, further 1 mol or more, and preferably 1 to 2 mol, per mol of the compound represented by formula (5).

The reaction temperature is typically 40° C. to 150° C., and preferably 80° C. to 110° C. The reaction time is typically 1 to 24 hours, and preferably 3 to 12 hours.

Production Method 3

In an embodiment, the compound represented by formula (1) or (2) can be produced by the synthesis scheme illustrated in the following Reaction Formula-3. Specifically, the compound represented by formula (1C) can be produced by converting the compound represented by formula (7) into the compound represented by formula (8), reacting the compound represented by formula (8) with the compound represented by formula (4) to produce the oxime compound represented by formula (2B), and ring-closing the oxime compound represented by formula (2B). A person skilled in the art would be able to understand that the compound represented by formula (2) can be produced by using an appropriate, corresponding compound that has an optionally substituted benzene ring A, instead of the compound represented by formula (7) or (8), in the reaction illustrated in Reaction Formula-3. The compound represented by formula (7) is a known compound and can be produced by a known method.

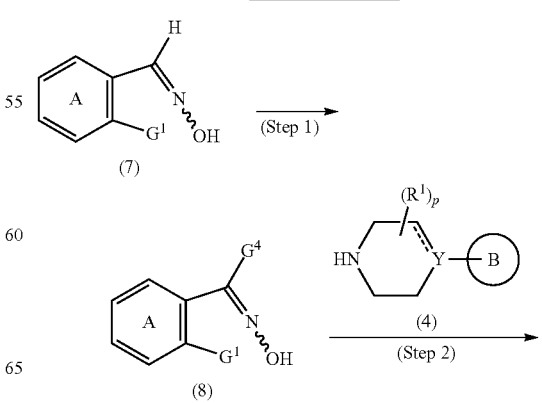

Reaction Formula-3

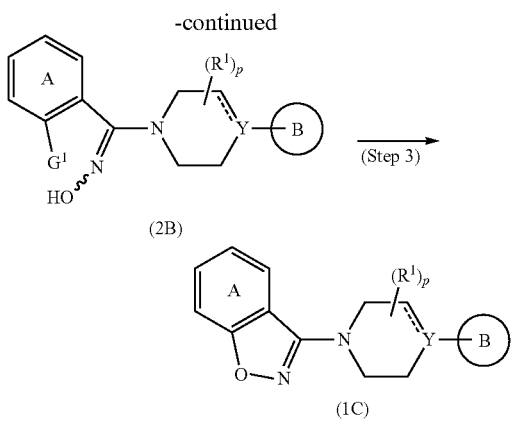

wherein A, B, Y, R¹, p, G¹, and ----- are as defined above; and G⁴ represents a halogen.

In Reaction Formula-3, A, B, Y, R¹, p, G¹, and ----- are as defined above.

Examples of halogens represented by G⁴ include a chlorine atom, a fluorine atom, a bromine atom, and an iodine atom.

Step 1 (i.e., the step of converting the compound represented by formula (7) into the compound represented by formula (8)) can be performed, for example, by reacting the compound represented by formula (7) with a halogenating agent in an inert solvent.

Examples of inert solvents for use in this reaction include ether solvents, such as diethyl ether, tetrahydrofuran (THF), dioxane, and dimethoxymethane; aromatic hydrocarbon solvents, such as toluene, benzene, and xylene; halogenated hydrocarbon solvents, such as dichloromethane, chloroform, dichloroethane, and carbon tetrachloride; ketone solvents, such as acetone; aprotic solvents, such as dimethylsulfoxide, N,N-dimethylformamide (DMF), and acetonitrile; and pyridine. These solvents may be used in a combination of two or more of appropriate proportions.

Examples of halogenating agents include typical halogenating agents, such as N-bromosuccinimide and N-chlorosuccinimide.

The amount of the halogenating agent for use is typically an equimolar amount to an excess molar amount, preferably 1- to 5-fold mol, and more preferably 1- to 2-fold mol, based on the compound represented by formula (7).

The reaction temperature is typically −30 to 150° C., preferably −10 to 100° C., and more preferably −10 to 40° C. The reaction time is typically 10 minutes to 48 hours, preferably 10 minutes to 24 hours, and more preferably 30 minutes to 18 hours.

Step 2 (i.e., the step of reacting the compound represented by formula (8) with the compound represented by formula (4) to synthesize the compound represented by formula (2B)) can be performed, for example, in an inert solvent in the presence of a base.

Examples of inert solvents for use in this reaction include ether solvents, such as diethyl ether, tetrahydrofuran (THF), dioxane, and dimethoxymethane; aromatic hydrocarbon solvents, such as toluene, benzene, and xylene; halogenated hydrocarbon solvents, such as dichloromethane, chloroform, dichloroethane, and carbon tetrachloride; ketone solvents, such as acetone; aprotic solvents, such as dimethylsulfoxide, N,N-dimethylformamide (DMF), and acetonitrile; and pyridine. These solvents may be used in a combination of two or more of appropriate proportions.

Examples of bases include metal hydrides, such as sodium hydride and potassium hydride; metal hydroxides, such as potassium hydroxide and sodium hydroxide; metal carbonates, such as potassium carbonate, potassium hydrogen carbonate, sodium carbonate, sodium hydrogen carbonate, and cesium carbonate; alkyl amines, such as triethylamine and ethyldiisopropylamine; and metal alkoxides, such as sodium methoxide and potassium t-butoxide.

The amount of the compound represented by formula (8) for use is typically 0.5 mol or more, 0.8 mol or more, preferably 0.9 to 2 mol, and more preferably 0.9 to 1.5 mol, per mol of the compound represented by formula (4).

The amount of the base for use is typically 1 mol or more, preferably 1- to 5-fold mol, and more preferably 1- to 2-fold mol, per mol of the compound represented by formula (4).

The reaction temperature is typically −20° C. to a temperature higher than the boiling point of the solvent by 10° C., and preferably 0° C. to 40° C. The reaction time is typically 10 minutes to 48 hours, preferably 10 minutes to 24 hours, and more preferably 30 minutes to 18 hours.

Step 3 (i.e., the step of ring-closing the compound represented by formula (2B) to convert the compound represented by formula (2B) into the compound represented by formula (1)) can be performed, for example, in an inert solvent in the presence of a base.

The compound represented by formula (2B) exists in both forms of (E)-isomer and (Z)-isomer, which are geometric isomers. From the standpoint of less heating required in the ring-closing reaction, (E)-isomer is preferable.

Examples of inert solvents for use in this reaction include ether solvents, such as diethyl ether, tetrahydrofuran (THF), dioxane, and dimethoxymethane; aromatic hydrocarbon solvents, such as toluene, benzene, and xylene; halogenated hydrocarbon solvents, such as dichloromethane, chloroform, dichloroethane, and carbon tetrachloride; ketone solvents, such as acetone; aprotic solvents, such as dimethylsulfoxide, N,N-dimethylformamide (DMF), and acetonitrile; and pyridine. These solvents may be used in a combination of two or more of appropriate proportions.

Examples of bases include metal hydrides, such as sodium hydride and potassium hydride; metal hydroxides, such as potassium hydroxide and sodium hydroxide; metal carbonates, such as potassium carbonate, potassium hydrogen carbonate, sodium carbonate, sodium hydrogen carbonate, and cesium carbonate; alkyl amines, such as triethylamine and ethyldiisopropylamine; and metal alkoxides, such as sodium methoxide and potassium t-butoxide.

The amount of the base for use is typically 1 mol or more, preferably 1- to 5-fold mol, and more preferably 1- to 2-fold mol, per mol of the compound represented by formula (2B).

The reaction temperature is typically 50° C. to a temperature higher than the boiling point of the solvent by 10° C., and preferably 80° C. to a temperature higher than the boiling point of the solvent by 10° C. To facilitate the reaction, microwaves may be used. In this case, the reaction temperature is, for example 80° C. to 180° C., and preferably 100° C. to 180° C. The reaction time is typically 10 minutes to 8 hours, and preferably 10 minutes to 2 hours.

The compound represented by formula (1) or (2) according to the present invention, intermediate compounds thereof, and starting material compounds thereof can be produced by the production methods described above, and can also be produced with reference to an already-known or publicly known technique at the time the present application was filed (e.g., B. R. Kiran et al., SYNTHESIS, EVALUATION OF ANALGESIC AND ANTI-INFLAMMATORY ACTIVITIES OF SUBSTITUTED 1,2-BENZOXA- ZOLONE AND 3-CHLORO-1,2-BENZOXAZOLE DERIVATIVES, International Journal of Pharmaceutical Sciences and Research, 2015; 6: 2918-2925) in accordance with the synthesis methods disclosed in the Examples of the present specification.

The functional groups of the starting material compounds and intermediate compounds illustrated in the reaction schemes above may optionally be protected by an appropriate protective group, using a known method, before the compounds are subjected to a reaction, and be deprotected using a known method after completion of the reaction.

The target compounds obtained in accordance with the reaction schemes above can be isolated and purified. For example, after the reaction mixture is cooled, the crude reaction product is subjected to isolation procedures, such as filtration, concentration, and extraction, in order to separate the crude reaction product; the crude reaction product is then subjected to typical purification procedures, such as column chromatography and recrystallization, thereby isolating and purifying a target compound from the reaction mixture.

The starting material compounds and the compound represented by formula (1) or (2) illustrated in the reaction schemes above include compounds in the form of solvate in which a solvent is added (e.g., a hydrate and solvate of ethanol).

When the compound represented by formula (1) or (2), the intermediate compounds obtained in the reaction schemes, or the starting material compounds have isomers, the compound represented by formula (1) or (2), the intermediate compounds obtained in the reaction schemes, or the starting material compounds include all of these isomers. The isomers include an isomer due to a double bond, a ring, or a fused ring (an E-, Z-, sis-, or trans-form); an isomer, for example, due to the presence of an asymmetric carbon (an R or S-form, α or β-form, enantiomer, or diastereomer); an optically active form that exhibits optical rotations (a D-, L-, d-, or l-form); a polar form due to chromatographic separation (a high polar form and low polar form); an equilibrium compound; a rotamer; a mixture thereof of any proportions; and a racemic mixture (isomers such as a geometric isomer, a stereoisomer, and an optical isomer). For example, optical isomers can be separated by using various known optical resolution methods (e.g., optical resolution by crystallization and direct optical resolution by chromatography).

The salt of the compound represented by formula (1) or (2) includes all pharmaceutically acceptable salts. The pharmaceutically acceptable salt can be any pharmaceutically acceptable salt. Examples include alkali metal salts, such as sodium salts and potassium salts; alkaline-earth metal salts, such as calcium salts and magnesium salts; inorganic metal salts, such as zinc salts; organic base salts, such as triethylamine, triethanolamine, trihydroxymethyl amino methane, and amino acid; inorganic acid salts, such as hydrochloride, hydrobromate, sulfate, phosphate, and nitrate; and organic acid salts, such as acetate, carbonate, propionate, succinate, lactate, malate, tartrate, citrate, maleate, fumarate, methanesulfonate, p-toluenesulfonate, benzenesulfonate, and ascorbate. These salts can be produced in accordance with an ordinary method.

The variety of isomers can be isolated by a known separation method. For example, racemates can be led to sterically pure isomers by a typical optical resolution method (e.g., optical resolution by crystallization and direct optical resolution by chromatography). An optically active compound can be produced by using a suitable, optically active starting material.

The starting material compounds, intermediate compounds, and target compounds described in the reaction schemes above can be used in their suitable salt form.

In the compound of the present invention and the like, one or multiple atoms may be replaced by one or multiple isotopes. Examples of isotopes include deuterium (2H), tritium (3H), 13C, 14N, and 18O.

The present invention includes a pharmaceutical composition containing the compound represented by formula (1) or (2), a salt thereof, or a prodrug thereof. The pharmaceutical composition according to the present invention is a preparation of the compound according to the present invention, a salt thereof, or a prodrug thereof in a typical pharmaceutical composition form, and is prepared by using the compound according to the present invention, a salt thereof, or a prodrug thereof and a pharmaceutically acceptable carrier. Examples of carriers include diluents and excipients, such as typically used fillers, extenders, binders, moisturizing agents, disintegrators, surfactants, and lubricants.

The prodrug according to the present invention refers to a compound that is converted into the compound according to the present invention through a reaction in vivo (e.g., an enzyme reaction and a reaction caused by stomach acid). For example, when the compound according to the present invention has carboxyl, the prodrug is a compound in which the carboxyl is converted into an ester. Examples of esters include methyl ester, ethyl ester, 1-propyl ester, 2-propyl ester, pivaloyloxy methyl ester, acetyloxymethyl ester, cyclohexyl acetyloxymethyl ester, 1-methyl cyclohexyl carbonyloxy methyl ester, ethyloxy carbonyloxy-1-ethyl ester, and cyclohexyloxy carbonyloxy-1-ethyl ester.

The pharmaceutical composition according to the present invention can be selected from various dosage forms according to the purpose of treatment. Typical examples include tablets, pills, powders, liquids, suspensions, emulsions, granules, capsules, suppositories, injectable drugs (e.g., liquids and suspensions), ointments, and inhalants.

The carrier for use in forming tablets can be selected from a wide range of known carriers. Examples include excipients, such as lactose, sucrose, sodium chloride, glucose, urea, starch, calcium carbonate, kaolin, and crystalline cellulose; binders, such as water, ethanol, propanol, simple syrup, a dextrose solution, a starch solution, a gelatin solution, methylcellulose, potassium phosphate, polyvinyl pyrrolidone, carboxy methylcellulose, and shellac; disintegrators, such as sodium alginate, dry starch, agar powder, laminaran powder, calcium carbonate, sodium hydrogen carbonate, a polyoxyethylene sorbitan fatty acid ester, sodium lauryl sulfate, stearic acid monoglyceride, starch, and lactose; sorbefacients, such as a quaternary ammonium base and sodium lauryl sulfate; disintegration inhibitors, such as stearin, cocoa butter, and hydrogenated oil; moisturizers, such as glycerol and starch; adsorbents, such as starch, lactose, kaolin, bentonite, and colloidal silica; and lubricants, such as purified talc, stearate, boric acid powder, and polyethylene glycol.

Tablets may further optionally be formed into tablets with typical coating, such as sugarcoated tablets, gelatin-coated tablets, enteric coating tablets, film coating tablets, double-layered tablets, or multi-layered tablets.

Carriers for use in preparing pills can be selected from a wide range of known carriers. Examples include excipients, such as glucose, lactose, starch, cacao oil, hydrogenated vegetable oil, kaolin, and talc; binders, such as powdered gum arabic, powdered tragacanth, gelatin, and ethanol; and disintegrators, such as laminaran and agar.

Carriers for use in preparing suppositories can be selected from a wide range of known carriers. Examples include polyethylene glycol, cacao oil, higher alcohols, esters of higher alcohols, gelatin, and semisynthetic glycerides.

When the pharmaceutical composition according to the present invention is prepared into an injectable drug, it is preferred that the liquid agent, emulsion, or suspension be sterilized and be isotonic with blood. Diluents for use in preparing the liquid agent, emulsion, and suspension can be selected from a wide range of known diluents. Examples include water, ethanol, propylene glycol, polyoxylated isostearyl alcohols, ethoxylated isostearyl alcohols, and polyoxyethylene sorbitan fatty acid esters. In the case of an injectable drug, the medical drug preparation can contain sodium chloride, glycerol, glucose, etc. in an amount sufficient to form an isotonic solution; and further can contain a typical solubilizing agent, a buffer, a soothing agent, etc., with further optionally a colorant, a preservative, an aroma component, a flavoring, a sweetener, and other medical drugs.

Ointments have forms such as a paste, cream, and gel. Examples of diluents for use in preparing an ointment of any of these forms include white petrolatum, paraffin, glycerol, cellulose derivatives, polyethylene glycol, silicone, and bentonite.

Inhalants are preparations intended to be applied to the bronchus or lungs by making a subject inhale an active ingredient in the form of aerosol. Inhalants include powdered inhalants, inhalant liquid agents, and inhalant aerosol agents. Powdered inhalants refer to the preparations by which powdered solid particles in the form of aerosol are inhaled. Powdered inhalants can be typically produced by mixing an active ingredient in the form of fine particles with optional additives such as lactose to form a homogeneous mixture. Inhalant liquid agents refer to liquid inhalants that are applied with a device such as a nebulizer. Inhalant liquid agents are typically produced by adding a solvent, a suitable isotonic agent, a pH adjuster, etc. to an active ingredient, and mixing them. Inhalant aerosol agents refer to metered-dose spray inhalants that spray a specific amount of an active ingredient together with a propellant that fills a container. Inhalant aerosol agents can be typically produced by adding a solvent, a suitable dispersant, stabilizer, etc. to an active ingredient to form a solution or suspension, filling a pressure-resistant container with the solution or suspension together with a liquid propellant, and attaching a metering valve to the container.

The pharmaceutical composition according to the present invention may optionally contain a colorant, a preservative, an aroma component, a flavoring, a sweetener, and other medical drugs.

The amount of the compound according to the present invention, a salt thereof, or a prodrug thereof contained in the pharmaceutical composition according to the present invention can be any amount and can be suitably selected from a wide range of amounts. The compound according to the present invention, a salt thereof, or a prodrug thereof is present in an amount of typically 0.5 to 90 wt %, 1 to 85 wt %, and preferably 1 to 80 wt % in the pharmaceutical composition.

The method for administering the pharmaceutical composition according to the present invention is not particularly limited, and can be administered by a method according to the dosage form, patient's age, gender, disease condition, and other conditions. For example, the pharmaceutical composition according to the present invention in the form of a tablet, pill, liquid agent, suspension, emulsion, granule, or capsule can be orally administered. The pharmaceutical composition according to the present invention in the form of injectable drug alone or in the form of injectable drug mixed with a typical replacement fluid such as glucose and amino acids can be intravenously administered; or the pharmaceutical composition in the form of injectable drug alone can be optionally administered, for example, intramuscularly, intradermally, subcutaneously, or intraperitoneally. The pharmaceutical composition according to the present invention in the form of suppository is intrarectally administered. The pharmaceutical composition according to the present invention in the form of inhalant is administered nasally.

The dose of the pharmaceutical composition that contains the compound according to the present invention, a salt thereof, or a prodrug thereof can be determined taking into consideration the regimen, patient's age, gender, severity of disease, and other conditions. The pharmaceutical composition is administered such that the amount of the compound according to the present invention, a salt thereof, or a prodrug thereof is typically 0.01 to 100 mg, and preferably 0.1 to 50 mg, per kilogram of body weight daily in one time or in several times per day, or every two days, three days, four days, five days, six days, one week, two weeks, or four weeks. Because the dose varies depending on various conditions, a dose lower than a dose within the ranges above may be sufficient in some cases, and a dose higher than a dose within the ranges above may be necessary in other cases.

The pharmaceutical composition according to the present invention may be combined with one or more other medicinal agents to form a combination drug.

The compound according to the present invention, a salt thereof, or a prodrug thereof has an action of regulating the activity of the TRPC3 channel (which may be referred to as "TRPC3 regulation" in the present specification), an action of regulating the activity of the TRPC6 channel (which may be referred to as "TRPC6 regulation" in the present specification), or an action of regulating the activity of both the TRPC3 channel and the TRPC6 channel (which may be collectively referred to as "TRPC3 and/or TRPC6 regulation" in the present specification).

The compound according to the present invention, a salt thereof, or a prodrug thereof also has an action of inhibiting the activity of the TRPC3 channel (which may be referred to as "TRPC3 inhibition" in the present specification), an action of inhibiting the activity of the TRPC6 channel (which may be referred to as "TRPC6 inhibition" in the present specification), or an action of inhibiting the activity of both the TRPC3 channel and the TRPC6 channel (which may be collectively referred to as "TRPC3 and/or TRPC6 inhibition" in the present specification). Thus, the compound according to the present invention, a salt thereof, or a prodrug thereof is effective as a TRPC3 and/or TRPC6 regulator or a TRPC3 and/or TRPC6 inhibitor; or the compound according to the present invention, a salt thereof, or a prodrug thereof is effective in the prevention or treatment of TRPC3 and/or TRPC6-related diseases. The TRPC3 and/or TRPC6 channel is present in the cell membrane, and controls the influx of cations into cells. The inhibition of the TRPC3 and/or TRPC6 channel suppresses phosphorylation signaling downstream of TGF-β via $Ca_2^+$ influxes in myofibroblasts, and suppresses the production of, for example, collagen I and smooth muscle actin (α-SMA; α-smooth muscle actin) (e.g., Inflammatory Bowel Diseases, 2015, March, 21(3), 496-506). In TRPC3 and/or TRPC6-related diseases, excessive activation of the TRPC3 and/or TRPC6 channel (the channels open to allow cations to excessively flow into cells) is observed.

The pharmaceutical composition according to the present invention is useful as a prophylactic and/or therapeutic agent for TRPC3 and/or TRPC6-related diseases. The TRPC3 and/or TRPC6-related diseases can be any disease caused by, for example, excessive activation or deactivation of the TRPC3 and/or TRPC6 channel; however, the TRPC3 and/or TRPC6-related diseases are preferably TRPC6-related diseases. Examples of TRPC3 and/or TRPC6-related diseases include fibrosis (e.g., pulmonary fibrosis, renal fibrosis, and cirrhosis caused by fibrosis), neurodegenerative diseases (e.g., amyotrophic lateral sclerosis (ALS) and Alzheimer's disease), muscular degenerative diseases (e.g., muscular dystrophy), inflammatory diseases (e.g., Crohn's disease, ulcerative colitis, non-alcoholic steatohepatitis (NASH)), Williams syndrome, chronic nephropathy, cardiac hypertrophy, and pulmonary hypertension. A preferable disease is, for example, fibrosis.

The compound of the present invention and the like are not prone to metabolization in the liver, while conventional TRPC3 and/or TRPC6 inhibitors are easily metabolized in the liver. Additionally, the compound of the present invention and the like are highly soluble in PBS, and are thus advantageous in forming them into a preparation; additionally, due to their high membrane permeability, the compound of the present invention and the like are advantageous in bioavailability. Thus, the compound according to the present invention, a salt thereof, or a prodrug thereof is excellent in pharmacokinetics. Thus, the compound according to the present invention, a salt thereof, or a prodrug thereof can exhibit inhibitory activity in a small amount for a long period of time, as compared with conventional TRPC3 and/or TRPC6 inhibitors.

Additionally, the compound of the present invention and the like are expected to have a lower action on TRP channels except for the TRPC3 and TRPC6 channels (e.g., TRPC1, TRPC2, TRPC5, TRPC7, TRPM2, TRPV1, and TRPV6), or on other $Ca^{2+}$ channels, $N^+$ channels, and $K^+$ channels. Thus, the compound of the present invention and the like are expected to have high selectivity for the TRPC6 and TRPC3 channels and cause fewer side effects.

The present invention includes a method for inhibiting TRPC3 and/or TRPC6, including administering an effective dose of the compound represented by formula (1) or (2), a pharmaceutically acceptable salt thereof, or a prodrug thereof to a patient in need of a TRPC3 and/or TRPC6 inhibition treatment.

The present invention includes a method for preventing or treating a TRPC3 and/or TRPC6-related disease, including administering an effective dose of the compound represented by formula (1) or (2), a pharmaceutically acceptable salt thereof, or a prodrug thereof to a patient in need of prevention or treatment of a TRPC3 and/or TRPC6-related disease.

The present invention includes a method for preventing or treating fibrosis, including administering an effective dose of the compound represented by formula (1) or (2), a pharmaceutically acceptable salt thereof, or a prodrug thereof to a patient in need of prevention or treatment of fibrosis.

The present invention includes use of the compound represented by formula (1) or (2), a pharmaceutically acceptable salt thereof, or a prodrug thereof in the production of a prophylactic and/or therapeutic agent for a TRPC3 and/or TRPC6-related disease.

The present invention includes use of the compound represented by formula (1) or (2), a pharmaceutically acceptable salt thereof, or a prodrug thereof in the production of a prophylactic and/or therapeutic agent for fibrosis.

EXAMPLES

The present invention is described below in more detail with reference to Reference Examples and Examples. However, the present invention is not limited to these Examples. The following conditions were used for LC/MS analysis of compounds.

LC/MS Analysis Conditions
LC/MS system: Waters ACQUITY UPLC H-Class/QDa Sample Manager—FTN
Quaternary Solvent Manager
Column Heater A
PDAeA Detector
QDa Detector
Column: ACQUITY UPLC BEH C18 1.7 µm (2.1×50 mm)
Flow rate: 0.5 mL/min
Elution conditions: mobile phase A: acetonitrile; mobile phase B: 0.1% aqueous formic acid solution

TABLE 1

| Time | Mobile phase B acetonitrile | Mobile phase A 0.1% formic acid |
|---|---|---|
| Initial | 10% | 90% |
| 3 min | 95% | 5% |
| 3.5 min | 10% | 90% |
| 5 min | 10% | 90% |

Example 1

Synthesis of 5-chloro-6-(4-(4-(trifluoromethyl) benzo[d]isoxazol-3-yl) piperazin-1-yl) nicotinic acid (Compound 011)

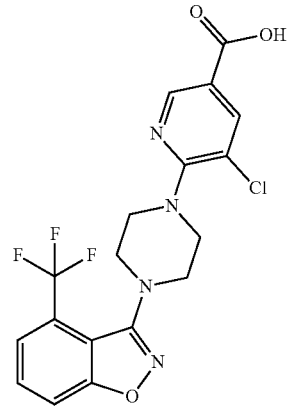 [SMILES: O=C(O)c1cnc(N2CCN(c3noc4cccc(C(F)(F)F)c34)CC2)c(Cl)c1]

Step 1-1
A 1 N aqueous sodium hydroxide solution (12.5 mL, 12.5 mmol) was added to a solution of 2-fluoro-6-(trifluoromethyl)benzaldehyde (2 g, 10.41 mmol) and hydroxyamine hydrochloride (0.868 g, 12.49 mmol) in ethanol (10 mL), and the mixture was stirred at room temperature for 3 hours. The reaction mixture was concentrated under reduced pressure, followed by extraction with ethyl acetate. The organic layer was washed with water and saturated saline, and then dried over magnesium sulfate, and the solvent was distilled off under reduced pressure to give 2-fluoro-6-(trifluoromethyl)benzaldehyde oxime (2.126 g).

Step 1-2
N-chlorosuccinimide (NCS) (1.435 g, 10.75 mmol) was added at 0° C. to a solution of 2-fluoro-6-(trifluoromethyl) benzaldehyde oxime (2.12 g, 10.24 mmol) in DMF (10 mL), and the mixture was stirred at room temperature overnight. LC/MS showed that the oxime was converted to 100% chloride. The solution of 2-fluoro-N-hydroxy-6-(trifluoromethyl)benzimidoyl chloride was used in the next reaction without purification.

Step 1-3

The solution (6 mL, about 6 mmol) of 2-fluoro-N-hydroxy-6-(trifluoromethyl)benzimidoyl chloride in DMF obtained in step 1-2 was added at room temperature to a solution of 5-chloro-6-(piperazin-1-yl)nicotinic acid hydrochloride (1836 mg, 6.6 mmol) and triethylamine (2.93 mL, 21 mmol) in dichloromethane (10 mL), and the mixture was stirred overnight. A 10% aqueous $KHSO_4$ solution was added to the reaction solution, followed by extraction with ethyl acetate. The organic layer was dried over magnesium sulfate, and the solvent was distilled off under reduced pressure. The residue was purified by preparative silica gel column chromatography (ethyl acetate/methanol) to give (E)-5-chloro-6-(4-((2-fluoro-6-(trifluoromethyl)phenyl)(hydroxyimino)methyl)piperazin-1-yl)nicotinic acid (Compound 012(E); 1258 mg; LC-MS: r.t. 2.45 min., m/z 447 (M+1)) and its Z-isomer (Compound 012(Z); 93 mg; LC-MS: r.t. 2.26 min., m/z 447 (M+1)).

Step 1-4

A mixed solution of a 2N aqueous potassium hydroxide solution (6 mL) of (E)-5-chloro-6-(4-((2-fluoro-6-(trifluoromethyl)phenyl)(hydroxyimino)methyl)piperazin-1-yl)nicotinic acid (1026 mg) and dioxane (18 mL) was heated with stirring at 105° C. for 3 hours. LC/MS analysis showed 100% conversion. The solution was concentrated under reduced pressure and neutralized with a 2 N aqueous hydrochloric acid solution. The obtained solid was collected by filtration and dried to give 876 mg of the title compound.

(Rf=0.5, ethyl acetate)

$^1$H NMR (DMSO, 400 MHz) δ8.68 (d, 1H, J=1.6 Hz), 8.06-8.11 (m, 2H), 7.83-7.88 (m, 2H), 3.59-3.64 (m, 4H), 3.33-3.38 (m, 4H), LC-MS: r.t. 3.23 min., m/z 427 (M+1).

Example 2

Synthesis of 5-chloro-N-methyl-6-(4-(4-(trifluoromethyl)benzo[d]isoxazol-3-yl)piperazin-1-yl)nicotinamide (Compound 021)

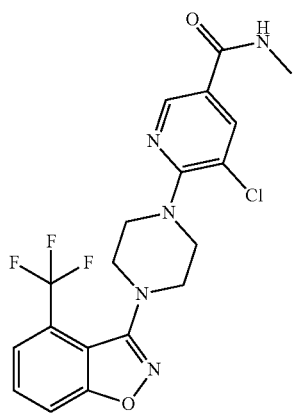 [SMILES: CNC(=O)c1cnc(N2CCN(c3noc4cccc(C(F)(F)F)c34)CC2)c(Cl)c1]

A solution of 5-chloro-6-(4-(4-(trifluoromethyl)benzo[d]isoxazol-3-yl)piperazin-1-yl) nicotinic acid (compound of Example 1, 22.5 mg, 0.053 mmol), triethylamine (29.4 μL, 0.211 mmol), 1-[dimethylamino(dimethyliminio)methyl]-1H-1,2,3-triazolo[4,5-b]pyridine 3-oxide hexafluorophosphate (also referred to below as "HATU") (40.1 mg, 0.105 mmol), and methylamine (0.2 mmol) in THF (0.5 mL) was stirred at room temperature overnight. The resulting solution was concentrated, and the residue was purified by preparative liquid silica gel chromatography (hexane/ethyl acetate) to give 20.8 mg of the title compound.

(Rf=0.5, 1:2 hexane/ethyl acetate)

$^1$H NMR (CDCl$_3$, 400 MHz) δ8.52 (d, 1H, J=2.0 Hz), 8.04 (d, 1H, J=2.0 Hz), 7.73 (d, 1H, J=7.2 Hz), 7.63 (dd, 1H, J=7.6, 8.8 Hz), 7.64 (bs, 1H), 6.10 (br, 1H), 3.67-3.72 (m, 4H), 3.44-3.48 (m, 4H), 3.02 (d, 3H, J=6.8 Hz), LC-MS: r.t. 2.84 min., m/z 440 (M+1).

Example 3

Synthesis of (S)-5-chloro-6-(3-methyl-4-(4-(trifluoromethyl)benzo[d]isoxazol-3-yl)piperazin-1-yl) nicotinic acid (Compound 031)

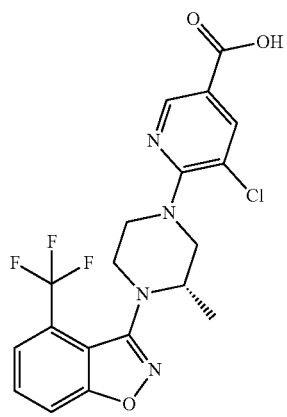 [SMILES: C[C@H]1CN(c2ncc(C(=O)O)cc2Cl)CCN1c1noc2cccc(C(F)(F)F)c12]

A solution of (S)-2-methylpiperazine (1.002 g, 10 mmol), 5,6-dichloronicotinic acid (1.92 g, 10 mmol), and N-ethyl-N-isopropylpropan-2-amine (3.48 mL, 20 mmol) in DMF (20 mL) was heated with stirring at 90° C. for 10 hours. The solution was diluted with purified water and then neutralized with 10% $KHSO_4$ to adjust the pH to about 6. The resulting solid was collected by filtration and dried under reduced pressure to give 429 mg of crude (S)-5-chloro-6-(3-methylpiperazin-1-yl) nicotinic acid. The obtained crude (S)-5-chloro-6-(3-methylpiperazin-1-yl) nicotinic acid was used in the next step without purification.

The title compound was obtained according to the procedures of step 1-3 and step 1-4 in Example 1, except that the obtained crude (S)-5-chloro-6-(3-methylpiperazin-1-yl) nicotinic acid was used in place of 5-chloro-6-(piperazin-1-yl)nicotinic acid hydrochloride.

(Rf=0.25, 2:1 ethyl acetate/hexane)

$^1$H NMR (DMSO, 400 MHz) δ8.70 (d, 1H, J=2.4 Hz), 8.11 (d, 1H, J=2.4 Hz), 8.10 (d, 1H, J=7.6 Hz), 7.85 (d, 1H, J=7.6 Hz), 7.83 (d, 1H, J=7.6 Hz), 3.64-3.90 (m, 3H), 3.04-3.52 (m, 4H), 1.08 (d, 3H, J=6.0 Hz), LC-MS: r.t. 3.03 min., m/z 441 (M+1).

Example 4

Synthesis of (R)-5-chloro-6-(3-methyl-4-(4-(trifluoromethyl)benzo[d]isoxazol-3-yl)piperazin-1-yl) nicotinic acid (Compound 041)

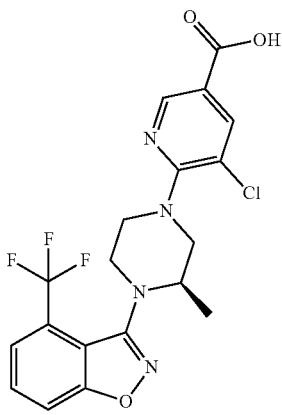 [SMILES: C[C@@H]1CN(c2ncc(C(=O)O)cc2Cl)CCN1c1noc2cccc(C(F)(F)F)c12]

The title compound was obtained according to the procedure of Example 3, except that (R)-2-methylpiperazine was used in place of (S)-2-methylpiperazine.

$^1$H NMR (DMSO, 400 MHz) δ8.70 (d, 1H, J=2.4 Hz), 8.11 (d, 1H, J=2.4 Hz), 8.10 (d, 1H, J=7.6 Hz), 7.85 (d, 1H, J=7.6 Hz), 7.83 (d, 1H, J=7.6 Hz), 3.64-3.90 (m, 3H), 3.04-3.52 (m, 4H), 1.08 (d, 3H, J=6.0 Hz), LC-MS: r.t. 3.03 min., m/z 441 (M+1).

Example 5

Synthesis of 5-chloro-6-(4-(4-(methoxy)benzo[d]isoxazol-3-yl)piperazin-1-yl)nicotinic acid (Compound 051)

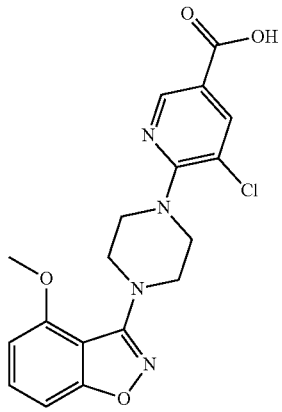 [SMILES: COc1cccc2onc(N3CCN(c4ncc(C(=O)O)cc4Cl)CC3)c12]

The title compound was obtained according to the procedure of Example 1, except that 2-fluoro-6-(methoxy)benzaldehyde was used in place of 2-fluoro-6-(trifluoromethyl)benzaldehyde.

Rf=0.2, 10% methanol/ethyl acetate $^1$H NMR (DMSO, 400 MHz) δ8.69 (d, 1H, J=1.6 Hz), 8.11 (d, 1H, J=1.6 Hz), 7.54 (t, 1H, J=8.4 Hz), 7.16 (d, 1H, J=8.4 Hz), 6.84 (d, 1H, J=8.4 Hz), 3.96 (s, 3H), 3.77 (7et, 1H, J=5.6 Hz), 3.63-3.67 (m, 4H), 3.52-3.56 (m, 4H), 1.03 (d, 6H, J=5.6 Hz), LC-MS: r.t. 2.60 min., m/z 389 (M+1).

In the course of synthesis, 5-chloro-6-(4-((2-fluoro-6-methoxyphenyl(hydroxyimino)methyl) piperazin-1-yl) nicotinic acid (Compound 052) was obtained (LC-MS: r.t. 2.11 min., m/z 409 (M+1)).

Example 6

Synthesis of 4-chloro-3-(4-(2-chlorophenyl)piperazin-1-yl)benzo[d]isoxazole (Compound 061)

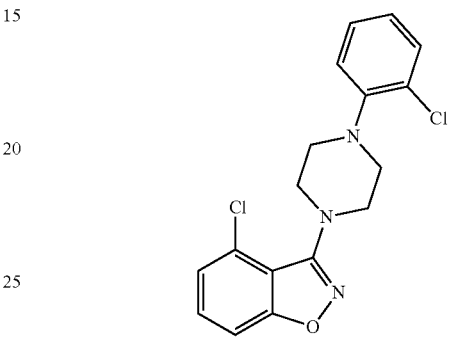

Step 6-1

A solution of 2,6-dichloro-N-hydroxy-6-benzimidoyl chloride in DMF was obtained according to the procedures of step 1-1 and step 1-2 in Example 1, except that 2,6-dichlorobenzaldehyde was used in place of 2-fluoro-6-(trifluoromethyl)benzaldehyde.

Step 6-2

The solution (0.5 mL, about 0.5 mmol) of 2,6-dichloro-N-hydroxy-6-benzimidoyl chloride in DMF obtained in step 6-1 was added at room temperature to a solution of 1-(2-chlorophenyl)piperazine (118 mg, 0.6 mmol) and triethylamine (83 μL, 0.6 mmol) in dichloromethane (2 mL), and the mixture was stirred for 3 hours. A saturated aqueous ammonium chloride solution was added to the reaction solution, followed by extraction with ethyl acetate. The organic layer was dried over magnesium sulfate, and the solvent was distilled off under reduced pressure. The residue was purified by preparative silica gel column chromatography (ethyl acetate/methanol) to give (E)-(4-(2-chlorophenyl) piperazin-1-yl)(2,6-dichlorophenyl)methanone oxime (58.7 mg) and its Z-isomer (50 mg).

(E)-(4-(2-chlorophenyl)piperazin-1-yl)(2,6-dichlorophenyl) methanone oxime (Compound 062(E))

Rf: 0.5, 3:1 hexane/ethyl acetate, $^1$H NMR (CDCl$_3$, 400 MHz) δ7.41 (d, 1H, J=1.6 Hz), 7.39 (s, 1H), 7.36 (dd, 1H, J=1.6, 8.0 Hz), 7.30 (dd, 1H, J=7.2, 8.8 Hz), 7.21 (dd, 1H, J=1.2, 7.2 Hz), 7.03 (dd, 1H, J=2.0, 8.0 Hz), 6.98 (dt, 1H, J=1.2, 8.0 Hz), 5.72 (br, 1H), 3.35-3.40 (m, 4H), 3.04-3.09 (m, 4H), LC-MS: r.t. 3.03 min., m/z 384 (M+1).

(Z)-(4-(2-chlorophenyl)piperazin-1-yl)(2,6-dichlorophenyl)methanone oxime (Compound 062 (Z))

Rf: 0.3, 3:1 hexane/ethyl acetate, $^1$H NMR (CDCl$_3$, 400 MHz) δ7.36 (dd, 1H, J=1.2, 7.2 Hz), 7.35 (d, 1H, J=1.2, 8.0 Hz), 7.26 (dd, 1H, J=1.2, 8.0

Hz), 7.28 (dd, 1H, J=2.0, 8.0 Hz), 7.22 (dt, 1H, J=1.2, 7.2 Hz), 7.04 (dd, 1H, J=8.0 Hz), 6.97 (dt, 1H, J=1.2, 8.0 Hz), 6.46 (br, 1H), 3.53-3.57 (m, 4H), 3.09-3.13 (m, 4H), LC-MS: r.t. 3.03 min., m/z 384 (M+1).

Step 6-3

A mixed solution of a 2N aqueous potassium hydroxide solution (1 mL) of (E)-(4-(2-chlorophenyl)piperazin-1-yl) (2,6-dichlorophenyl)methanone oxime (58.7 mg, 0.152 mmol) and dioxane (3 mL) was heated with stirring at 120° C. for 25 hours. The solution was concentrated under reduced pressure and neutralized with a 2 N aqueous hydrochloric acid solution, followed by extraction with ethyl acetate. The organic layer was dried over magnesium sulfate, and the solvent was distilled off under reduced pressure. The residue was purified by preparative silica gel column chromatography (ethyl acetate/methanol) to give 6.9 mg of the title compound.

$^1$H NMR (CDCl$_3$, 400 MHz) δ7.42 (t, J=8.0 Hz), 7.37-7.41 (m, 2H), 7.44-7.52 (m, 2H), 7.21-7.27 (m, 2H), 7.11 (dd, 1H, J=1.6, 8.0 Hz), 7.00 (dt, 1H, J=1.6, 8.0 Hz), 3.60-3.67 (m, 4H), 3.26-3.30 (m, 4H), LC-MS: r.t. 3.01 min., m/z 384 (M+1).

Example 7

Synthesis of 4-chloro-3-(4-(3-chloropyridin-2-yl) piperazin-1-yl)benzo[d]isoxazole (Compound 071)

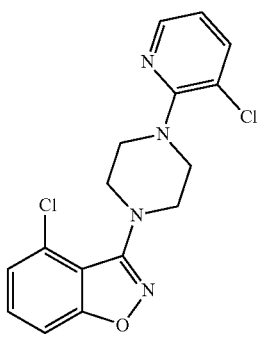 [SMILES: Clc1cccnc1N1CCN(c2noc3cccc(Cl)c23)CC1]

Step 7-1

(E)-(4-(3-chloropyridin-2-yl)piperazin-1-yl)(2,6-dichlorophenyl)methanone oxime and its Z-isomer were obtained according to the procedure of step 6-2 in Example 6, except that 1-(3-chloropyridin-2-yl)piperazine hydrochloride was used in place of 1-(2-chlorophenyl)piperazine.

(E)-(4-(3-chloropyridin-2-yl)piperazin-1-yl)(2,6-dichlorophenyl)methanone oxime (Compound 072 (E))

$^1$H NMR (CDCl$_3$, 400 MHz) δ8.17 (dd, 1H, J=1.6, 4.8 Hz), 7.58 (dd, 1H, J=1.2, 7.6 Hz), 7.39 (dd, 1H, J=1.2, 7.6 Hz), 7.33 (s, 1H), 7.28 (dd, 1H, J=7.6, 9.2 Hz), 7.06 (br, 1H), 6.85 (dd, 1H, J=4.8, 8.0 Hz), 5.72 (br, 1H), 3.25-3.34 (m, 8H),

LC-MS: r.t. 3.03 min., m/z 384 (M+1).

(Z)-(4-(3-chloropyridin-2-yl)piperazin-1-yl)(2,6-dichlorophenyl) methanone oxime (Compound 072 (Z))

$^1$H NMR (CDCl$_3$, 400 MHz) δ8.18 (d, 1H, J=3.6 Hz), 7.57 (d, 1H, J=7.6 Hz), 7.38 (t, 1H, J=8.0 Hz), 7.34 (d, 1H, J=7.6 Hz), 7.26 (t, 1H, J=8.0 Hz), 7.08 (br, 1H), 6.84 (dd, 1H, J=4.8, 8.0 Hz), 5.72 (br, 1H), 3.52-3.58 (m, 3H), 3.40-3.44 (m, 3H), 3.35-3.38 (m, 2H), LC-MS: r.t. 2.70 min., m/z 385 (M+1).

Step 7-2

A mixed solution of a 2 N aqueous potassium hydroxide solution (2 mL) of (E)-(4-(3-chloropyridin-2-yl)piperazin-1-yl)(2,6-dichlorophenyl)methanone oxime (192 mg, 0.498 mmol) and dioxane (6 mL) was heated with stirring at 120° C. for 1 hour with microwaves. LC/MS analysis showed about 50% conversion. The solution was neutralized with a 1 N aqueous hydrochloric acid solution and a saturated aqueous ammonium chloride solution, followed by extraction with ethyl acetate. The organic layer was dried over magnesium sulfate, and the solvent was distilled off under reduced pressure. The residue was purified by preparative silica gel column chromatography (ethyl acetate/methanol) to give 70.6 mg of the title compound and 79 mg of the starting material.

$^1$H NMR (CDCl$_3$, 400 MHz) δ7.42 (t, 1H, J=8.0 Hz), 7.37-7.41 (m, 2H), 7.44-7.52 (m, 2H), 7.21-7.27 (m, 2H), 7.11 (dd, 1H, J=1.6, 8.0 Hz), 7.00 (dt, 1H, J=1.6, 8.0 Hz), 3.60-3.67 (m, 4H), 3.26-3.30 (m, 4H), LC-MS: r.t. 3.01 min., m/z 384 (M+1).

Example 8

Synthesis of 5-chloro-6-(4-(4-chlorobenzo[d]isoxazol-3-yl)piperazin-1-yl)nicotinic acid (Compound 081)

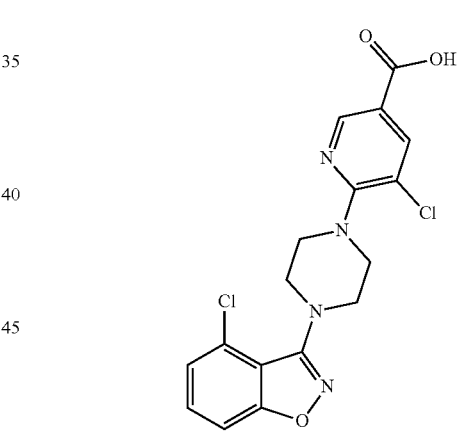

Step 8-1

5-chloro-6-(4-((2,6-dichlorophenyl)(hydroxyimino) methyl) piperazin-1-yl) nicotinic acid (Compound 082) was obtained according to the procedure of step 6-2 of Example 6, except that 5-chloro-6-(piperazin-1-yl)nicotinic acid trifluoroacetate was used in place of 1-(2-chlorophenyl)piperazine.

Step 8-2

A mixed solution of a 2 N aqueous potassium hydroxide solution (2 mL) of 5-chloro-6-(4-((2,6-dichlorophenyl)(hydroxyimino)methyl)piperazin-1-yl)nicotinic acid (215 mg, 0.5 mmol) and dioxane (6 mL) was heated with stirring at 140° C. for 1 hour with microwaves. LC/MS analysis showed about 90% conversion. The solution was neutralized with a 1 N aqueous hydrochloric acid solution and a 10% aqueous KHSO$_4$ solution, followed by extraction with ethyl acetate. The organic layer was dried over magnesium sulfate, and the solvent was distilled off under reduced pressure. The residue was purified by preparative silica gel column chromatography (ethyl acetate/methanol) to give 75 mg of the title compound.

$^1$H NMR (DMSO, 400 MHz) δ8.66 (d, 1H, J=2.0 Hz), 8.08 (d, 1H, J=2.0 Hz), 7.63 (d, 1H, J=8.0 Hz), 7.60 (t, 1H, J=8.0 Hz), 7.42 (d, 1H, J=8.0 Hz), 3.63-3.67 (m, 4H), 3.43-3.47 (m, 4H), LC-MS: r.t. 2.87 min., m/z 393 (M+1).

Example 9

Synthesis of 5-chloro-6-(4-(4-chlorobenzo[d]isoxazol-3-yl)piperazin-1-yl)N,N-dimethylnicotinamide (Compound 091)

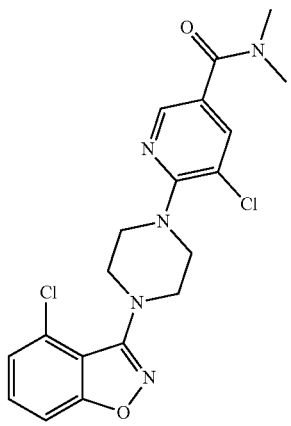 [SMILES: CN(C)C(=O)c1cnc(N2CCN(c3noc4cccc(Cl)c34)CC2)c(Cl)c1]

Step 9-1

A solution of 6-(4-(tert-butoxycarbonyl)piperazin-1-yl)-5-chloronicotinic acid (171 mg, 0.5 mmol), dimethylamine (0.75 mmol), triethylamine (209 μL, 1.5 mmol), and HATU (285 mg, 0.75 mmol) in DMF (3 mL) was stirred at room temperature for 3 hours, and saturated saline was added, followed by extraction with ethyl acetate. The organic layer was dried over magnesium sulfate, and the solvent was distilled off under reduced pressure. The residue was purified by preparative silica gel column chromatography to give 153.2 mg of tert-butyl 4-(3-chloro-5-(dimethylcarbamoyl)pyridin-2-yl)piperazine-1-carboxylate (Rf=0.45, 1:3 hexane/ethyl acetate). This compound was treated with excess trifluoroacetic acid to give 5-chloro-N,N-dimethyl-6-(piperazin-1-yl)nicotinamide trifluoroacetate.

Step 9-2

The solution (0.5 mL, about 0.5 mmol) of 2,6-dichloro-N-hydroxy-6-benzimidoyl chloride in DMF obtained in step 6-1 of Example 6 was added at room temperature to a solution of 5-chloro-N,N-dimethyl-6-(piperazin-1-yl)nicotinamide (159 mg, 0.415 mmol) and triethylamine (289 μL, 2.075 mmol) in DMF (2 mL), and the mixture was stirred for 3 hours. A saturated aqueous ammonium chloride solution was added to the reaction solution, followed by extraction with ethyl acetate. The organic layer was dried over magnesium sulfate, and the solvent was distilled off under reduced pressure. The residue was purified by preparative silica gel column chromatography (ethyl acetate/methanol) to give (E)-5-chloro-6-(4-((2,6-dichlorophenyl)(hydroxyimino)methyl)piperazin-1-yl)-N,N-dimethylnicotinamide (Compound 092(E); 77.2 mg; LC-MS: r.t. 2.27 min., m/z 456 (M+1)) and its Z-isomer (30 mg). (Z)-5-chloro-6-(4-((2,6-dichlorophenyl)(hydroxyimino)methyl)piperazin-1-yl)-N,N-dimethylnicotinamide (Compound 092(Z)):

$^1$H NMR (CDCl$_3$, 400 MHz) δ8.24 (d, 1H, J=2.0 Hz), 7.72 (d, 1H, J=2.4 Hz), 7.39 (dd, 1H, J=0.8, 8.0 Hz), 7.38 (s, 1H), 7.30 (dd, 1H, J=4.8, 8.8 Hz), 6.20 (br, 1H), 3.43-3.47 (m, 4H), 3.32-3.36 (m, 4H), 3.08 (s, 6H), LC-MS: r.t. 2.08 min., m/z 456 (M+1).

Step 9-3

A mixed solution of a 2 N aqueous potassium hydroxide solution (2 mL) of (E)-5-chloro-6-(4-((2,6-dichlorophenyl)(hydroxyimino)methyl)piperazin-1-yl)-N,N-dimethylnicotinamide (77.2 mg, 0.048 mg) and dioxane (6 mL) was heated with stirring at 140° C. for 1 hour with microwaves. LC/MS analysis showed about 70% conversion. A 10% aqueous KHSO$_4$ solution was added to the solution, followed by extraction with ethyl acetate. The organic layer was dried over magnesium sulfate, and the solvent was distilled off under reduced pressure. The resulting solid was recrystallized from isopropanol to give 20.2 mg of the title compound.

$^1$H NMR (CDCl$_3$, 400 MHz) δ8.28 (d, 1H, J=2.4 Hz), 7.74 (d, 1H, J=2.4 Hz), 7.42 (dd, 1H, J=6.8, 8.8 Hz), 7.39 (dd, 1H, J=1.2, 8.8 Hz), 7.26 (dd, 1H, J=1.2, 6.8 Hz), 3.64-3.68 (m, 4H), 3.58-3.61 (m, 4H), LC-MS: r.t. 2.89 min., m/z 420 (M+1).

Example 10

Synthesis of 3-chloro-4-(4-(4-chlorobenzo[d]isoxazol-3-yl)piperazin-1-yl)benzoic acid (Compound 101)

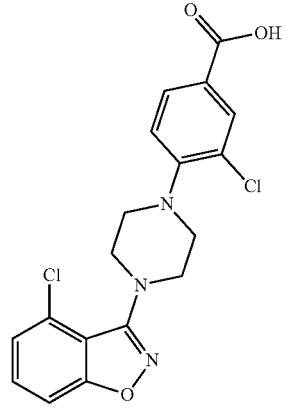 [SMILES: O=C(O)c1ccc(N2CCN(c3noc4cccc(Cl)c34)CC2)c(Cl)c1]

Step 10-1

3-Chloro-4-(4-((2,6-dichlorophenyl)(hydroxyimino)methyl) piperazin-1-yl)benzoic acid methyl ester (Compound 102) was obtained (LC-MS: r.t. 2.97 min., m/z 442 (M+1)) according to the procedure of step 6-2 in Example 6, except that 3-chloro-4-(piperazin-1-yl)benzoic acid methyl ester was used in place of 1-(2-chlorophenyl)piperazine.

Step 10-2

The title compound was obtained according to the procedure of step 8-2 in Example 8, except that 3-chloro-4-(4-((2,6-dichlorophenyl)(hydroxyimino)methyl) piperazin-1-yl)benzoic acid methyl ester was used in place of 5-chloro-6-(4-((2,6-dichlorophenyl)(hydroxyimino)methyl) piperazin-1-yl) nicotinic acid.

$^1$H NMR (DMSO, 400 MHz) δ7.85 (d, 1H, J=1.6 Hz), 7.79 (dd, 1H, J=1.6, 8.4 Hz), 7.67 (dd, 1H, J=1.6, 8.4 Hz), 7.63 (dd, 1H, J=7.2, 8.8 Hz), 7.45 (dd, 1H, J=1.2, 8.0 Hz), 7.22 (bd, 1H, J=8.0 Hz), 3.48-3.53 (m, 4H), 3.24-3.28 (m, 4H), LC-MS: r.t. 2.94 min., m/z 392 (M–1).

Example 11

Synthesis of 5-chloro-3-(4-(3-chloropyridin-2-yl)piperazin-1-yl)benzo[d]isoxazole (Compound 111)

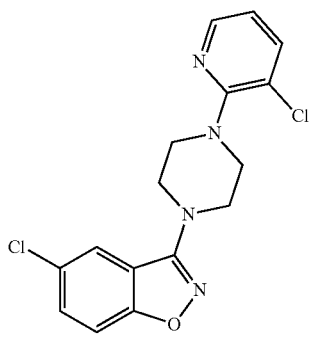 [SMILES: Clc1ccc2onc(N3CCN(c4ncccc4Cl)CC3)c2c1]

Step 11-1

A solution of 2,5-dichloro-N-hydroxy-6-benzimidoyl chloride in DMF was obtained according to the procedures of step 1-1 and step 1-2 in Example 1, except that 2,5-dichlorobenzaldehyde was used in place of 2-fluoro-6-(trifluoromethyl)benzaldehyde.

Step 11-2

(E)-(4-(3-chloropyridin-2-yl)piperazin-1-yl)(2,5-dichlorophenyl)methanone oxime, and its Z-isomer and E,Z mixture were obtained according to the procedure of step 6-2 in Example 6, except that 1-(3-chloropyridin-2-yl)piperazine hydrochloride was used in place of 1-(2-chlorophenyl)piperazine, and the solution of 2,5-dichloro-N-hydroxy-6-benzimidoyl chloride in DMF was used in place of the solution of 2,6-dichloro-N-hydroxy-6-benzimidoyl chloride in DMF.

(E)-(4-(3-chloropyridin-2-yl)piperazin-1-yl)(2,5-dichlorophenyl)methanone oxime (Compound 112 (E))

¹H NMR (CDCl₃, 400 MHz) δ8.18 (dd, 1H, J=1.2, 4.8 Hz), 7.59 (dd, 1H, J=2.0. 8.0 Hz), 7.40 (d, 1H, J=8.0 Hz), 7.33 (dd, 1H, J=4.8, 8.0 Hz), 5.83 (br, 1H), 3.29-3.37 (m, 6H), 3.18-3.25 (m, 2H), LC-MS: r.t. 2.83 min., m/z 385 (M+1).

(Z)-4-(3-chloropyridin-2-yl)piperazin-1-yl)(2,5-dichlorophenyl)methanone oxime (Compound 112 (Z))

¹H NMR (CDCl₃, 400 MHz) δ8.40 (br, 1H), 8.17 (dd, 1H, J=1.6, 4.8 Hz), 7.57 (dd, 1H, J=2.0. 7.6 Hz), 7.41 (d, 1H, J=2.0 Hz), 7.32 (s, 1H), 7.31 (d, 1H, J=2.4 Hz), 6.83 (dd, 1H, J=4.8, 8.0 Hz), 3.47-3.52 (m, 4H), 3.36-3.41 (m, 4H), LC-MS: r.t. 2.83 min., m/z 385 (M+1).

Step 11-3

A mixed solution of a 2 N aqueous potassium hydroxide solution (1 mL) of (E)-(4-(3-chloropyridin-2-yl)piperazin-1-yl)(2,5-dichlorophenyl)methanone oxime (26.8 mg, 0.069 mmol) and dioxane (3 mL) was heated with stirring with microwaves at 120° C. for 0.5 hours and then at 140° C. for 1 hour. The solution was neutralized with a 1 N aqueous hydrochloric acid solution and a saturated aqueous ammonium chloride solution, followed by extraction with ethyl acetate. The organic layer was dried over magnesium sulfate, and the solvent was distilled off under reduced pressure. The residue was purified by preparative silica gel column chromatography (ethyl acetate) to give 17.6 mg of the title compound.

¹H NMR (CDCl₃, 400 MHz) δ8.2 (dd, 1H, J=1.6, 4.8 Hz), 7.71 (d, 1H, J=1.6 Hz), 7.63 (dd, 1H, J=1.2, 8.0 Hz), 7.46 (dd, 1H, J=2.0, 8.4 Hz), 7.40 (d, 1H, 8.4 Hz), 6.90 (dd, 1H, J=4.8, 8.0 Hz), 3.68-3.72 (m, 4H), 3.55-3.59 (m, 4H), LC-MS: r.t. 3.18 min., m/z 349 (M+1).

Example 12

Synthesis of 5-chloro-6-(4-(5-chlorobenzo[d]isoxazol-3-yl)piperazin-1-yl)nicotinic acid (Compound 121)

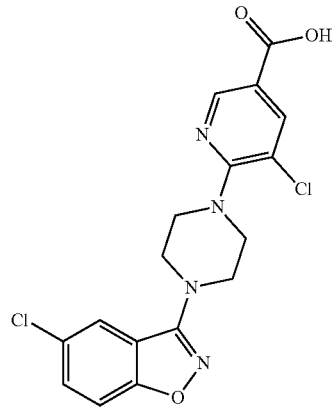 [SMILES: O=C(O)c1cnc(N2CCN(c3noc4ccc(Cl)cc34)CC2)c(Cl)c1]

Step 12-1

5-Chloro-6-(4-((2,5-dichlorophenyl)(hydroxyimino)methyl)piperazin-1-yl)nicotinic acid (Compound 122) was obtained (LC-MS: r.t. 2.46 min., m/z 429 (M+1)) according to the procedure of step 6-2 in Example 6, except that 5-chloro-6-(piperazin-1-yl)nicotinic acid hydrochloride was used in place of 1-(2-chlorophenyl)piperazine, and a solution of 2,5-dichloro-N-hydroxy-6-benzimidoyl chloride in DMF was used in place of the solution of 2,6-dichloro-N-hydroxy-6-benzimidoyl chloride in DMF.

Step 12-2

A mixed solution of a 2 N aqueous potassium hydroxide solution (2 mL) of 5-chloro-6-(4-((2,5-dichlorophenyl)(hydroxyimino)methyl)piperazin-1-yl)nicotinic acid (115.1 mg, 0.5 mmol) and dioxane (6 mL) was heated with stirring at 140° C. for 2 hours with microwaves. LC/MS analysis showed about 100% conversion. The solution was neutralized with a 1 N aqueous hydrochloric acid solution and a 10% aqueous KHSO₄ solution, followed by extraction with ethyl acetate. The organic layer was dried over magnesium sulfate, and the solvent was distilled off under reduced pressure. The residue was recrystallized from isopropanol to give 26.8 mg of the title compound.

¹H NMR (DMSO, 400 MHz) δ8.65 (d, 1H, J=2.0 Hz), 8.17 (bs, 1H), 8.08 (d, 1H, J=1.6 Hz), 7.60-7.61 (m, 2H), 3.59-3.61 (m, 4H), 3.25-3.35 (m, 4H), LC-MS: r.t. 2.83 min., m/z 393 (M+1).

Example 13

Synthesis of 5-chloro-6-(4-(5-(trifluoromethyl)benzo[d]isoxazol-3-yl)piperazin-1-yl)nicotinic acid (Compound 131)

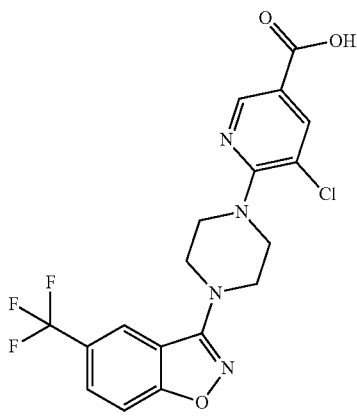 [SMILES: O=C(O)c1cnc(N2CCN(c3noc4ccc(C(F)(F)F)cc34)CC2)c(Cl)c1]

Step 13-1

A 1 N aqueous sodium hydroxide solution (28.8 mL, 28.8 mmol) was added to a solution of 2-chloro-5-(trifluoromethyl)benzaldehyde (5 g, 23.97 mmol) and hydroxyamine hydrochloride (2 g, 28.8 mmol) in ethanol (20 mL), and the mixture was stirred at room temperature for 3 hours. The reaction mixture was concentrated under reduced pressure, followed by extraction with ethyl acetate. After the organic layer was washed with water and saturated saline, the organic layer was dried over magnesium sulfate, and the solvent was distilled off under reduced pressure to give 2-chloro-5-(trifluoromethyl)benzaldehyde oxime (4.77 g) as a mixture of Z- and E-isomers.

Step 13-2

N-chlorosuccinimide (NCS) (2.99 g, 22.4 mmol) was added at 0° C. to a solution of 2-chloro-5-(trifluoromethyl)benzaldehyde oxime (4.77 g, 21.33 mmol) in DMF (10 mL), and the mixture was stirred at room temperature overnight. LC/MS showed that the oxime was converted to 100% chloride. The solution of 2-chloro-N-hydroxy-5-(trifluoromethyl)benzimidoyl chloride was used in the next reaction without purification.

Step 13-3

The solution (0.252 mL, about 0.252 mmol) of 2-chloro-N-hydroxy-5-(trifluoromethyl)benzimidoyl chloride in DMF obtained in step 13-2 was added at room temperature to a solution of 5-chloro-6-(piperazin-1-yl)nicotinic acid hydrochloride (70 mg, 0.252 mmol) and triethylamine (140 μL, 1.0 mmol) in dichloromethane (1 mL), and the mixture was stirred for 3 hours. A 10% aqueous KHSO$_4$ solution was added to the reaction solution, and the insoluble matter was filtered off. Thereafter, the filtrate was extracted with ethyl acetate. The organic layer was dried over magnesium sulfate, and the solvent was distilled off under reduced pressure to give crude 5-chloro-6-(4-((2-chloro-5-(trifluoromethyl)phenyl)(hydroxyimino)methyl)piperazin-1-yl)nicotinic acid (Compound 132) (LC-MS: r.t. 2.59 min., m/z 463 (M+1)). This compound was used in the next step without purification.

Step 13-4

A mixed solution of a 2 N aqueous potassium hydroxide solution (1 mL, 2 mmol) of 5-chloro-6-(4-((2-chloro-5-(trifluoromethyl)phenyl)(hydroxyimino)methyl)piperazin-1-yl)nicotinic acid (117 mg, 0.253 mmol) and dioxane (5 mL) was heated with stirring at 160° C. for 1 hour with microwaves. LC/MS analysis showed 100% conversion. The solution was neutralized with a 10% aqueous KHSO$_4$ solution, followed by extraction with ethyl acetate. The organic layer was dried over magnesium sulfate, and the solvent was distilled off under reduced pressure. The residue was purified by preparative silica gel column chromatography (ethyl acetate) to give 42 mg of the crude title compound. This compound was further washed with warmed acetonitrile to give 29.9 mg of the title compound.

$^1$H NMR (DMSO, 400 MHz) δ8.70 (d, 1H, J=2.4 Hz), 8.50 (bs, 1H), 8.13 (d, 1H, J=1.6 Hz), 7.95 (dd, 1H, 1.6, 8.4 Hz), 7.84 (d, 1H, J=8.4 Hz), 3.68-3.71 (m, 4H), 3.31-3.34 (m, 4H), LC-MS: r.t. 2.92 min., m/z 427 (M+1).

Example 14

Synthesis of 3-(4-(pyridin-2-yl)piperazin-1-yl)benzo[d]isoxazole (Compound 141)

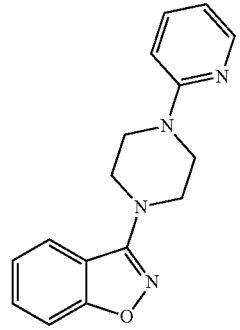 [SMILES: c1ccc(N2CCN(c3noc4ccccc34)CC2)nc1]

A solution of 3-chlorobenzo[d]isoxazole (100 mg, 0.651 mmol) and 1-(pyridin-2-yl)piperazine (319 mg, 1.954 mmol) in pyridine (1 mL) was heated with stirring at 150° C. for 1 hour with microwaves. The solvent was distilled off under reduced pressure, and the residue was purified by preparative silica gel column chromatography (ethyl acetate) to give 61.1 mg of the title compound.

$^1$H NMR (CDCl$_3$, 400 MHz) δ8.31 (dd, 1H, J=4.0, 1.6 Hz), 7.72 (d, 1H, J=8.4 Hz), 7.45-7.56 (m, 3H), 7.25 (dt, 1H, J=1.2, 6.4 Hz), 6.72 (d, 1H, J=8.8 Hz), 6.68 (dd, 1H, J=4.8, 7.2 Hz), 3.74-3.78 (m, 4H), 3.67-3.71 (m, 4H), LC-MS: r.t. 1.52 min., m/z 281 (M+1).

Example 15

Synthesis of 3-(4-(2-chlorophenyl)piperazin-1-yl)benzo[d]isoxazole (Compound 151)

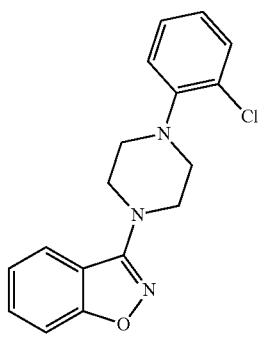

A solution of 3-chlorobenzo[d]isoxazole (77.5 mg, 0.505 mmol) and 1-(2-chlorophenyl)piperazine (84 μL, 0.505 mmol) in pyridine (1 mL) was heated with stirring at 180° C. for 40 minutes with microwaves. The solvent was distilled off under reduced pressure, and the residue was purified by preparative silica gel column chromatography (ethyl acetate/hexane) to give 8.7 mg of the title compound.

Rf: 0.5 (10:1 hexane/ethyl acetate)

$^1$H NMR (CDCl$_3$, 400 MHz) δ7.74 (d, 1H, J=8.4 Hz), 7.45-7.52 (m, 2H), 7.39 (dd, 1H, J=1.6, 8.4 Hz), 7.20-7.28 (m, 3H), 7.10 (d, 1H, J=7.2 Hz), 7.02 (dd, 1H, J=1.6, 7.2 Hz), 3.74-3.78 (m, 4H), 3.24-3.28 (m, 4H), LC-MS: r.t. 3.15 min., m/z 314 (M+1).

Example 16

Synthesis of 3-(4-(2,3-dimethylphenyl)piperazin-1-yl)benzo[d]isoxazole (Compound 161)

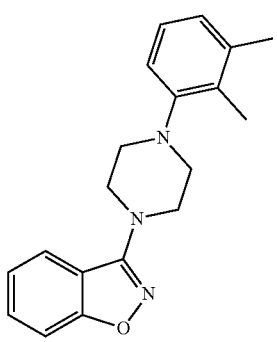 [SMILES: Cc1cccc(N2CCN(c3noc4ccccc34)CC2)c1C]

A solution of 3-chlorobenzo[d]isoxazole (50 mg, 0.326 mmol) and 1-(2,3-dimethylphenyl)piperazine (62 mg, 0.326 mmol) in pyridine (1 mL) was heated with stirring at 180° C. for 30 minutes with microwaves. The solvent was distilled off under reduced pressure, and the residue was purified by preparative silica gel column chromatography (ethyl acetate/hexane) to give 2.4 mg of the title compound.

Rf: 0.8 (5:1 hexane/ethyl acetate), $^1$H NMR (CDCl$_3$, 400 MHz) δ7.73 (d, 1H, J=8.0 Hz), 7.44-7.52 (m, 2H), 7.22 (dd, 1H, J=1.6, 8.0 Hz), 7.10 (d, 1H, J=8.0 Hz), 6.92-6.97 (m, 2H), 3.64-3.81 (m, 4H), 3.05-3.12 (m, 4H), 2.28 (s, 3H), 2.27 (S, 3H), LC-MS: r.t. 3.34 min., m/z 308 (M+1).

Example 17

Synthesis of 3-(4-(2,4-dichlorophenyl)piperazin-1-yl)benzo[d]isoxazole (Compound 171)

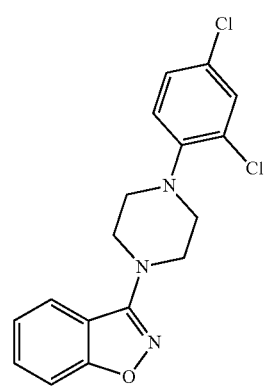 [SMILES: Clc1ccc(N2CCN(c3noc4ccccc34)CC2)c(Cl)c1]

A solution of 3-chlorobenzo[d]isoxazole (55 mg, 0.358 mmol) and 1-(2,4-dichlorophenyl)piperazine (190 mg, 0.822 mmol) in dimethoxyethane (0.5 mL) was heated with stirring at 160° C. for 120 minutes with microwaves. The solvent was distilled off under reduced pressure, and the residue was purified by preparative silica gel column chromatography (ethyl acetate/hexane) to give 13.3 mg of the title compound.

$^1$H NMR (CDCl$_3$, 400 MHz) δ7.71 (d, 1H, J=8.4 Hz), 7.49 (t, 1H, J=8.0 Hz), 7.46 (d, 1H, J=8.0 Hz), 7.39 (d, 2H, J=2.4 Hz), 7.19-7.24 (m, 2H), 7.00 (d, 1H, J=8.4 Hz), 3.72-3.77 (m, 4H), 3.19-3.23 (m, 4H), LC-MS: r.t. 3.40 min., m/z 348 (M+1).

Example 18

Synthesis of 3-(4-(3-chloropyridin-2-yl)piperazin-1-yl)benzo[d]isothiazole (Compound 181)

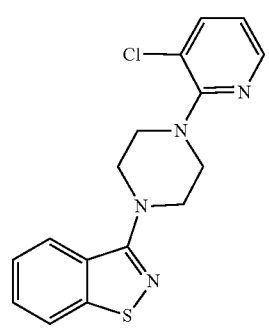 [SMILES: Clc1cccnc1N1CCN(c2nsc3ccccc23)CC1]

A solution of 2-bromo-3-chloropyridine (96 mg, 0.5 mmol), 3-(piperazin-1-yl)benzo[d]isothiazole (110 mg, 0.5 mmol), tris(dibenzylideneacetone)dipalladium(0) (Pd$_2$(dba)$_3$, 46.8 mg, 0.05 mmol), sodium tert-butoxide (57.7 mg, 0.6 mmol), and (2,2'-bis(diphenylphosphanyl)-1,1'-binaphthalene (62.3 mg, 0.1 mmol) in dioxane (10 mL) was heated with stirring at 90° C. for 9 hours. The mixture was extracted with ethyl acetate. The organic layer was dried over magnesium sulfate, and the solvent was distilled off under reduced pressure. The residue was purified by preparative silica gel column chromatography (ethyl acetate/hexane) to give 42 mg of the crude title compound. This compound was further washed with warmed acetonitrile to give 44.6 mg of the title compound.

Rf=0.75 (2:1 hexane/ethyl acetate)

$^1$H NMR (CDCl$_3$, 400 MHz) δ8.22 (d, 1H, J=4.8 Hz), 7.96 (d, 1H, J=8.0 Hz), 7.83 (d, 1H, J=8.0 Hz), 7.62 (d, 1H, J=8.0 Hz), 7.48 (t, 1H, J=8.0 Hz), 7.38 (t, 1H, J=8.0 Hz), 6.88 (dd, 1H, J=4.8, 8.0 Hz), 3.69-3.73 (m, 4H), 3.58-3.62 (m, 4H), LC-MS: r.t. 2.86 min., m/z 331 (M+1).

Example 19

Synthesis of 5-chloro-6-(8-(4-(trifluoromethyl) benzo[d]isoxazol-3-yl)-3,8-diazabicyclo[3,2,1]octan-3-yl)nicotinic acid (Compound 191)

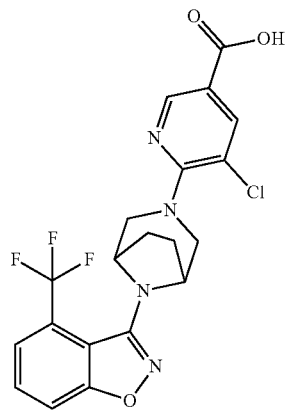 [SMILES: O=C(O)c1cnc(N2CC3CCC(C2)N3c2noc3cccc(C(F)(F)F)c23)c(Cl)c1]

Step 19-1

A solution of tert-butyl(1R,5S)-3,8-diazabicyclo[3,2,1] octane-8-carboxylate (0.5 g, 2.355 mmol) and 5,6-dichloronicotinic acid (0.452 g, 2.355 mmol) in pyridine (5 mL) was heated with stirring at 90° C. for 10 hours. The solution was diluted with purified water and then neutralized with 10% KHSO$_4$ to adjust the pH to about 6. The resulting solid was collected by filtration, washed with purified water, and dried under reduced pressure to give 248 mg of crude 6-(8-(tert-butoxycarbonyl)-3,8-diazabicyclo[3,2,1]octan-3-yl)-5-chloronicotinic acid. The obtained crude 6-(8-(tert-butoxycarbonyl)-3,8-diazabicyclo[3,2,1]octan-3-yl)-5-chloronicotinic acid was used in the next step without purification.

Step 19-2

Excess thionyl chloride was added at room temperature to a solution of crude 6-(8-(tert-butoxycarbonyl)-3,8-diazabicyclo[3,2,1]octan-3-yl)-5-chloronicotinic acid described above (227 mg, 0.617 mmol) in methanol (5 mL), and the mixture was allowed to stand overnight. The reaction mixture was concentrated to dryness to give 208.2 mg of crude 6-(3,8-diazabicyclo[3,2,1]octan-3-yl)-5-chloronicotinic acid hydrochloride. The obtained crude 6-(3,8-diazabicyclo[3,2,1]octan-3-yl)-5-chloronicotinic acid hydrochloride was used in the next step without purification.

Step 19-3

A solution (0.5 mL) of about 1 N 2-fluoro-N-hydroxy-6-(trifluoromethyl)benzimidoyl chloride in DMF was added at room temperature to a solution of crude 6-(3,8-diazabicyclo[3,2,1]octan-3-yl)-5-chloronicotinic acid hydrochloride described above (152 mg, 0.5 mmol) and triethylamine (279 µL, 2.0 mmol) in DMF (1.5 mL), and the mixture was stirred overnight. The resulting mixture was diluted with purified water, neutralized with 10% KHSO$_4$ to adjust the pH to about 6, and extracted with ethyl acetate. The organic layer was dried over magnesium sulfate, and the solvent was distilled off under reduced pressure. The residue was purified by preparative silica gel column chromatography (ethyl acetate/hexane) to give 136.4 mg of 5-chloro-6-(8-((2-fluoro-6-(trifluoromethyl)phenyl(hydroxyimino)methyl)-3,8-diazabicyclo[3,2,1]octan-3-yl)nicotinic acid (Compound 192) (LC-MS: r.t. 2.54 min., m/z 473 (M+1)). (Rf=0.1, 2:1 ethyl acetate/hexane).

Step 19-4

A mixed solution of a 2 N aqueous potassium hydroxide solution (0.6 mL) of 5-chloro-6-(8-((2-fluoro-6-(trifluoromethyl)phenyl(hydroxyimino)methyl)-3,8-diazabicyclo[3,2,1]octan-3-yl)nicotinic acid (90 mg) and dioxane (1.8 mL) was heated with stirring at 100° C. for 10 hours. LC/MS analysis showed about 95% conversion. The reaction solution was diluted with purified water and then neutralized with 1 N hydrochloric acid and 10% KHSO$_4$ to adjust the pH to about 6, followed by extraction with ethyl acetate. The organic layer was dried over magnesium sulfate, and the solvent was distilled off under reduced pressure. The residue was purified by preparative silica gel column chromatography (ethyl acetate/hexane). The resulting solid was collected by filtration, washed with warm isopropanol, and dried to give 16.3 mg of the title compound.

Rf=0.25 (2:1 ethyl acetate/hexane)

$^1$H NMR (DMSO, 400 MHz) δ8.63 (dd, 1H, J=0.8, 1.6 Hz), 8.07-8.11 (m, 2H), 7.83-7.87 (m, 2H), 4.85-4.88 (br, 2H), 3.33-3.38 (m, 6H), 2.13 (dd, 2H, J=12.8, 6.0 Hz), 1.91-1.99 (m, 2H), LC-MS: r.t. 3.21 min., m/z 453 (M+1).

Example 20

Synthesis of 7-chloro-3-(4-(2-chlorophenyl)piperazin-1-yl)benzo[d]isoxazole (Compound 201)

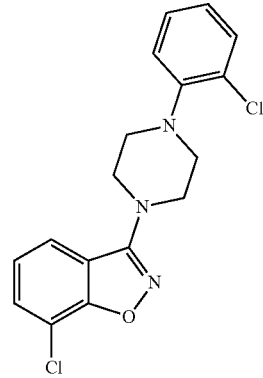 [SMILES: Clc1ccccc1N1CCN(c2noc3c(Cl)cccc23)CC1]

(E)-(4-(2-chlorophenyl)piperazin-1-yl)(2,3-dichlorophenyl)methanone oxime and its Z-isomer were obtained according to the procedures of step 6-1 and step 6-2 in Example 6, except that 2,3-dichlorobenzaldehyde was used in place of 2,6-dichlorobenzaldehyde.

(E)-(4-(2-chlorophenyl)piperazin-1-yl)(2,3-dichlorophenyl)methanone oxime (Compound 202(E))

Rf: 0.5, 3:1 hexane/ethyl acetate,
¹H NMR (CDCl₃, 400 MHz) δ7.52 (dd, 1H, J=1.2, 8.0 Hz), 7.36 (dd, 1H, J=1.2, 8.0 Hz), 7.32 (dd, 1H, J=2.0, 8.0 Hz), 7.25 (dd, 1H, J=2.0, 8.0 Hz), 7.21 (dd, 1H, J=2.0, 8.0 Hz), 7.04 (dd, 1H, J=2.0, 8.0 Hz), 6.98 (dt, 1H, J=1.2, 8.0 Hz), 3.50-3.54 (m, 4H), 3.07-3.11 (m, 4H), LC-MS: r.t. 3.08 min., m/z 384 (M+1)

(Z)-(4-(2-chlorophenyl)piperazin-1-yl)(2,3-dichlorophenyl) methanone oxime (Compound 202 (Z))

Rf: 0.3, 3:1 hexane/ethyl acetate
¹H NMR (CDCl3, 400 MHz) δ7.52 (dd, 1H, J=1.2, 8.0 Hz), 7.36 (d, 1H, J=8.0 Hz), 7.31 (t, 1H, J=8.0 Hz), 7.25 (d, 1H, J=8.0 Hz), 7.21 (d, 1H, J=8.0 Hz), 7.02 (d, 1H, J=8.0 Hz), 6.99 (t, 1H, J=8.0 Hz), 5.77-5.89 (br, 1H), 3.21-3.40 (m, 4H), 3.03-3.07 (m, 4H), LC-MS: r.t. 3.08 min., m/z 384 (M+1).

The title compound was obtained according to the procedure of step 6-3 of Example 6, except that (E)-(4-(2-chlorophenyl) piperazin-1-yl)(2,3-dichlorophenyl) methanone oxime was used in place of (E)-(4-(2-chlorophenyl)piperazin-1-yl)(2,6-dichlorophenyl) methanone oxime.

¹H NMR (CDCl₃, 400 MHz) δ7.63 (d, 1H, J=8.8 Hz), 7.50 (d, 1H, J=7.6 Hz), 7.42 (dd, 1H, J=1.2, 7.6 Hz), 7.26 (dt, 1H, J=1.2, 7.6 Hz), 7.20 (t, 1H, J=7.6 Hz), 7.08 (dd, 1H, J=1.2, 7.6 Hz), 7.02 (dt, 1H, J=1.2, 7.6 Hz), 3.74-3.78 (m, 4H), 3.23-3.28 (m, 4H), LC-MS: r.t. 3.38 min., m/z 384 (M+1).

Example 21

Synthesis of 6-chloro-3-(4-(2-chlorophenyl)piperazin-1-yl)benzo[d]isoxazole (Compound 211)

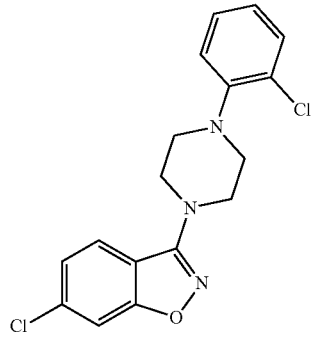 [SMILES: Clc1ccc2c(N3CCN(c4ccccc4Cl)CC3)noc2c1]

(E)-(4-(2-chlorophenyl)piperazin-1-yl)(2,4-dichlorophenyl)methanone oxime and its Z-isomer were obtained according to the procedures of step 6-1 and step 6-2 in Example 6, except that 2,4-dichlorobenzaldehyde was used in place of 2,6-dichlorobenzaldehyde.

(E)-(4-(2-chlorophenyl)piperazin-1-yl)(2,4-dichlorophenyl)methanone oxime (Compound 212(E))

Rf: 0.5 (3:1 hexane/ethyl acetate)
¹H NMR (CDCl₃, 400 MHz) δ7.41 (d, 1H, J=1.6 Hz), 7.39 (s, 1H), 7.36 (dd, 1H, J=1.6, 8.0 Hz), 7.30 (dd, 1H, J=7.2, 8.8 Hz), 7.21 (dd, 1H, J=1.2, 7.2 Hz), 7.03 (dd, 1H, J=2.0, 8.0 Hz), 6.98 (dt, 1H, J=1.2, 8.0 Hz), 5.72 (br, 1H), 3.35-3.40 (m, 4H), 3.04-3.09 (m, 4H), LC-MS: r.t. 3.03 min., m/z 384 (M+1).

(Z)-(4-(2-chlorophenyl)piperazin-1-yl)(2,4-dichlorophenyl)methanone oxime (Compound 212(Z))

Rf: 0.3 (3:1 hexane/ethyl acetate)
¹H NMR (CDCl₃, 400 MHz) δ7.36 (dd, 1H, J=1.2, 7.2 Hz), 7.35 (d, 1H, J=1.2, 8.0 Hz), 7.26 (dd, 1H, J=1.2, 8.0 Hz), 7.28 (dd, 1H, J=2.0, 8.0 Hz), 7.22 (dt, 1H, J=1.2, 7.2 Hz), 7.04 (dd, 1H, J=8.0 Hz), 6.97 (dt, 1H, J=1.2, 8.0 Hz), 6.46 (br, 1H), 3.53-3.57 (m, 4H), 3.09-3.13 (m, 4H), LC-MS: r.t. 3.03 min., m/z 384 (M+1).

The title compound was obtained according to the procedure of step 6-3 in Example 6, except that (E)-(4-(2-chlorophenyl)piperazin-1-yl)(2,4-dichlorophenyl)methanone oxime was used in place of (E)-(4-(2-chlorophenyl)piperazin-1-yl)(2,6-dichlorophenyl)methanone oxime.

¹H NMR (CDCl₃, 400 MHz) δ7.64 (d, 1H, J=8.8 Hz), 7.49 (d, 1H, J=2.0 Hz), 7.40 (dd, 1H, J=1.6, 8.0 Hz), 7.26 (dt, 1H, J=1.2, 7.6 Hz), 7.22 (dd, 1H, J=2.0, 8.8 Hz), 7.08 (dd, 1H, J=1.6, 8.0 Hz), 7.02 (dt, 1H, J=1.2, 7.6 Hz), 3.72-3.76 (m, 4H), 3.23-3.27 (m, 4H), LC-MS: r.t. 3.42 min., m/z 384 (M+1).

Example 22

Synthesis of 5-chloro-6-(4-(4-chlorobenzo[d]isoxazol-3-yl)piperazin-1-yl)pyridin-3-yl)(morpholino)methanone (Compound 221)

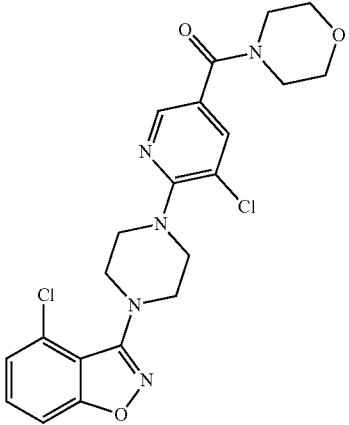 [SMILES: O=C(c1cnc(N2CCN(c3noc4cccc(Cl)c34)CC2)c(Cl)c1)N1CCOCC1]

The title compound was obtained according to the procedure of Example 2, except that 5-chloro-6-(4-(4-chlorobenzo[d]isoxazol-3-yl)piperazin-1-yl)nicotinic acid (Compound 081) was used in place of 5-chloro-6-(4-(4-(trifluoromethyl)benzo[d]isoxazol-3-yl)piperazin-1-yl) nicotinic acid, and morpholine was used in place of methylamine.

¹H NMR (CDCl₃, 400 MHz) δ8.34 (d, 1H, J=2.0 Hz), 8.25 (d, 1H, J=1.6 Hz), 7.73 (d, 1H, J=1.6 Hz), 7.43 (dd, 1H, J=7.2, 8.4 Hz), 7.40 (dd, 1H, J=1.6, 8.4 Hz), 7.26 (dd, 1H, J=1.2, 6.8 Hz), 3.57-3.85 (m, 12H), LC-MS: r.t. 2.80 min., m/z 413 (M+1).

Example 23

Synthesis of 5-chloro-6-(4-(4-chlorobenzo[d]isoxazol-3-yl)piperazin-1-yl)-N-(methylsulfonyl) nicotinamide (Compound 231)

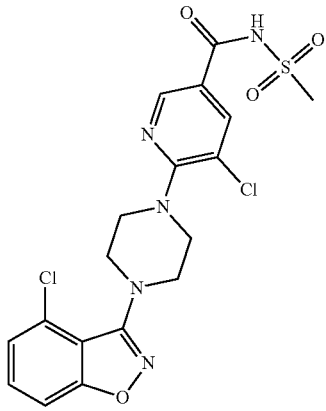 [SMILES: CS(=O)(=O)NC(=O)c1cnc(N2CCN(c3noc4cccc(Cl)c34)CC2)c(Cl)c1]

A solution of 5-chloro-6-(4-(4-chlorobenzo[d]isoxazol-3-yl)piperazin-1-yl)nicotinic acid (Compound 081, 79 mg, 0.2 mmol), methanesulfonamide (28.5 mg, 0.3 mmol), DMAP (4-dimethylaminopyridine, 36.7 mg, 0.3 mmol), and EDC (N-(3-dimethylaminopropyl)-N'-ethylcarbodiimide hydrochloride, 57.5 mg, 0.3 mmol) in dichloromethane (1 mL) was stirred at room temperature overnight. The pH of the reaction mixture was adjusted to about 3 with 10% KHSO$_4$ and a saturated aqueous sodium hydrogencarbonate solution, followed by extraction with ethyl acetate. The organic layer was dried over magnesium sulfate, and the solvent was distilled off under reduced pressure. The residue was purified by preparative silica gel column chromatography (ethyl acetate/hexane) to give 40.1 mg of the title compound.

Rf=0.3, 5% methanol/ethyl acetate $^1$H NMR (DMSO, 400 MHz) δ8.67 (s, 1H), 8.12 (s, 1H), 7.67 (d, 1H, J=8 Hz), 7.63 (t, 1H, J=8 Hz), 7.45 (d, 1H, J=7.2 Hz), 3.53-3.58 (m, 4H), 3.47-3.52 (m, 4H), LC-MS: r.t. 2.78 min., m/z 470 (M+1).

Example 24

Synthesis of methyl 5-chloro-6-(4-(4-(trifluoromethyl)benzo[d]isoxazol-3-yl)piperazin-1-yl) nicotinate (Compound 241)

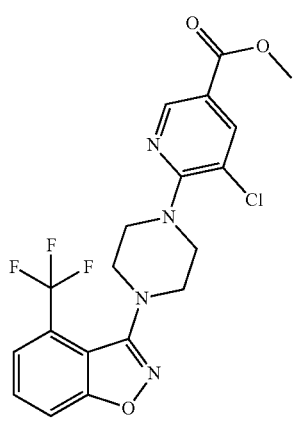

A 1 N hydrogen chloride methanol solution (12 mL) of 5-chloro-6-(4-(4-(trifluoromethyl)benzo[d]isoxazol-3-yl)piperazin-1-yl)nicotinic acid (Compound 011, 110 mg) was heated with stirring at 68° C. for 24 hours. LC/MS analysis showed about 90% conversion. The reaction mixture was concentrated, diluted with purified water, and neutralized with a saturated aqueous sodium hydrogencarbonate solution, followed by extraction with ethyl acetate. The organic layer was dried over magnesium sulfate, and the solvent was distilled off under reduced pressure. The residue was purified by preparative silica gel column chromatography (ethyl acetate/hexane) to give 84.9 mg of the title compound.

(Rf=0.5, 2:1 hexane/ethyl acetate). $^1$H NMR (CDCl$_3$, 400 MHz) δ8.77 (d, 1H, J=2.0 Hz), 8.16 (d, 1H, J=2.0 Hz), 7.74 (dd, 1H, J=1.2, 7.2 Hz), 7.66 (dd, 1H, J=1.2, 8.0 Hz), 7.63 (t, 1H, J=6.8 Hz), 3.92 (s, 3H), 3.75-3.78 (m, 4H), 3.44-3.48 (m, 4H), LC-MS: r.t. 2.21 min., m/z 423 (M+1).

Example 25

Synthesis of (5-chloro-6-(4-(4-(trifluoromethyl)benzo[d]isoxazol-3-yl)piperazin-1-yl) pyridin-3-yl)methanol (Compound 251)

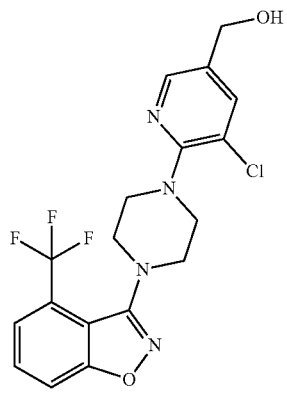 [SMILES: OCc1cnc(N2CCN(c3noc4cccc(C(F)(F)F)c34)CC2)c(Cl)c1]

Isopropanol (0.08 mL) was added to a solution of methyl 5-chloro-6-(4-(4-(trifluoromethyl)benzo[d]isoxazol-3-yl)piperazin-1-yl)nicotinate (Compound 241, 24 mg) and sodium borohydride (4 mg) in THF, and the mixture was heated with stirring at 65° C. for 4 hours. Methanol was added to the reaction mixture, and the mixture was concentrated. The residue was purified by preparative silica gel column chromatography (ethyl acetate/hexane) to give 4.7 mg of the title compound.

Rf=0.27, 1:1 hexane/ethyl acetate $^1$H NMR (CDCl$_3$, 400 MHz) δ8.18 (d, 1H, J=2.0 Hz), 7.73 (dd, 1H, J=1.2, 8 Hz), 7.69 (d, 1H, J=2.0 Hz), 7.65 (d, 1H, J=8 Hz), 7.62 (t, 1H, J=8 Hz), 4.66 (d, 2H, J=4.8 Hz), 3.55-3.59 (m, 4H), 3.45-3.49 (m, 4H), LC-MS: r.t. 3.23 min., m/z 413 (M+1).

Example 26

Synthesis of 3-(4-(3-methylpyridin-2-yl)piperazin-1-yl)-4-(trifluoromethyl)benzo[d]isoxazole (Compound 261)

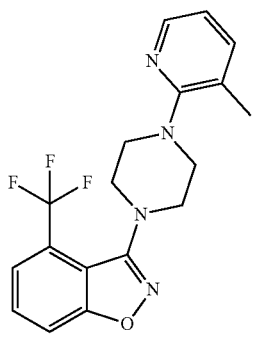 [SMILES: Cc1cccnc1N1CCN(c2noc3cccc(C(F)(F)F)c23)CC1]

The title compound was obtained according to the procedures of step 1-3 and step 1-4 in Example 1, except that 1-(3-methylpyridin-2-yl)piperazine was used in place of 5-chloro-6-(piperazin-1-yl)nicotinic acid hydrochloride.

$^1$H NMR (CDCl$_3$, 400 MHz) δ8.20 (dd, 1H, J=2.0, 5.2 Hz), 7.73 (dd, 1H, J=1.2, 8 Hz), 7.65 (d, 1H, J=8 Hz), 7.61 (t, 1H, J=8 Hz), 7.44 (d, 1H, J=7.2 Hz), 6.89 (dd, 1H, J=5.2, 7.2 Hz), 3.45-3.49 (m, 4H), 3.34-3.38 (m, 4H), 2.33 (s, 3H).

LC-MS: r.t. 2.42 min., m/z 363 (M+1).

Example 27

Synthesis of 4-methoxy-3-(4-(2-chlorophenyl)piperazin-1-yl)benzo[d]isoxazole (Compound 271)

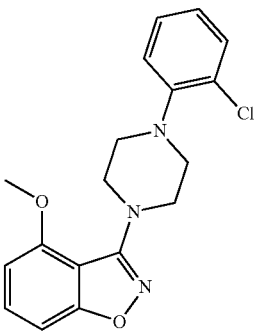 [SMILES: COc1cccc2onc(N3CCN(c4ccccc4Cl)CC3)c12]

The title compound was obtained according to the procedure of Example 1, except that 2-fluoro-6-(methoxy)benzaldehyde was used in place of 2-fluoro-6-(trifluoromethyl)benzaldehyde.

Rf: 0.6 (2:1 hexane/ethyl acetate), $^1$H NMR (CDCl$_3$, 400 MHz) δ7.43 (t, 1H, J=8.0 Hz), 7.39 (dd, 1H, J=1.2, 8.0 Hz), 7.25 (dt, 1H, J=1.2, 8.4 Hz), 7.11 (dd, 1H, J=1.2, 8.4 Hz), 7.00 (dt, 1H, J=1.6, 8.0 Hz), 6.62 (d, 1H, J=8.4 Hz), 3.97 (s, 3H), 3.68-3.73 (m, 4H), 3.24-3.28 (m, 4H), LC-MS: r.t. 3.21 min., m/z 344 (M+1).

Example 28

Synthesis of 1-(1-(4-(trifluoromethyl)benzo[d]isoxazol-3-yl)piperidin-4-yl)-1,3-dihydro-2H-benzo[d]imidazol-2-one (Compound 281)

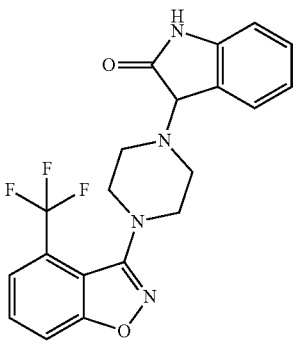 [SMILES: O=C1Nc2ccccc2C1N1CCN(c2noc3cccc(C(F)(F)F)c23)CC1]

The title compound was obtained according to the procedures of step 1-3 and step 1-4 of Example 1, except that 1-(piperidin-4-yl)-1,3-dihydro-2H-benzo[d]imidazol-2-one was used in place of 5-chloro-6-(piperazin-1-yl)nicotinic acid hydrochloride.

$^1$H NMR (CDCl$_3$, 400 MHz) δ7.88 (br, 1H), 7.74 (d, 1H, J=8 Hz), 7.67 (d, 1H, J=6.4 Hz), 7.63 (t, 1H, J=8 Hz), 7.30 (d, 1H, J=7.6 Hz), 7.05-7.16 (m, 3H), 4.65 (tt, 1H, J=12, 4.8 Hz), 3.79 (d, 2H, J=10.4 Hz), 3.16 (t, 2H, J=11.6 Hz), 2.69 (dq, 2H, J=4, 12 Hz), 1.96 (d, 2H, J=12 Hz), LC-MS: r.t. 2.68 min., m/z 403 (M+1).

In step 1-3 in the course of synthesis, 1-(1-((2-fluoro-6-(trifluoromethyl)phenyl(hydroxyimino)methyl) piperidin-4-yl)-1,3-dihydro-2H-benzo[d]imidazol-2-one was obtained (Compound 282; LC-MS: r.t. 2.20 min., m/z 423 (M+1)).

Example 29

Synthesis of 2-(2-oxo-3-(1-(4-(trifluoromethyl)benzo[d]isoxazol-3-yl)piperidin-4-yl)-2,3-dihydro-1H-benzo[d]imidazol-1-yl)acetic acid tert-butyl ester (Compound 291)

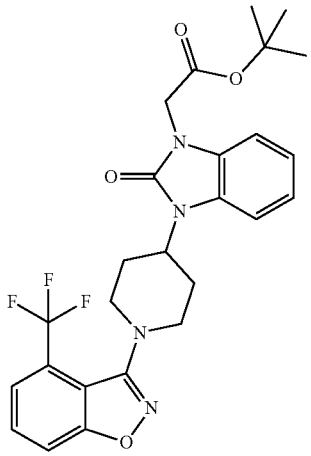 [SMILES: CC(C)(C)OC(=O)Cn1c(=O)n(C2CCN(c3noc4cccc(C(F)(F)F)c34)CC2)c2ccccc21]

A solution of 1-(1-(4-(trifluoromethyl)benzo[d]isoxazol-3-yl)piperidin-4-yl)-1,3-dihydro-2H-benzo[d]imidazol-2-one (Compound 281, 67 mg, 0.171 mmol), bromoacetic acid tert-butyl ester (50 mg, 0.256 mmol), and 60% sodium hydride (10.4 mg, 0.256 mmol) in DMF (1 mL) was stirred at room temperature for 2 hours, and saturated saline was added, followed by extraction with ethyl acetate. The organic layer was dried over magnesium sulfate, filtered, and concentrated. The residue was purified by preparative liquid silica gel column chromatography (hexane/ethyl acetate) to give the title compound (86.6 mg).

$^1$H NMR (CDCl$_3$, 400 MHz) δ7.55 (d, 1H, J=8 Hz), 7.67 (d, 1H, J=6.4 Hz), 7.43 (t, 1H, J=8 Hz), 7.31 (d, 1H, J=7.6 Hz), 7.13 (t, 1H, J=7.2 Hz), 7.10 (t, 1H, J=7.2 Hz), 6.90 (d, 1H, J=7.2 Hz), 4.65 (tt, 1H, J=12, 4.8 Hz), 4.55 (s, 2H), 3.77 (d, 2H, J=10.4 Hz), 3.15 (t, 2H, J=11.6 Hz), 2.70 (dq, 2H, J=4, 12 Hz), 1.96 (d, 2H, J=12 Hz), 1.46 (s, 9H), LC-MS: r.t. 3.25 min., m/z 517 (M+1).

Example 30

Synthesis of 2-(2-oxo-3-(1-(4-(trifluoromethyl)benzo[d]isoxazol-3-yl)piperidin-4-yl)-2,3-dihydro-1H-benzo[d]imidazol-1-yl)acetic acid (Compound 301)

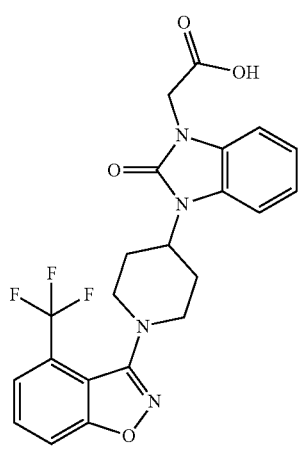 [SMILES: O=C(O)Cn1c(=O)n(C2CCN(c3noc4cccc(C(F)(F)F)c34)CC2)c2ccccc21]

2-(2-Oxo-3-(1-(4-(trifluoromethyl)benzo[d]isoxazol-3-yl)piperidin-4-yl)-2,3-dihydro-1H-benzo[d]imidazol-1-yl) acetic acid tert-butyl ester (Compound 291, 78.3 mg) was dissolved in dimethyl ether (DME, 5 mL), and a 1 N aqueous sodium hydroxide solution (2 mL) was added, followed by stirring at room temperature for 2 hours. The resulting mixture was neutralized with 1 N hydrochloric acid, and the precipitated crystals were collected by filtration, washed with purified water, and dried to give the title compound (50.8 mg).

$^1$H NMR (DMSO, 400 MHz) δ8.06-8.11 (m, 1H), 7.87 (d, 1H, J=7.6 Hz), 7.84 (t, 1H, J=3.6 Hz), 7.31 (d, 1H, J=7.2 Hz), 7.17 (t, 1H, J=7.2 Hz), 7.10 (dt, 1H, J=1.2, 7.2 Hz), 7.06 (dt, 1H, J=1.2, 7.2 Hz), 4.60 (s, 2H), 4.50 (tt, 1H, J=12, 4 Hz), 3.12 (t, 2H, J=12 Hz), 2.55-2.68 (m, 2H), 1.84 (d, 2H, J=12 Hz), LC-MS: r.t. 2.65 min., m/z 461 (M+1).

Example 31

Synthesis of 3-(4-(2-chloropyridin-3-yl)piperazin-1-yl)benzo[d]isoxazole (Compound 311)

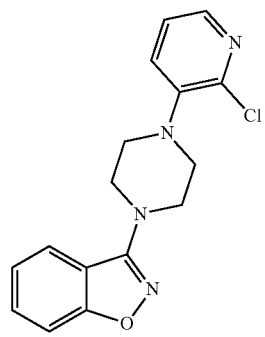 [SMILES: Clc1ncccc1N1CCN(c2noc3ccccc23)CC1]

The title compound was obtained according to the procedure of Example 14, except that 1-(2-chloropyridin-3-yl)piperazine was used in place of 1-(pyridin-2-yl)piperazine.

LC-MS: r.t. 2.60 min., m/z 315 (M+1).

Example 32

Synthesis of 3-(4-(3-chloropyridin-2-yl)piperazin-1-yl)benzo[d]isoxazole (Compound 321)

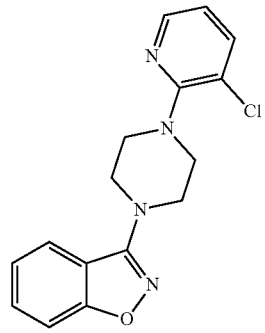 [SMILES: Clc1cccnc1N1CCN(c2noc3ccccc23)CC1]

The title compound was obtained according to the procedure of Example 14, except that 1-(3-chloropyridin-2-yl)piperazine was used in place of 1-(pyridin-2-yl)piperazine.

LC-MS: r.t. 2.89 min., m/z 315 (M+1).

Example 33

Synthesis of 3-(4-(3,5-dichlorophenyl)piperazin-1-yl)benzo[d]isoxazole (Compound 331)

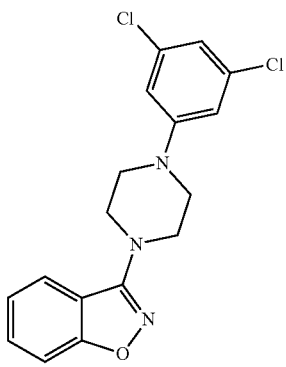 [SMILES: Clc1cc(Cl)cc(N2CCN(c3noc4ccccc34)CC2)c1]

The title compound was obtained according to the procedure of Example 17, except that 1-(3,5-dichlorophenyl)piperazine was used in place of 1-(2,4-dichlorophenyl)piperazine.

LC-MS: r.t. 3.40 min., m/z 348 (M+1)

Example 34

Synthesis of methyl 5-chloro-6-(1-(4-(trifluoromethyl)benzo[d]isoxazol-3-yl)piperidin-4-yl) nicotinate (Compound 341)

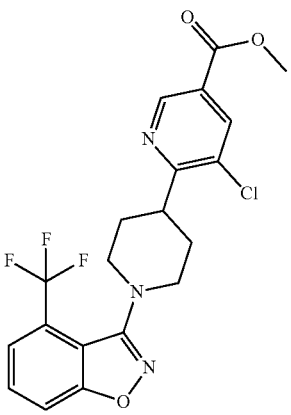 [SMILES: COC(=O)c1cnc(C2CCN(c3noc4cccc(C(F)(F)F)c34)CC2)c(Cl)c1]

Step 34-1 tert-Butyl 4-(4,4,5,5-tetramethyl-1,3,2-dioxaborolan-2-yl)-3,6-dihydropyridine-1(2H)-carboxylate (618 mg, 2 mmol), 5,6-dichloronicotinic acid (384 mg, 2 mmol), potassium carbonate (691 mg, 5 mmol), and bistriphenylphosphinepalladium dichloride (140 mg, 0.2 mmol) were added to a mixture of dimethoxyethane, ethanol, and water (1:1:1 volume ratio) (12 mL), and the resulting mixture was heated at 90° C. for 2 hours in a nitrogen atmosphere. A 10% aqueous potassium hydrogen sulfate solution was added to the reaction solution, followed by extraction with ethyl acetate. The organic layer was dried over magnesium sulfate, and the solvent was distilled off under reduced pressure. The residue was purified by preparative diol silica gel column chromatography (5% methanol/ethyl acetate) to give 696 mg of 1'-(tert-butoxycarbonyl)-3-chloro-1',2',3',6'-tetrahydro-[2,4'-bipyridine]-5-carboxylic acid (yield: 103%).

$^1$H NMR (DMSO, 400 MHz) δ8.95 (d, 1H, J=1.6 Hz), 8.27 (d, 1H, J=1.6 Hz), 6.25-6.33 (m, 1H), 4.02-4.08 (m, 2H), 3.51-3.57 (m, 2H), 3.3 (m, 2H), 1.44 (s, 9H).

LC-MS: r.t. 2.78 min., m/z 284 (M+1-C4H8).

Step 34-2

1'-(tert-Butoxycarbonyl)-3-chloro-1',2',3',6'-tetrahydro-[2,4'-bipyridine]-5-carboxylic acid (696 mg, 2 mmol) was added to methanol (5 mL). Subsequently, excess thionyl chloride was added, and the mixture was heated at 45° C. for 3 hours. The resulting mixture was concentrated to give methyl 3-chloro-1',2',3',6'-tetrahydro-[2,4'-bipyridine]-5-carboxylate hydrochloride. The obtained methyl 3-chloro-1',2',3',6'-tetrahydro-[2,4'-bipyridine]-5-carboxylate hydrochloride was used in the next step without purification.

LC-MS: r.t. 1.55 min., m/z 253 (M+1).

Step 34-3

Methyl 3-chloro-1',2',3',6'-tetrahydro-[2,4'-bipyridine]-5-carboxylate hydrochloride (322 mg, 1.114 mmol) was dissolved in methanol (5 mL), and Pd/C (53 mg) was added. The mixture was stirred at room temperature for 1 hour in a hydrogen atmosphere. LC/MS confirmed the formation of methyl 5-chloro-6-(piperidin-4-yl)nicotinate hydrochloride (1.114 mmol) in the reaction liquid. The reaction product was filtered with Celite to remove Pd/C. The filtrate was concentrated and used in the next reaction.

LC-MS: r.t. 1.57 min., m/z 255 (M+1).

Step 34-4

The concentrate containing methyl 5-chloro-6-(piperidin-4-yl)nicotinate hydrochloride (1.114 mmol), and triethylamine (0.621 mL, 4.46 mmol) were added to DMF (3 mL) to prepare a first liquid. 1.114 mmol 2-fluoro-N-hydroxy-6-(trifluoromethyl)benzimidoyl chloride was added to DMF to prepare a second liquid (0.88235 mmol/mL in DMF). The total amount of the second liquid was added at room temperature to the total amount of the first liquid, and the mixture was stirred overnight. A saturated aqueous ammonium chloride solution was added to the reaction solution, followed by extraction with ethyl acetate. The organic layer was dried over magnesium sulfate, and the solvent was distilled off under reduced pressure. The residue was purified by preparative silica gel column chromatography (ethyl acetate/hexane) to give 12 mg of methyl 5-chloro-6-(1-((2-fluoro-6-(trifluoromethyl)phenyl)(hydroxyimino)methyl)piperidin-4-yl)nicotinate (Compound 342) as an E/Z mixture.

$^1$H NMR (DMSO, 400 MHz) δ9.48 (s, 1H), 8.99 (d, 1H, J=1.6 Hz), 8.27 (d, 1H, J=1.6 Hz), 7.59-7.73 (m, 3H), 3.89 (s, 3H), 3.54 (bd, 1H, J=14.8 Hz), 3.37-3.49 (m, 2H), 2.75-2.89 (m, 2H), 1.65-1.85 (m, 4H).

LC-MS: r.t. 3.49 min., m/z 460 (M+1).

Step 34-5

Methyl 5-chloro-6-(1-((2-fluoro-6-(trifluoromethyl)phenyl)(hydroxyimino)methyl)piperidin-4-yl)nicotinate (12 mg) and p-toluenesulfonic acid (1 mg) were added to DMSO (1 mL), and the mixture was heated at 80° C. for 1 hour. Diazabicycloundecene (DBU; 100 μL) was added thereto, and the mixture was heated at 100° C. for 90 minutes. A saturated aqueous ammonium chloride solution was added to the reaction solution, followed by extraction with ethyl acetate. The organic layer was dried over magnesium sulfate, and the solvent was distilled off under reduced pressure. The residue was purified by preparative silica gel column chromatography (ethyl acetate/hexane) to give 7.7 mg of the title compound.

¹H NMR (DMSO, 400 MHz) δ9.04 (d, 1H, J=1.6 Hz), 8.31 (d, 1H, J=1.6 Hz), 8.06 (dd, 1H, J=2.8, 6.4 Hz), 7.80-7.86 (m, 2H), 3.89 (s, 3H), 3.64 (bd, 2H, J=12.4 Hz), 3.44-3.52 (m, 1H), 3.06 (bt, 2H, J=11.2 Hz), 2.04 (dq, 2H, J=3.2, 11.6 Hz), 1.91 (bd, 2H, J=10.4 Hz).

LC-MS: r.t. 4.08 min., m/z 440 (M+1).

Example 35

Synthesis of 5-chloro-6-(1-(4-(trifluoromethyl)benzo[d]isoxazol-3-yl)piperidin-4-yl)nicotinic acid (Compound 351)

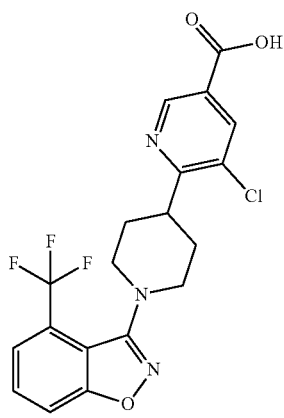

Methyl 5-chloro-6-(1-(4-(trifluoromethyl)benzo[d]isoxazol-3-yl)piperidin-4-yl) nicotinate (Compound 341; 7.7 mg) was added to dimethyl ether (DME; 1 mL). Subsequently, a 1 N aqueous sodium hydroxide solution (0.2 mL) was added, and the mixture was stirred at room temperature overnight. The resulting mixture was concentrated under reduced pressure and neutralized with 1 N hydrochloric acid (0.2 mL). The resulting powder was collected by filtration and dried under reduced pressure to give 3.1 mg of the title compound.

¹H NMR (DMSO, 400 MHz) δ8.94 (d, 1H, J=1.6 Hz), 8.18 (d, 1H, J=1.6 Hz), 8.03 (dd, 1H, J=2.8, 6.4 Hz), 7.77-7.83 (m, 2H), 3.60 (bd, 2H, J=12.4 Hz), 3.37-3.48 (m, 1H), 3.02 (bt, 2H, J=11.6 Hz), 2.02 (dq, 2H, J=3.2, 12.4 Hz), 1.86 (bd, 2H, J=11.2 Hz).

LC-MS: r.t. 3.66 min., m/z 426 (M+1).

Example 36

Synthesis of 3-(4-(2-chlorophenyl)-3,6-dihydropyridin-1(2H)-yl)-4-(trifluoromethyl)benzo[d]isoxazole (Compound 361)

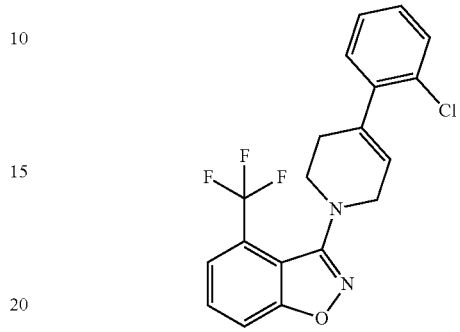

Step 36-1 tert-Butyl 4-(4,4,5,5-tetramethyl-1,3,2-dioxaborolan-2-yl)-3,6-dihydropyridin-1(2H)-carboxylate (309 mg, 1 mmol), 1-chloro-2-iodobenzene (238 mg, 1 mmol), potassium carbonate (207 mg, 1.5 mmol), and bistriphenylphosphinepalladium dichloride (70.2 mg, 0.1 mmol) were added to a mixture of dimethoxyethane and water (2:1 volume ratio) (12 mL), and the resulting mixture was heated at 90° C. for 1 hour in a nitrogen atmosphere. A 10% aqueous potassium hydrogen sulfate solution was added to the reaction solution, followed by extraction with ethyl acetate. The organic layer was dried over magnesium sulfate, and the solvent was distilled off under reduced pressure. The residue was purified by preparative silica gel column chromatography (hexane/ethyl acetate) to give 287.2 mg of tert-butyl 4-(2-chlorophenyl)-3,6-dihydropyridin-1(2H)-carboxylate (yield: 98%).

¹H NMR (CDCl3, 400 MHz) δ7.34-7.37 (m, 1H), 7.19-7.23 (m, 2H), 7.15-7.18 (m, 1H), 5.62-5.72 (br, 1H), 4.02-4.08 (br, 2H), 3.60-3.66 (bt, 2H, J=5.4 Hz), 2.41-2.48 (br, 2H), 1.50 (s, 9H).

LC-MS: r.t. 3.77 min., m/z 238 (M+1-C4H8).

Step 36-2 tert-Butyl 4-(2-chlorophenyl)-3,6-dihydropyridin-1(2H)-carboxylate (280.5 mg) was added to 4 N hydrochloric acid/ethyl acetate (5 mL), and the mixture was allowed to stand at room temperature overnight. The resulting mixture was concentrated to give 4-(2-chlorophenyl)-1,2,3,6-tetrahydropyridine hydrochloride. The obtained 4-(2-chlorophenyl)-1,2,3,6-tetrahydropyridine hydrochloride was used in the next step without purification.

LC-MS: r.t. 1.75 min., m/z 194 (M+1).

Step 36-3

4-(2-Chlorophenyl)-1,2,3,6-tetrahydropyridine hydrochloride (115 mg, 0.5 mmol) and triethylamine (0.209 mL, 1.5 mmol) were added to DMF (3 mL) to prepare a first liquid. 0.5 mmol 2-fluoro-N-hydroxy-6-(trifluoromethyl)benzimidoyl chloride was added to DMF to prepare a second liquid (0.88235 mmol/mL in DMF). The total amount of the second liquid was added at room temperature to the total amount of the first liquid, and the mixture was stirred for 1 hour. A saturated aqueous ammonium chloride solution was added to the reaction solution, followed by extraction with ethyl acetate. The organic layer was dried over magnesium sulfate, and the solvent was distilled off under reduced pressure to give 158.5 mg of (4-(2-chlorophenyl)-3,6-dihydropyridin-1(2H)-yl)(2-fluoro-6-(trifluoromethyl)phenyl)methanone oxime (Compound 362) as an E/Z mixture. 80 mg of the mixture was taken for use in the next reaction, and the rest was purified by preparative silica gel column chromatography (ethyl acetate/hexane) to give E-(4-(2-chlorophenyl)-3,6-dihydropyridin-1(2H)-yl)(2-fluoro-6-(trifluoromethyl)phenyl)methanone oxime (Compound 362(E)) and its Z-isomer (Compound 362(Z)).

(E)-(4-(2-chlorophenyl)-3,6-dihydropyridin-1(2H)-yl)(2-fluoro-6-(trifluoromethyl)phenyl)methanone oxime (27.6 mg, Rf=0.56)

$^1$H NMR (CDCl$_3$, 400 MHz) δ 7.52-7.61 (m, 2H), 7.32-7.41 (m, 2H), 7.16-7.25 (m, 3H), 6.25 (brs, 1H), 5.69 (brm, 1H), 3.84-3.99 (m, 2H), 3.17-3.31 (m, 2H), 2.33-2.49 (m, 2H).

LC-MS: r.t. 3.41 min., m/z 399 (M+1).

(Z)-(4-(2-chlorophenyl)-3,6-dihydropyridin-1(2H)-yl)(2-fluoro-6-(trifluoromethyl)phenyl)methanone oxime (17.1 mg, Rf=0.34)

$^1$H NMR (CDCl$_3$, 400 MHz) δ 7.51-7.59 (m, 2H), 7.31-7.39 (m, 2H), 7.15-7.23 (m, 3H), 6.25 (brs, 1H), 5.62 (brm, 1H), 3.91-4.15 (m, 2H), 3.50-3.58 (m, 2H), 2.45-2.51 (m, 2H).

LC-MS: r.t. 3.49 min., m/z 399 (M+1).

Step 36-4

(4-(2-Chlorophenyl)-3,6-dihydropyridin-1(2H)-yl)(2-fluoro-6-(trifluoromethyl)phenyl)methanone oxime (Compound 362, a mixture of E- and Z-isomers; 80 mg, 0.2 mmol) and p-toluenesulfonic acid (2 mg) were added to DMSO (1 mL), and the mixture was heated at 80° C. for 30 minutes. DBU (100 μL) was added thereto, and the mixture was heated at 100° C. for 90 minutes. A saturated aqueous ammonium chloride solution was added to the reaction solution, followed by extraction with ethyl acetate. The organic layer was dried over magnesium sulfate, and the solvent was distilled off under reduced pressure. The residue was purified by preparative silica gel column chromatography (ethyl acetate/hexane) to give 67.6 mg of the title compound (yield: 89%).

$^1$H NMR (CDCl$_3$, 400 MHz) δ 7.73 (d, 1H, J=8.0 Hz), 7.59-7.67 (m, 2H), 7.38 (dd, 1H, J=7.2, 2.0 Hz), 7.19-7.28 (m, 3H), 5.79-5.83 (m, 1H), 4.05 (dd, 2H, J=6, 2.8 Hz), 3.53 (t, 2H, J=7.6 Hz), 2.67-2.72 (m, 2H).

LC-MS: r.t. 4.22 min., m/z 379 (M+1).

Example 37

Synthesis of ethyl 5-chloro-6-(2-oxo-4-(4-(trifluoromethyl)benzo[d]isoxazol-3-yl)piperazin-1-yl)nicotinate (Compound 371)

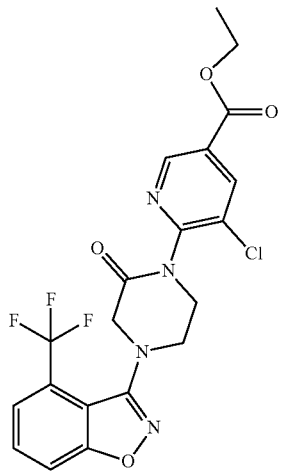 [SMILES: CCOC(=O)c1cnc(N2CCN(c3noc4cccc(C(F)(F)F)c34)CC2=O)c(Cl)c1]

Step 37-1 tert-Butyl 3-oxopiperazine-1-carboxylate (2.0 g, 9.99 mmol), ethyl 5,6-dichloronicotinate (2.3 g, 10.45 mmol), cesium carbonate (6.51 g, 19.98 mmol), Xantphos (578 mg, 0.999 mmol), and Pd$_2$(dba)$_3$ (457 mg, 0.499 mmol) were added to toluene (20 mL), and the mixture was heated at 120° C. for 3 hours in a nitrogen atmosphere. The reaction solution was passed through a silica gel pad, and the filtrate was concentrated. The residue was purified by preparative silica gel column chromatography (hexane/ethyl acetate) to give 2.67 g of tert-butyl 4-(3-chloro-5-(ethoxycarbonyl)pyridin-2-yl)-3-oxopiperazine-1-carboxylate (yield: 70%).

$^1$H NMR (CDCl$_3$, 400 MHz) δ 9.05 (d, 1H, J=1.6 Hz), 8.40 (d, 1H, J=1.6 Hz), 4.43 (q, 2H, J=7.2 Hz), 4.20-4.35 (m, 2H), 4.05 (brm, 1H), 3.84 (brm, 2H), 3.61 (brm, 1H), 1.50 (s, 9H), 1.41 (t, 3H, J=7.2 Hz).

LC-MS: r.t. 2.82 min., m/z 328 (M+1).

Step 37-2 tert-Butyl 4-(3-chloro-5-(ethoxycarbonyl)pyridin-2-yl)-3-oxopiperazine-1-carboxylate (369 mg, 0.961 mmol) was added to a 4 N hydrochloric acid/ethyl acetate mixture (5 mL), and the mixture was stirred at room temperature overnight. The resulting mixture was concentrated to dryness to give ethyl 5-chloro-6-(2-oxopiperazin-1-yl)nicotinate hydrochloride. The residue was used in the next step without purification.

$^1$H NMR (DMSO, 400 MHz) δ8.21 (br, 1H), 7.08 (br, 1H), 4.06 (br, 2H), 3.63 (q, 2H, J=7.2 Hz), 2.89-3.42 (brm, 4H), 0.61 (t, 3H, J=7.2 Hz).

LC-MS: r.t. 1.37 min., m/z 284 (M+1).

Step 37-3

Ethyl 5-chloro-6-(2-oxopiperazin-1-yl)nicotinate hydrochloride (296 mg, 0.925 mmol) and triethylamine (0.515 mL, 3.7 mmol) were added to DMF (6 mL) to prepare a first liquid. 0.925 mmol 2-fluoro-N-hydroxy-6-(trifluoromethyl)benzimidoyl chloride was added to DMF to prepare a second liquid (0.88235 mmol/mL in DMF). The second liquid was added at room temperature to the first liquid, and the mixture was stirred overnight. A 10% aqueous KHSO$_4$ solution was added to the reaction solution, followed by extraction with ethyl acetate. The organic layer was washed with an aqueous NaHCO$_3$ solution and dried over magnesium sulfate, and the solvent was distilled off under reduced pressure. The residue was purified by preparative silica gel column chromatography (ethyl acetate/hexane) to give ethyl (Z)-5-chloro-6-(4-((2-fluoro-6-(trifluoromethyl)phenyl)(hydroxyimino)methyl)-2-oxopiperazin-1-yl)nicotinate (Compound 372(Z)) (262.3 mg, Rf=0.4, 1:1 hexane/ethyl acetate) (yield: 58%).

$^1$H NMR (CDCl$_3$, 400 MHz) δ 9.00 (d, 1H, J=1.6 Hz), 8.38 (d, 1H, J=1.6 Hz), 8.17 (br, 0.5H), 7.54-7.58 (m, 2H), 7.32-7.40 (m, 1H), 4.42 (q, 2H, J=7.2 Hz), 3.58-4.30 (br, 4.5H), 1.40 (t, 3H, J=7.2 Hz).

LC-MS: r.t. 2.61 min., m/z 489 (M+1).

Step 37-4

Ethyl (Z)-5-chloro-6-(4-((2-fluoro-6-(trifluoromethyl)phenyl)(hydroxyimino)methyl)-2-oxopiperazin-1-yl)nicotinate (Compound 372(Z); 128.8 mg) and p-toluenesulfonic acid (10 mg) were added to DMSO (2 mL), and the mixture was heated at 80° C. for 1 hour. DBU (910 μL) was added thereto, and the mixture was heated at 120° C. for 30 minutes. A saturated aqueous ammonium chloride solution was added to the reaction solution, followed by extraction with ethyl acetate. The organic layer was dried over magnesium sulfate, and the solvent was distilled off under reduced pressure. The residue was purified by preparative silica gel column chromatography (ethyl acetate/hexane) to give the title compound (50 mg, Rf=0.4, 1:1 hexane/ethyl acetate).

$^1$H NMR (CDCl$_3$, 400 MHz) δ 9.04 (d, 1H, J=1.6 Hz), 8.43 (d, 1H, J=1.6 Hz), 7.79 (dd, 1H, J=1.6, 7.2 Hz), 7.65-7.71 (m, 2H), 4.44 (q, 2H, J=7.2 Hz), 4.15-4.35 (brm, 3H), 3.72-3.82 (m, 3H), 1.43 (t, 3H, J=7.2 Hz).

LC-MS: r.t. 2.66 min., m/z 441 (M+1).

Example 38

Synthesis of 5-chloro-6-(2-oxo-4-(4-(trifluoromethyl)benzo[d]isoxazol-3-yl)piperazin-1-yl)nicotinic acid (Compound 381)

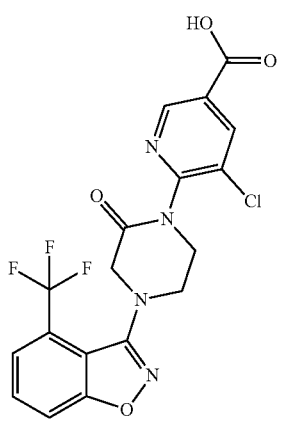 [SMILES: O=C(O)c1cnc(N2CCN(c3noc4cccc(C(F)(F)F)c34)CC2=O)c(Cl)c1]

Ethyl 5-chloro-6-(2-oxo-4-(4-(trifluoromethyl)benzo[d]isoxazol-3-yl)piperazin-1-yl) nicotinate (Compound 371; 45 mg) was added to DME (2 mL). Further, a 2 N aqueous sodium hydroxide solution (1 mL) was added, and the mixture was stirred at room temperature overnight. The solution was concentrated under reduced pressure and neutralized with 1 N hydrochloric acid (2 mL). The resulting powder was collected by filtration and dried under reduced pressure to give 18.3 mg of the title compound.

$^1$H NMR (DMSO, 400 MHz) δ 8.96 (d, 1H, J=1.6 Hz), 8.42 (d, 1H, J=1.6 Hz), 8.10-8.16 (m, 1H), 7.86-7.89 (m, 2H), 4.02-4.15 (m, 3H), 3.62-3.75 (m, 3H).

LC-MS: r.t. 2.66 min., m/z 441 (M+1).

Example 39

Synthesis of methyl 3-chloro-4-(1-(4-(trifluoromethyl)benzo[d]isoxazol-3-yl)-1,2,3,6-tetrahydropyridin-4-yl)benzoate (Compound 391)

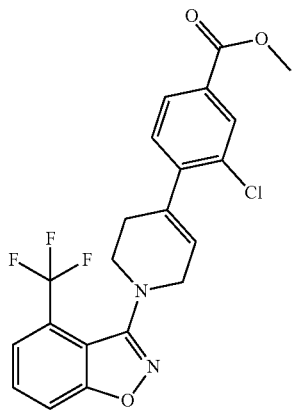 [SMILES: COC(=O)c1ccc(C2=CCN(c3noc4cccc(C(F)(F)F)c34)CC2)c(Cl)c1]

The title compound was obtained according to the procedure of Example 36, except that methyl 4-bromo-3-chlorobenzoate was used in place of 1-chloro-2-iodobenzene.

$^1$H NMR (CDCl$_3$, 400 MHz) δ 8.05 (d, 1H, J=1.2 Hz), 7.92 (dd, 1H, J=1.2, 8.4 Hz), 7.76 (d, 1H, J=7.2 Hz), 7.62-7.68 (m, 2H), 7.57 (d, 1H, J=8.4 Hz), 5.83 (m, 1H, J=7.6 Hz), 4.87 (dd, 1H, J=3.6, 8.0 Hz), 4.10-4.16 (m, 1H), 3.92 (s, 3H), 3.64-3.71 (m, 1H), 3.51-3.58 (m, 1H), 2.36-2.46 (m, 1H), 1.86-1.95 (m, 1H).

LC-MS: r.t. 3.72 min., m/z 437 (M+1).

Example 40

Synthesis of 3-chloro-4-(1-(4-(trifluoromethyl)benzo[d]isoxazol-3-yl)-1,2,3,6-tetrahydropyridin-4-yl)benzoic acid (Compound 401)

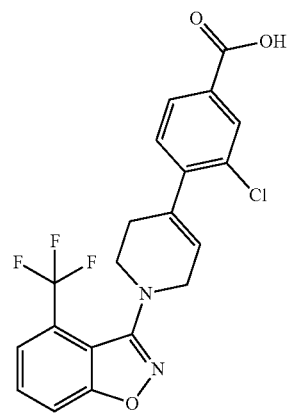 [SMILES: O=C(O)c1ccc(C2=CCN(c3noc4cccc(C(F)(F)F)c34)CC2)c(Cl)c1]

The title compound was obtained according to the procedure of Example 38, except that methyl 3-chloro-4-(1-(4-(trifluoromethyl)benzo[d]isoxazol-3-yl)-1,2,3,6-tetrahydropyridin-4-yl)benzoate (Compound 391) was used in place of Compound 371.

$^1$H NMR (CDCl$_3$, 400 MHz) δ8.13 (d, 1H, J=2 Hz), 7.97 (dd, 1H, J=2, 7.6 Hz), 7.74 (d, 1H, J=7.6 Hz), 7.62-7.68 (m, 2H), 7.39 (d, 1H, J=8 Hz), 5.87-5.91 (m, 1H), 4.05-4.09 (m, 2H), 3.54 (t, 2H, J=6.8 Hz), 2.68-2.73 (m, 2H).

LC-MS: r.t. 3.40 min., m/z 423 (M+1).

Test Example 1

Calcium Assay Using HEK293 Cells That Have Transiently Expressed TRPC Channel
1. TRPC Channel Cell Introduction and Expression A TRPC6 gene was introduced into HEK293 cells (cells derived from human fetal kidney) by lipofection, and the TRPC6 channel was expressed on the cell membrane. Specifically, the plasmid DNA of TRPC6 (pCI-neo; Promega Corporation) was introduced into HEK293 cells using a lipofection reagent, and then cultured at 37° C. for 24 to 48 hours to express the TRPC6 channel on the cell membrane. In the same manner, HEK293 cells into which the TRPC3 gene was introduced were cultured, and the TRPC3 channel was expressed on the cell membrane.
2. Measurement of Changes in Calcium Ion Concentration in TRPC-Expressing Cells The cultured cells were peeled off with trypsin and seeded on a cover glass again, followed by culturing the cells at 37° C. for 3 hours again. A Fura-2 AM calcium indicator was added to the medium, and the cells were cultured at 37° C. for 30 minutes to allow the cells to incorporate the indicator. For the extracellular solution, a Ca$^{2+}$-containing solution and a Ca$^{2+}$-free solution were prepared.

- Ca$^{2+}$-containing solution: 2 mM CaCl$_2$, 132 mM NaCl, 4 mM KCl, 1 mM MgCl$_2$, 5 mM glucose, 5 mM HEPES (pH 7.4)
- Ca$^{2+}$-free solution: 132 mM NaCl, 4 mM KCl, 1 mM MgCl$_2$, 5 mM glucose, 5 mM HEPES (pH 7.4)

After the cells were added to the Ca$^{2+}$-containing solution, the following operation was performed while the fluorescence intensity (510 nm) of Fura-2 was measured at room temperature with an ARGUS CA-20 (Hamamatsu Photonics K.K.) over time.

- 0 minutes: TRPC3-expressing cells or TRPC6-expressing cells are placed in a measurement chamber that contains the Ca$^{2+}$-containing solution.
- After 30 seconds: The Ca$^{2+}$-containing solution is replaced with the Ca$^{2+}$-free solution.
- After 1 minute: A predetermined amount of a test compound is added to the Ca$^{2+}$-free solution.
- After 3 minutes: Carbachol (100 μM) is added to the Ca$^{2+}$-free solution.
- After 7 minutes: The Ca$^{2+}$-free solution is replaced with the Ca$^{2+}$-containing solution that contains a test compound and carbachol (100 PM).
- After 15 minutes: Measurement is ended.

Compound 011 was used as the test compound, and the amount of the test compound added was 0.01, 0.1, 0.5, 1.0, 5.0, 10, or 50 μM. For the control, 0.1% DMSO was used in place of the test compound. Carbachol (cch) is a TRPC-channel-activating reagent. Applying carbachol to cells opens the TRPC channel and allows a large amount of Ca$^2$ in the extracellular solution to flow into the cells. Fura-2 AM has high cell membrane permeability due to the presence of an AM group (acetoxymethyl group), and is thus easily incorporated into the cells. The AM group is hydrolyzed in the cells to become Fura-2. Thus, Fura-2 can form a chelate with Ca$^{2+}$ and is also unlikely to leak out of the cells due to the loss of the AM group.

Figure 2:
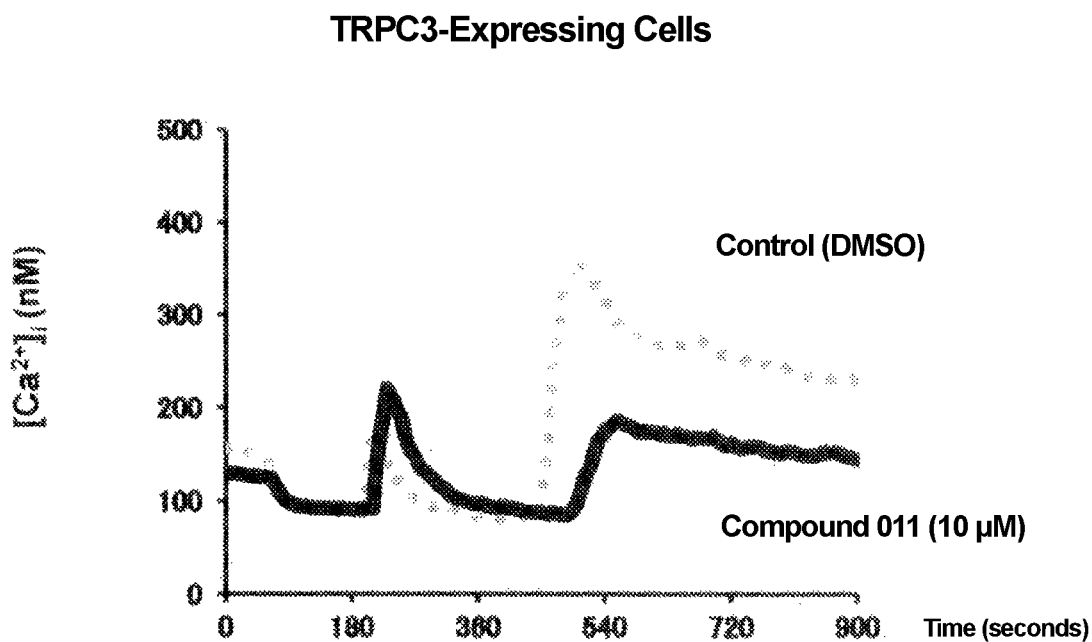
FIG. 2 is a graph illustrating the measurement results of changes in calcium ion concentration in the TRPC3-expressing cells obtained in Test Example 1. The horizontal axis indicates time (seconds), and the vertical axis indicates the calcium ion concentration in cells ($[Ca^{2+}]i$ (nM)).

FIGS. 1 and 2 illustrate the results of measurement in the TRPC6-expressing cells and TRPC3-expressing cells by calcium imaging. The Ca$^2$ concentration in the cells increased due to the addition of carbachol (cch) from about 100 nM to about 280 nM (TRPC6, FIG. 1) or from about 100 nM to about 350 nM (TRPC3, FIG. 2) in the control (DMSO). However, with the test compound (compound 011), the Ca$^{2+}$ concentration increased only from about 100 nM to about 140 nM (TRPC6, FIG. 1) or from about 100 nM to about 180 nM (TRPC3, FIG. 2), indicating that activation of the TRPC6 and TRPC3 channels was suppressed. Concentration-response curves prepared from the measurement results indicate that the IC$_{50}$ for inhibition of the TRPC6 and TRPC3 channels is 4.6 μM (TRPC6) and 0.7 μM (TRPC3).

Test Example 2

Calcium Assay Using HEK293 Cells that has Transiently Expressed TRPC6 Channel

Figure 3:
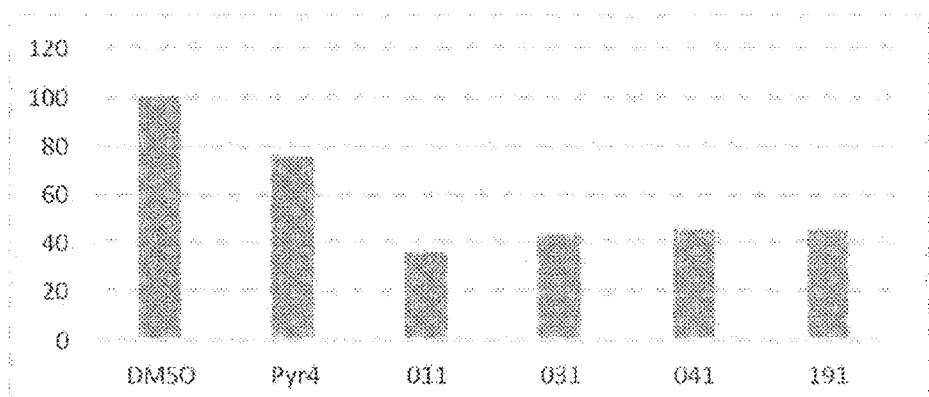
FIG. 3 is a graph illustrating the amount of increase in calcium ions in the TRPC6-expressing cells obtained in Test Example 2. The unit of the vertical axis is percent.

In the same manner as in Test Example 1, the maximum calcium ion concentration was measured after 7 minutes from the start of measurement (i.e., after replacement with the Ca$^{2+}$-containing solution) by using TRPC6-expressing cells prepared in the same manner as in Test Example 1, except that 10 μM of Pyr 4 and 10 μM of compound 011, 031, 041, or 191 (test compound) were used. The average value of calcium ion concentrations up to 30 seconds after the start of measurement (the initial value of calcium ion concentration) was subtracted from the maximum calcium ion concentration, and the calculated value was determined to be the amount of increase in calcium ions. FIG. 3 illustrates the results. FIG. 3 shows the amount of increase in calcium ions relative to the amount of increase in calcium ions in the control (DMSO) taken as 100%. Decreases in calcium ions that flow into the cells due to the addition of the test compounds indicate that activation of the TRPC6 channel was suppressed.

Test Example 2-1

Calcium Assay Using HEK293 Cells that have Transiently Expressed TRPC6 Channel

The calcium ion concentration was measured in the same manner as in Test Example 2, except that 10 μM of compound 011, 361, 362(E), 362(Z), 371, 372(Z), 381, or 401 (test compound) was used, and Pyr 4 was not used, thereby determining the amount of increase in calcium ions. Table 2 illustrates the amount of increase in calcium ions for each test compound relative to the amount of increase in calcium ions in the control (DMSO) taken as 100%.

TABLE 2

| | Compound Number | | | | | | | |
|---|---|---|---|---|---|---|---|---|
| | 011 | 361 | 362 (E) | 362 (Z) | 371 | 372 (Z) | 381 | 401 |
| Ca$^{2+}$ Concentration | 21% | 72% | 65% | 54% | 61% | 72% | 57% | 19% |

Decreases in calcium ions that flow into the cells due to the addition of the test compounds indicate that activation of the TRPC6 channel was suppressed.

Test Example 3

Calcium Assay Using HEK293 Cells that have Transiently Expressed TRPC6 Channel

Figure 4:
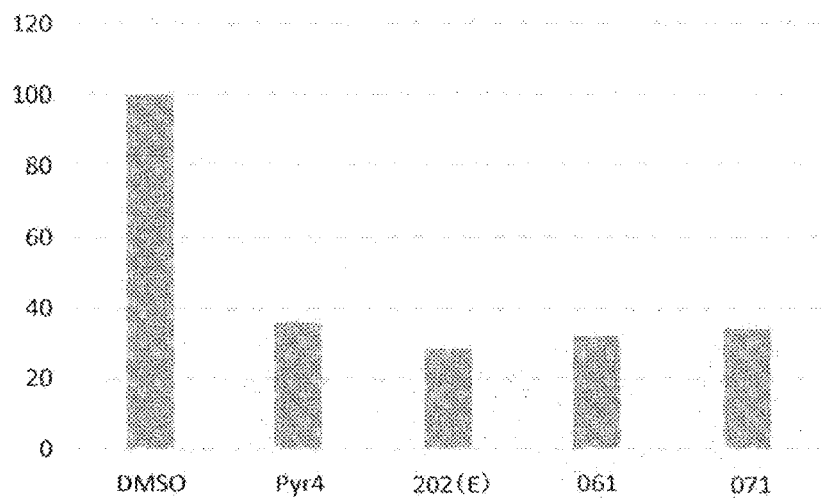
FIG. 4 is a graph illustrating the amount of increase in calcium ions in the TRPC6-expressing cells obtained in Test Example 3. The unit of the vertical axis is percent.

In the same manner as in Test Example 2, the calcium ion concentration was measured, except that 10 μM of Pyr 4 and 10 μM of compound 202(E), 061, or 071 (test compound) were used, and ATP was used as a TRPC channel activating reagent instead of carbachol, thereby determining the amount of increase in calcium ions. FIG. 4 illustrates the results. FIG. 4 shows the amount of increase in calcium ions relative to the amount of increase in calcium ions in the control (DMSO) taken as 100%. Decreases in calcium ions that flow into the cells due to the addition of the test compounds indicate that activation of the TRPC6 channel was suppressed.

Test Example 4

Electrophysiological Evaluation Using HEK293 Cells that have Transiently Expressed TRPC6 Channel Evaluation was performed using TRPC6-expressing cells cultured in the same manner as in Test Example 1. The transfected cells were placed in a chamber set in a microscope, and TRPC6 current was measured with a patch glass electrode (5 to 10 MΩ) in whole-cell mode. The extracellular solution and intracellular solution used in this evaluation are listed below.

Extracellular Solution: 140 mM NaCl, 5 mM KCl, 1 mM $CaCl_2$, 1.2 mM $MgCl_2$, 10 mM Glucose, 10 mM HEPES (pH 7.4)

Intracellular Solution: 120 mM CsOH, 120 mM Aspartate, 20 mM CsCl, 2 mM $MgCl_2$, 1.5 mM $CaCl_2$, 5 mM EGTA, 10 mM Glucose, 10 mM HEPES, 2 mM ATP-Na, 0.1 mM GTP (pH 7.4)

The holding potential was fixed at −50 mV. TRPC current was evoked by adding carbachol (100 μM) to the cells. Evaluation was performed on the change in current caused by adding 30 μM of a test compound (compound 011) to the cells for 30 seconds after 20 seconds from the addition of carbachol.

Figure 5:
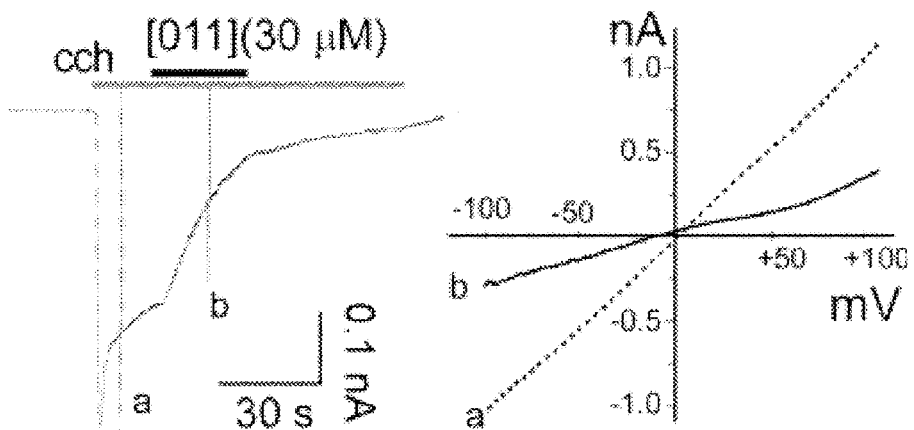
FIG. 5 is graphs illustrating the electrophysiological evaluation on the TRPC6-expressing cells obtained in Test Example 4.

FIG. 5 illustrates the results of Test Example 4 (the effect of compound 011 on TRPC6 current evoked by carbachol: cch). The graph on the left in FIG. 5 illustrates a trace of −50 mV. The graph on the right in FIG. 5 illustrates current-voltage characteristic curves measured by applying ramp waves (linear voltage of −100 to +100 mV) for about one second at the points indicated by "a" and "b" in the graph on the left. The significant decrease in the amount of current observed after the addition of the test compound indicates an effect of suppressing the activation of the TRPC6 channel brought about by adding the test compound.

Test Example 5

Fibrosis Inhibition Evaluation Experiment 1: Western Blotting and Cell Morphology Observation The expression of α-smooth muscle actin (α-SMA) in fibroblasts was evaluated by western blotting. Dermal fibroblasts were isolated from 1 to 3-day-old mice, and $2.5 \times 10^5$ cells were seeded in a 12-well plate. After 24 hours, the medium was replaced with a medium free of fetal bovine serum, and the cells were cultured for another 24 hours. Thereafter, 10 ng/ml of transforming growth factor β1 (TGFβ1) was added, and the cells were cultured for 48 hours. At the same time as TGFβ1 was added, a test compound (compound 011) of a predetermined concentration (0.1 μM, 1 μM, 10 μM) and 10 μM of Pyr 2 or DMSO (solvent control) were also added. The morphology of the cultured cells was observed with an all-in-one fluorescence microscope (Keyence BZ-X700; magnification: 20 times). The cultured cells were dissolved in a lysis buffer (140 mM NaCl, 20 mM Tris-HCl pH 7.8, 1% Triton-X100, 0.05% sodium deoxycholate, 0.1% SDS, 2 mM EDTA, proteinase inhibitor cocktail), and separated by SDS-PAGE, followed by detecting α-SMA using anti-α-SMA antibody (Sigma) as the primary antibody and anti-mouse IgG antibody (cell signaling) fused with horse radish peroxidase as the secondary antibody.

Figure 6:
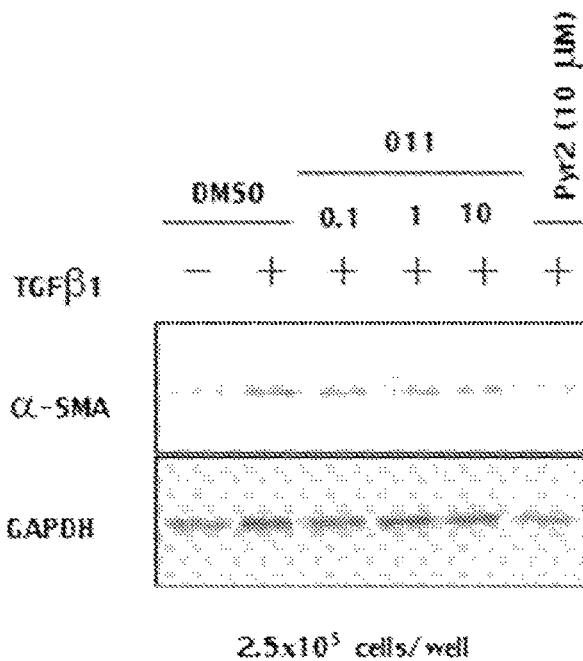
FIG. 6 is a photograph that shows the results of western blotting in Test Example 5.

FIG. 6 illustrates the results of western blotting. FIG. 6 shows that the test compound (especially 10 μM) and Pyr 2 had a lighter coloration of the α-SMA antibody compared with the control (TGFβ1+ in DMSO), indicating that the test compound potently inhibited the expression of α-SMA induced by TGFβ1.

Additionally, microscopic observation confirmed that while the addition of Pyr 2 led to cell elongation, the addition of the test compound caused no change in cell morphology and no cell damage.

Test Example 6

Fibrosis Inhibition Evaluation Experiment 2: Immunofluorescent Staining

In the same manner as in Test Example 5, dermal fibroblasts were isolated from mice, and sterilized cover glass (diameter: 12 mm) was placed in a 12-well plate. On the cover glass, $2.5 \times 10^5$ cells were seeded and grown. After 24 hours, the medium was replaced with a medium free of fetal bovine serum, and the cells were cultured for another 24 hours. Separately, cardiac fibroblasts were isolated from 1 to 2-day-old rats and treated in the same manner as for the dermal fibroblasts. Thereafter, 10 ng/ml TGFβ1 was added to the dermal fibroblasts, and 2 ng/ml TGFβ2 was added to the cardiac fibroblasts, followed by culturing the cells for 48 hours. At the same time as TGFβ was added, 10 μM of a test compound (compound 011), 10 μM of Pyr 2 (conventional inhibitor), or DMSO (solvent control) was also added. Separately, cultured cells to which TGFβ-free phosphate buffered saline (PBS) was added were also prepared. After culturing, the cells were immobilized with 4% paraformaldehyde and then permeabilized with tris-buffered saline (TBS) (pH 7.4) containing 0.5% Triton-X100. After blocking with 1% bovine serum albumin, α-SMA was detected using anti-α-SMA antibody (Sigma) as the primary antibody and anti-mouse IgG antibody (Molecular Probes) fused with Alexa 488 as the secondary antibody, and an image was acquired using a fluorescence microscope (Keyence) with a 20× objective lens. The average fluorescence brightness (fluorescence intensity/pixel) per cell area was calculated and analyzed using Image J software.

Figure 7:
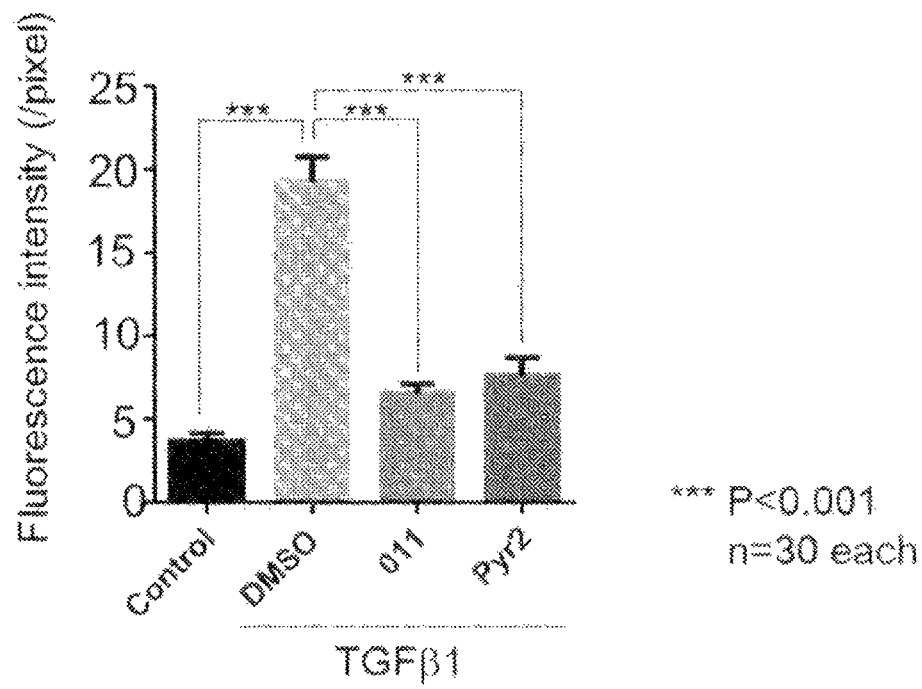
FIG. 7 is a graph illustrating the expression of α-SMA obtained by immunofluorescent staining using dermal fibroblasts in Test Example 6. The vertical axis of the graph indicates fluorescence intensity (/pixel).
Figure 8:
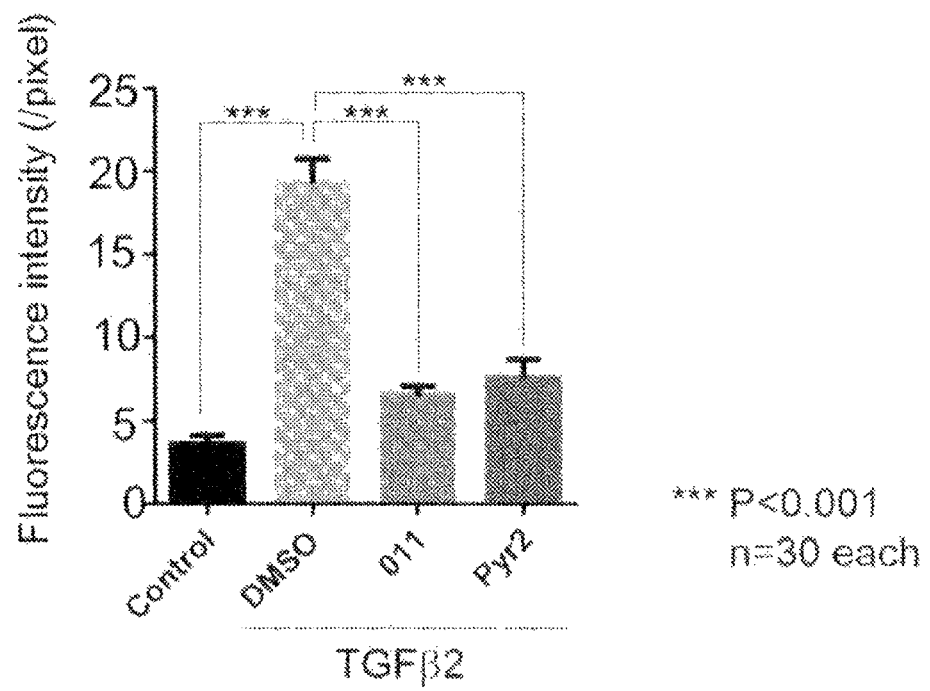
FIG. 8 is a graph illustrating the expression of α-SMA obtained by immunofluorescent staining using cardiac fibroblasts in Test Example 6. The vertical axis of the graph indicates fluorescence intensity (/pixel).

FIG. 7 and FIG. 8 illustrate the results of fluorescent staining (FIG. 7: dermal fibroblasts; FIG. 8: cardiac fibroblasts). In both types of cells, TGFβ treatment enhanced the expression of fibrous α-SMA. Compound 011 almost completely suppressed the expression of α-SMA induced by TGFβ, substantially in the same manner as with Pyr2.

The invention claimed is:

1. A pharmaceutical composition comprising a compound represented by formula (1):

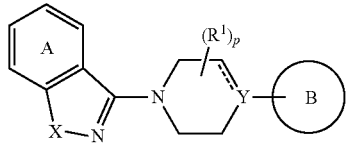

wherein in formula (1), the benzisoxazole or benzisothiazole skeleton is substituted at the 4-position;
A is a benzene ring optionally substituted with at least one substituent selected from the group consisting of the following A-1 to A-16:
A-1) halogen,
A-2) hydroxyl,
A-3) nitro,
A-4) cyano,
A-5) carboxyl,
A-6) optionally substituted amino,
A-7) optionally substituted cyclic amino,
A-8) optionally substituted lower alkyl,
A-9) optionally substituted lower alkoxy,
A-10) lower alkoxycarbonyl,
A-11) lower alkylsulfonyl,
A-12) carbamoyl optionally substituted with lower alkyl or lower alkylsulfonyl,
A-13) optionally substituted cyclic aminocarbonyl,
A-14) sulfamoyl optionally substituted with lower alkyl,
A-15) optionally substituted cyclic aminosulfonyl, and
A-16) tetrazolyl;
B is a monocyclic aryl or a monocyclic or a bicyclic heteroaryl, wherein
the monocyclic aryl is optionally substituted with at least one substituent selected from the group consisting of the following B-1 to B-16, and
the monocyclic or the bicyclic heteroaryl is optionally substituted with at least one substituent selected from the group consisting of the following B-1 to B-17:
B-1) halogen,
B-2) hydroxyl,
B-3) nitro,
B-4) cyano,
B-5) carboxyl
B-6) optionally substituted amino,
B-7) optionally substituted cyclic amino,
B-8) optionally substituted lower alkyl,
B-9) optionally substituted lower alkoxy,
B-10) lower alkoxycarbonyl,
B-11) lower alkyl sulfonyl,
B-12) carbamoyl optionally substituted with lower alkyl or lower alkylsulfonyl,
B-13) optionally substituted cyclic aminocarbonyl,
B-14) sulfamoyl optionally substituted with lower alkyl,
B-15) optionally substituted cyclic aminosulfonyl,
B-16) tetrazolyl, and
B-17) oxo;
X is an oxygen atom or a sulfur atom;
Y is a nitrogen atom or a carbon atom;
------ of ------ Y is a single or double bond when Y is a carbon atom, or
------ of ------ Y is a single bond when Y is a nitrogen atom;
each $R^1$ independently represents lower alkyl, or
two $R^1$s may be bound to each other to form methylene, dimethylene, trimethylene, or tetramethylene, thus forming a crosslinked structure, or
two $R^1$s may be bound to each other to form a saturated fused heterocycle together with nitrogen and carbon atoms constituting a ring containing Y, the saturated fused heterocycle being a fused ring of a pyrazine ring or a piperidine ring and a cyclopentane ring or a cyclohexane ring;
p is 0, 1, or 2; or
$(R^1)_p$ is oxo;
a salt thereof; or
a prodrug thereof.

2. The pharmaceutical composition according to claim 1, wherein in formula (1), B is an optionally substituted monocyclic aryl or an optionally substituted monocyclic or bicyclic nitrogen-containing heteroaryl.

3. The pharmaceutical composition according to claim 1, wherein in formula (1), B is substituted pyridyl or substituted phenyl, wherein at least one of the carbon atoms in ortho-positions relative to the Y-bound carbon atom on the pyridine or benzene ring is substituted.

4. The pharmaceutical composition according to claim 1, wherein in formula (1),
A is a benzene ring optionally substituted with at least one substituent selected from the group consisting of halogen, lower alkoxy, and optionally halogen-substituted lower alkyl;
B is pyridyl or phenyl each optionally substituted with at least one substituent selected from the group consisting of B-1, B-5, B-8, B-10, B-12, and B-13:
B-1) halogen,
B-5) carboxyl,
B-8) optionally substituted lower alkyl,
B-10) lower alkoxycarbonyl,
B-12) carbamoyl optionally substituted with lower alkyl or lower alkylsulfonyl, and
B-13) optionally substituted cyclic aminocarbonyl; and
each $R^1$ independently represents $C_1$-$C_3$ alkyl, or
two $R^1$s are bound to each other to form a methylene group, a dimethylene group, or a trimethylene group, or $(R^1)_p$ is oxo.

5. The pharmaceutical composition according to claim 1, wherein the compound is represented by formula (1A):

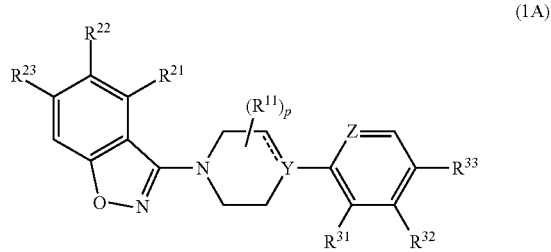

wherein
Z is a nitrogen atom or CH;
Y is a nitrogen atom or a carbon atom;
------ of ------ Y is a single or double bond when Y is a carbon atom, or
------ of ------ Y is a single bond when Y is a nitrogen atom;
each $R^{11}$ independently represents methyl or ethyl, or two R¹¹s may be bound to each other to form a cross-linked structure by methylene, dimethylene, or trimethylene;

p is 0, 1, or 2; or $(R^{11})_p$ is oxo;

$R^{21}$, $R^{22}$, and $R^{23}$ independently represent a hydrogen atom, halogen, or trifluoromethyl; and $R^{31}$, $R^{32}$, and $R^{33}$ independently represent a hydrogen atom, halogen, halogen-substituted lower alkyl, methyl, carboxyl, lower alkoxycarbonyl, monomethyl aminocarbonyl, or dimethylaminocarbonyl.

6. The pharmaceutical composition according to claim 5, wherein in formula (1A), $R^{21}$ is chlorine or trifluoromethyl, $R^{22}$ and $R^{23}$ are each a hydrogen atom, $R^{31}$ is a chlorine atom, $R^{32}$ is a hydrogen atom, and $R^{33}$ is a hydrogen atom, carboxyl, or lower alkoxycarbonyl.

7. A pharmaceutical composition comprising a compound selected from the group consisting of Compound 011, Compound 021, Compound 031, Compound 041, Compound 061, Compound 071, Compound 081, Compound 091, Compound 101, Compound 111, Compound 121, Compound 131, Compound 141, Compound 151, Compound 161, Compound 171, Compound 191, Compound 221, Compound 281, Compound 311, Compound 321, Compound 331, Compound 341, Compound 351, Compound 361, Compound 371, Compound 381, Compound 391, and Compound 401, as represented by the following structures,

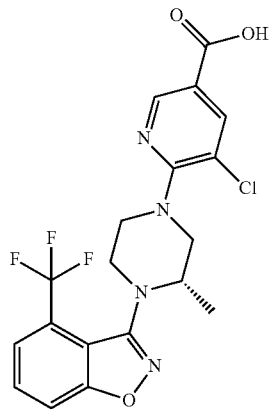

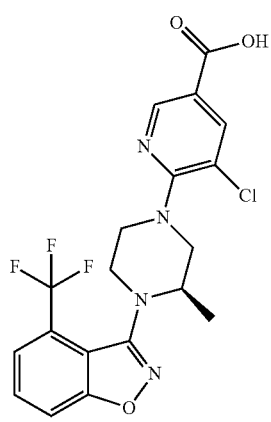

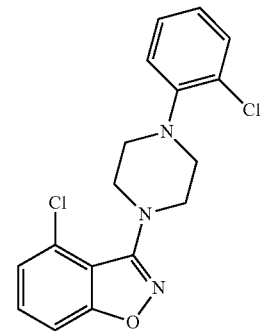

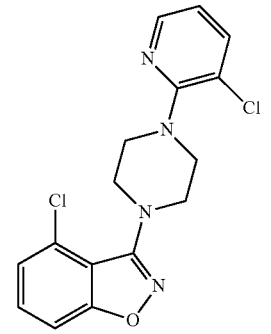

081
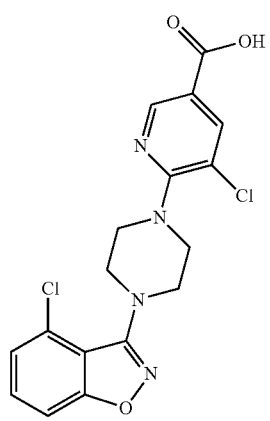
091
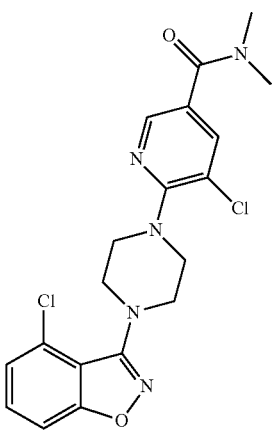
101
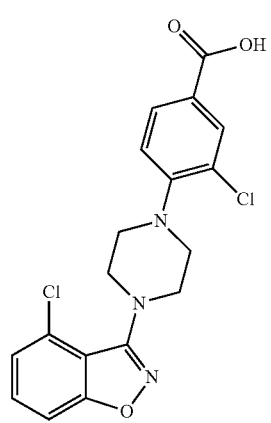
111
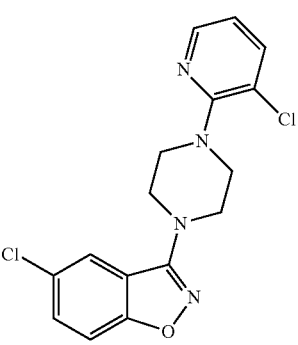
121
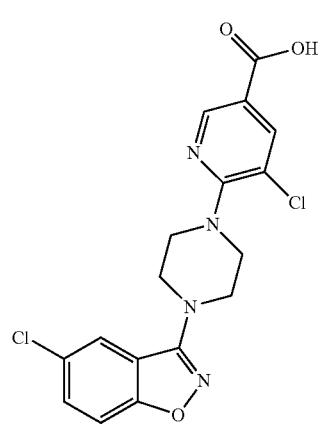
131
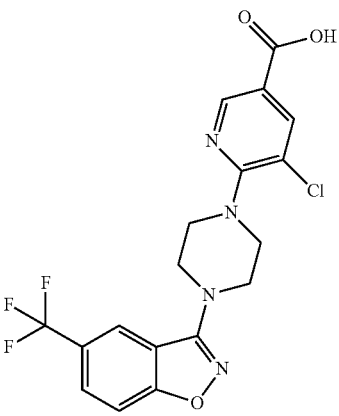
141
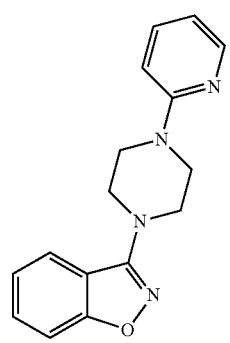
151
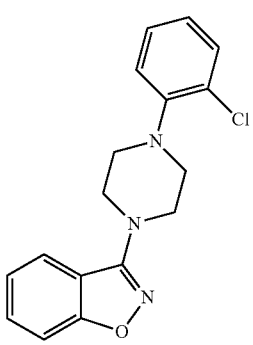

161 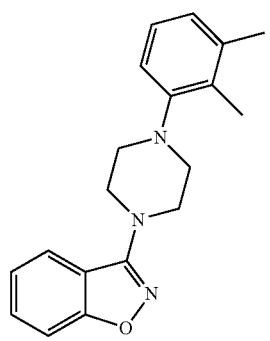
171 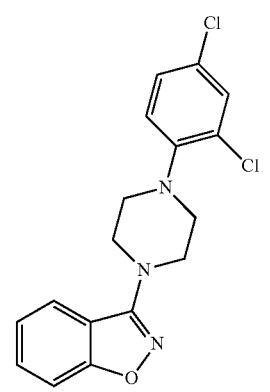
191 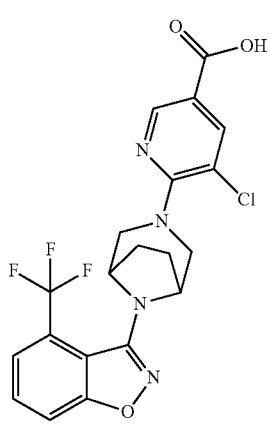
221 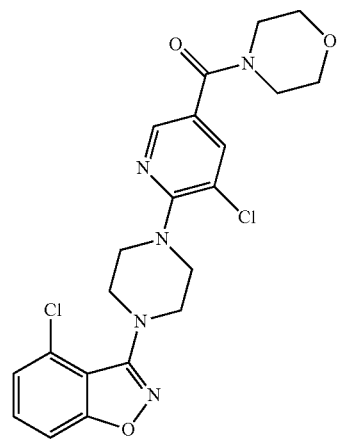
281 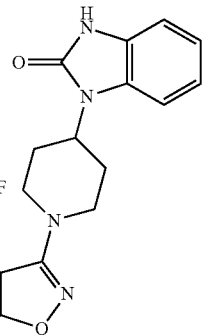
311 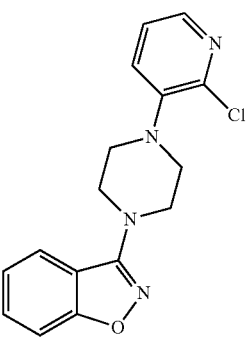
321 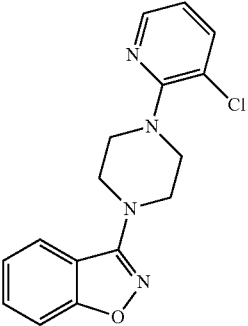
331 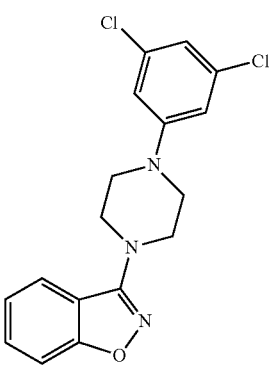

341
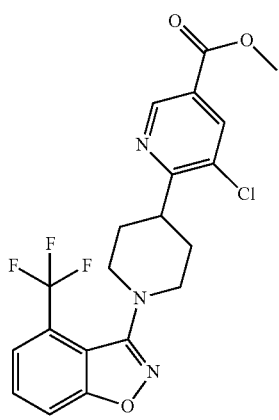
351
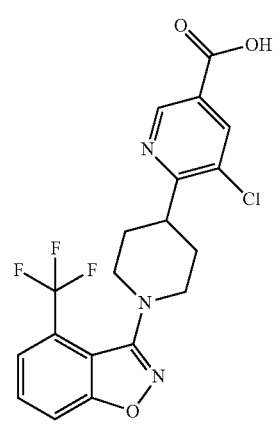
361
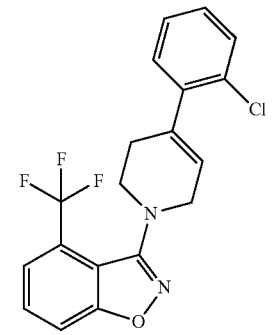
371
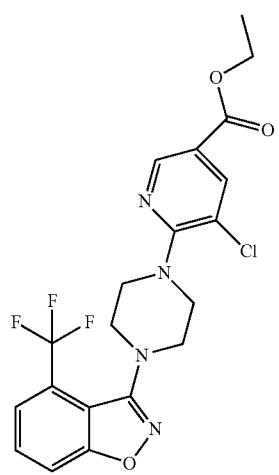
381
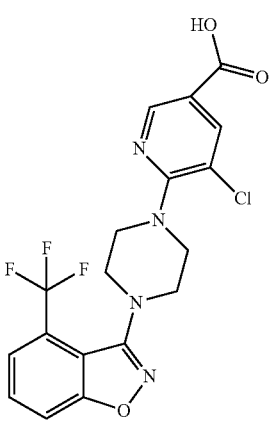
391
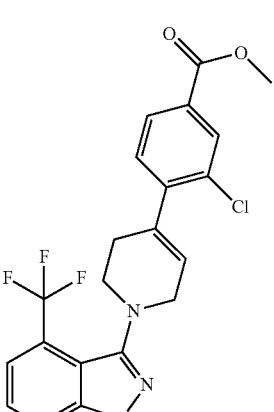
401
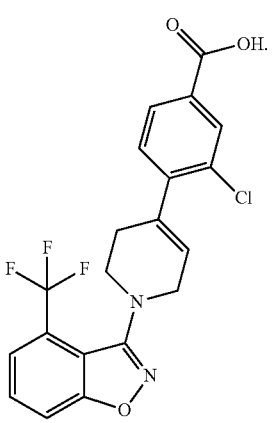
8. A method of treating a TRPC3 and/or TRPC6-related disease, the method comprising administering to a patient in need thereof the pharmaceutical composition comprising a compound represented by formula (1):
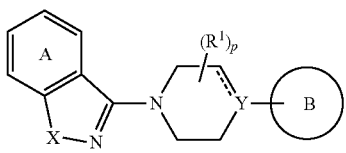
(1)

wherein in formula (1),
A is a benzene ring optionally substituted with at least one substituent selected from the group consisting of the following A-1 to A-16:
A-1) halogen,
A-2) hydroxyl,
A-3) nitro,
A-4) cyano,
A-5) carboxyl,
A-6) optionally substituted amino,
A-7) optionally substituted cyclic amino,
A-8) optionally substituted lower alkyl,
A-9) optionally substituted lower alkoxy,
A-10) lower alkoxycarbonyl,
A-11) lower alkylsulfonyl,
A-12) carbamoyl optionally substituted with lower alkyl or lower alkylsulfonyl,
A-13) optionally substituted cyclic aminocarbonyl,
A-14) sulfamoyl optionally substituted with lower alkyl,
A-15) optionally substituted cyclic aminosulfonyl, and
A-16) tetrazolyl;
B is a monocyclic aryl or a monocyclic or a bicyclic heteroaryl, wherein the monocyclic aryl is optionally substituted with at least one substituent selected from the group consisting of the following B-1 to B-16, and
the monocyclic or the bicyclic heteroaryl is optionally substituted with at least one substituent selected from the group consisting of the following B-1 to B-17:
B-1) halogen,
B-2) hydroxyl,
B-3) nitro,
B-4) cyano,
B-5) carboxyl
B-6) optionally substituted amino,
B-7) optionally substituted cyclic amino,
B-8) optionally substituted lower alkyl,
B-9) optionally substituted lower alkoxy,
B-10) lower alkoxycarbonyl,
B-11) lower alkyl sulfonyl,
B-12) carbamoyl optionally substituted with lower alkyl or lower alkylsulfonyl,
B-13) optionally substituted cyclic aminocarbonyl,
B-14) sulfamoyl optionally substituted with lower alkyl,
B-15) optionally substituted cyclic aminosulfonyl,
B-16) tetrazolyl, and
B-17) oxo;
X is an oxygen atom or a sulfur atom;
Y is a nitrogen atom or a carbon atom;
------ of ------ Y is a single or double bond when Y is a carbon atom, or
------ of ------ Y is a single bond when Y is a nitrogen atom;
each $R^1$ independently represents lower alkyl, or
two $R^1$s may be bound to each other to form methylene, dimethylene, trimethylene, or tetramethylene, thus forming a crosslinked structure, or
two $R^1$s may be bound to each other to form a saturated fused heterocycle together with nitrogen and carbon atoms constituting a ring containing Y, the saturated fused heterocycle being a fused ring of a pyrazine ring or a piperidine ring and a cyclopentane ring or a cyclohexane ring;
p is 0, 1, or 2; or
$(R^1)_p$ is oxo;
a salt thereof; or
a prodrug thereof wherein the TRPC3 and/or TRPC6-related disease is fibrosis, cardiac hypertrophy, amyotrophic lateral sclerosis (ALS), muscular dystrophy, ulcerative colitis, Crohn's disease, non-alcoholic steatohepatitis (NASH), Williams syndrome, chronic nephropathy, or pulmonary hypertension.

9. A method of regulating or inhibiting the activity of a TRPC3 channel and/or a TRPC6 channel, the method comprising administering to a patient in need thereof a compound represented by formula (1):

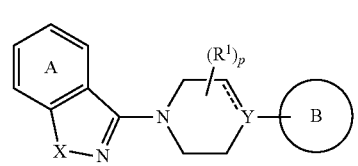

(1)

wherein in formula (1), A is a benzene ring optionally substituted with at least one substituent selected from the group consisting of the following A-1 to A-16:
A-1) halogen,
A-2) hydroxyl,
A-3) nitro,
A-4) cyano,
A-5) carboxyl,
A-6) optionally substituted amino,
A-7) optionally substituted cyclic amino,
A-8) optionally substituted lower alkyl,
A-9) optionally substituted lower alkoxy,
A-10) lower alkoxycarbonyl,
A-11) lower alkylsulfonyl,
A-12) carbamoyl optionally substituted with lower alkyl or lower alkylsulfonyl,
A-13) optionally substituted cyclic aminocarbonyl,
A-14) sulfamoyl optionally substituted with lower alkyl,
A-15) optionally substituted cyclic aminosulfonyl, and
A-16) tetrazolyl;
B is a monocyclic aryl or a monocyclic or a bicyclic heteroaryl, wherein the monocyclic aryl is optionally substituted with at least one substituent selected from the group consisting of the following B-1 to B-16, and
the monocyclic or the bicyclic heteroaryl is optionally substituted with at least one substituent selected from the group consisting of the following B-1 to B-17:
B-1) halogen,
B-2) hydroxyl,
B-3) nitro,
B-4) cyano,
B-5) carboxyl
B-6) optionally substituted amino,
B-7) optionally substituted cyclic amino,
B-8) optionally substituted lower alkyl,
B-9) optionally substituted lower alkoxy,
B-10) lower alkoxycarbonyl,
B-11) lower alkyl sulfonyl,
B-12) carbamoyl optionally substituted with lower alkyl or lower alkylsulfonyl,
B-13) optionally substituted cyclic aminocarbonyl,
B-14) sulfamoyl optionally substituted with lower alkyl,
B-15) optionally substituted cyclic aminosulfonyl,
B-16) tetrazolyl, and
B-17) oxo;
X is an oxygen atom or a sulfur atom;
Y is a nitrogen atom or a carbon atom;

------ of ------ Y is a single or double bond when Y is a carbon atom, or

------ of ------ Y is a single bond when Y is a nitrogen atom;

each R$^1$ independently represents lower alkyl, or two R$^1$s may be bound to each other to form methylene, dimethylene, trimethylene, or tetramethylene, thus forming a crosslinked structure, or two R$^1$s may be bound to each other to form a saturated fused heterocycle together with nitrogen and carbon atoms constituting a ring containing Y, the saturated fused heterocycle being a fused ring of a pyrazine ring or a piperidine ring and a cyclopentane ring or a cyclohexane ring;

p is 0, 1, or 2; or (R$^1$)$_p$ is oxo;

a salt thereof, or a prodrug thereof.

10. The method according to claim 8, wherein Y is a nitrogen atom;

------ of ------ Y is a single bond;

the TRPC3 and/or TRPC6-related disease is muscular dystrophy, Crohn's disease, Williams syndrome, pulmonary hypertension, or chronic nephropathy;

A is a benzene ring optionally substituted with at least one substituent selected from the group consisting of the following A-1, A-3 to A-8, and A-10 to A-16:

A-1) halogen,
A-3) nitro,
A-4) cyano,
A-5) carboxyl,
A-6) optionally substituted amino,
A-7) optionally substituted cyclic amino,
A-8) optionally substituted lower alkyl,
A-10) lower alkoxycarbonyl,
A-11) lower alkylsulfonyl,
A-12) carbamoyl optionally substituted with lower alkyl or lower alkylsulfonyl,
A-13) optionally substituted cyclic aminocarbonyl,
A-14) sulfamoyl optionally substituted with lower alkyl,
A-15) optionally substituted cyclic aminosulfonyl, and
A-16) tetrazolyl; and B is monocyclic aryl or monocyclic or bicyclic heteroaryl, wherein the monocyclic aryl is optionally substituted with at least one substituent selected from the group consisting of the following B-1 to B-5, B-7 to B-11, and B-13 to B-16, and the monocyclic or bicyclic heteroaryl is optionally substituted with at least one substituent selected from the group consisting of the following B-1 to B-5, B-7 to B-11, and B-13 to B-17:

B-1) halogen,
B-2) hydroxyl,
B-3) nitro,
B-4) cyano,
B-5) carboxyl,
B-7) optionally substituted cyclic amino,
B-8) optionally substituted lower alkyl,
B-9) optionally substituted lower alkoxy,
B-10) lower alkoxycarbonyl,
B-11) lower alkyl sulfonyl,
B-13) optionally substituted cyclic aminocarbonyl,
B-14) sulfamoyl optionally substituted with lower alkyl,
B-15) optionally substituted cyclic aminosulfonyl,
B-16) tetrazolyl, and
B-17) oxo.

11. The method according to claim 10, wherein in formula (1), the benzisoxazole or benzisothiazole skeleton is substituted at the 4-position.

12. The method according to claim 10, wherein in formula (1), B is substituted pyridyl or substituted phenyl, wherein at least one of the carbon atoms in ortho-positions relative to the Y-bound carbon atom on the pyridine or benzene ring is substituted.

13. The method according to claim 10, wherein in formula (1),

A is a benzene ring optionally substituted with at least one substituent selected from the group consisting of halogen, lower alkoxy, and optionally halogen-substituted lower alkyl;

B is pyridyl or phenyl each optionally substituted with at least one substituent selected from the group consisting of the following B-1, B-5, B-8, B-10, B-12, and B-13:

B-1) halogen,
B-5) carboxyl,
B-8) optionally substituted lower alkyl,
B-10) lower alkoxycarbonyl,
B-12) carbamoyl optionally substituted with lower alkyl or lower alkylsulfonyl, and
B-13) optionally substituted cyclic aminocarbonyl; and each R1 independently represents C1-C3 alkyl, or two R1s are bound to each other to form a methylene group, a dimethylene group, or a trimethylene group, or (R1)p is oxo.

14. The method of claim 9, wherein in formula (1), B is an optionally substituted monocyclic aryl or an optionally substituted monocyclic or bicyclic nitrogen-containing heteroaryl, a salt thereof, or a prodrug thereof.

* * * * *